United States Patent
Mann

(10) Patent No.: US 12,145,899 B2
(45) Date of Patent: Nov. 19, 2024

(54) DEUTERATED ANALOGS OF ACETYL-LEUCINE

(71) Applicant: INTRABIO LTD., London (GB)

(72) Inventor: Michiko Mann, Oxford (GB)

(73) Assignee: INTRABIO LTD., London (GB)

( * ) Notice: Subject to any disclaimer, the term of this patent is extended or adjusted under 35 U.S.C. 154(b) by 736 days.

(21) Appl. No.: 17/311,240

(22) PCT Filed: Dec. 6, 2019

(86) PCT No.: PCT/IB2019/060525
§ 371 (c)(1),
(2) Date: Jun. 4, 2021

(87) PCT Pub. No.: WO2020/115715
PCT Pub. Date: Jun. 11, 2020

(65) Prior Publication Data
US 2022/0024858 A1 Jan. 27, 2022

Related U.S. Application Data

(60) Provisional application No. 62/776,297, filed on Dec. 6, 2018.

(51) Int. Cl.
*C07C 233/47* (2006.01)
*C07B 59/00* (2006.01)

(52) U.S. Cl.
CPC .......... *C07C 233/47* (2013.01); *C07B 59/001* (2013.01)

(58) Field of Classification Search
None
See application file for complete search history.

(56) References Cited

U.S. PATENT DOCUMENTS 10,950,670 B2 * 3/2021 Luo ................. H10K 77/10
11,471,434 B2 * 10/2022 Strupp ................. A61P 25/06
(Continued)

FOREIGN PATENT DOCUMENTS

JP 2016513084 A 5/2016
WO WO-9526325 A2 10/1995
(Continued)

OTHER PUBLICATIONS

Dyck et al., (1986) Journal of Neurochemistry, 46: 399-404 (Year: 1986).*
(Continued)

*Primary Examiner* — Jeffrey S Lundgren
*Assistant Examiner* — Anthony Joseph Seitz
(74) *Attorney, Agent, or Firm* — Sterne, Kessler, Goldstein & Fox P.L.L.C.

(57) ABSTRACT

The present disclosure provides compounds represented by Formula I: I, and the pharmaceutically acceptable salts and solvates thereof, wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined as set forth in the specification, and the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more. The present disclosure also provides compounds having Formula I for use to treat or delay the progression of a lysosomal storage disorder or a neurodegenerative disease in a subject, provide neuroprotection in a subject having a lysosomal disorder, treat or prevent a migraine, and the symptoms associated therewith, in a subject, or improve mobility and/or cognitive function in a subject.

(Continued)

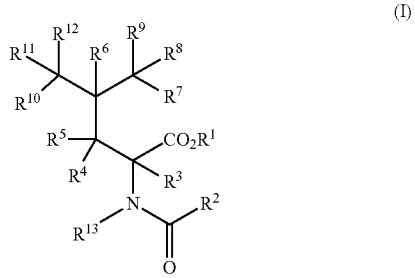

(I)

20 Claims, 6 Drawing Sheets

(56) References Cited

U.S. PATENT DOCUMENTS

| | | | | |
|---|---|---|---|---|
| 2021/0106548 | A1* | 4/2021 | Factor | A61K 31/198 |
| 2022/0142959 | A1* | 5/2022 | Factor | A61K 31/198 |
| 2022/0362189 | A1* | 11/2022 | Factor | A61K 31/197 |
| 2023/0051742 | A1* | 2/2023 | Strupp | A61P 25/28 |
| 2023/0201150 | A1* | 6/2023 | Strupp | A61K 31/198 |
| | | | | 514/561 |
| 2023/0346732 | A1* | 11/2023 | Factor | A61K 31/198 |

FOREIGN PATENT DOCUMENTS

| | | | |
|---|---|---|---|
| WO | WO-2006036634 | A2 | 4/2006 |
| WO | WO-2014122184 | A1 | 8/2014 |
| WO | WO-2017182802 | A1 | 10/2017 |
| WO | WO-2018029657 | A1 | 2/2018 |
| WO | WO-2018029658 | A1 * | 2/2018 ............ A61K 31/13 |
| WO | WO-2018178670 | A1 | 10/2018 |
| WO | WO-2018229738 | A1 | 12/2018 |
| WO | WO-2019079536 | A1 | 4/2019 |
| WO | WO-2019159110 | A1 | 8/2019 |
| WO | WO-2020115715 | A1 | 6/2020 |
| WO | WO-2020178721 | A1 | 9/2020 |
| WO | WO-2020261230 | A1 | 12/2020 |

OTHER PUBLICATIONS

Oba et al., J. Org. Chem. 2001, 66, 17, 5919-5922 (Year: 2001).*
Te Vruchte et al., Relative acidic compartment volume as a lysosomal storage disorder-associated biomarker. J Clin Invest. Mar. 2014;124(3):1320-8, American Society for Clinical Investigation (Year: 2014).*
Aerts, J.M., et al., "Biomarkers in the diagnosis of lysosomal storage disorders: proteins, lipids, and inhibodies," J Inherit Metab Dis 34(3):605-619, Wiley, United States (Jun. 2011).
Antonenko, L.M., "Second Congress <<International Academy of Dizziness>>," Nevrologicheskiy zhurnal 20(4):51-53, Federal State Autonomous Institution "National Medical Research Center for Children's Health" of the Ministry of Health of the Russian Federation, Russia (Dec. 2015).
Akita, H., et al., "Creation of a thermostable NADP+-dependent D-amino acid dehydrogenase from Ureibacillus thermosphaericus strain 11 meso-diaminopimelate dehydrogenase by site-directed mutagenesis," Biotechnol Lett 34(9):1693-1699, Springer Nature, Germany (Sep. 2012).
Akita, H., et al., "Spectrophotometric assay of D-isoleucine using an artificially created D-amino acid dehydrogenase," Biotechnol Lett 36(11):2245-2248, Springer Nature, Germany (Nov. 2014).
Almanov, G.A., et al., "Structure of free radicals in irradiated acetyl-L-leucine single crystals," Khimia Vysokikh Energii 20(5):430-435, Nauka, Union of Soviet Socialist Republics (Sep.-Oct. 1986).
Almanov, G.A., et al., "Structure of free radicals in irradiated acetyl-L-leucine single crystals at 77 K," J Struct Chem 29(2):216-220, Pleiades Publishing, Union of Soviet Socialist Republics (Mar. 1988).
August, R.A., et al., "Stereospecific synthesis of (2S,4R)-[5,5,5-2H3]-leucine," Tetrahedron Lett 33:4617-4620, Elsevier, Netherlands (Aug. 1992).
Belikov, V.G., Pharmaceutical Chemistry: Manual, 4$^{th}$ edition, pp. 27-29, MEDpress-inform, Moscow, Russia (2007).
Bingham, A.L., et al., "Over one hundred solvates of sulfathiazole," Chem Commun 603-604 Royal Society of Chemistry, United Kingdom (Mar. 2001).
Bobillo Lobato, J., et al., "Biomarkers in Lysosomal Storage Diseases," Diseases 4(4):40, MDPI, Switzerland (Dec. 2016).
Bremova, T., et al., "Acetyl-dl-leucine in Niemann-Pick type C: A case series," Neurology 85(16):1368-1375, Wolters Kluwer, Netherlands (Oct. 2015).
Caira, M.R., et al., "Preparation and crystal characterization of a polymorph, a monohydrate, and an ethyl acetate solvate of the antifungal fluconazole," J Pharm Sci 93(3):601-611, Elsevier, Netherlands (Mar. 2004).
Cardellicchio, C., et al., "Synthesis of α-amino acid derivatives by copper(I)-catalyzed conjugate addition of grignard reagents to methyl 2-acetamidoacrylate," Tetrahedron Lett 26(36):4387-4390 Pergamon Press, United Kingdom (May 1985).
Chatterjee, B., et al., "Selective α-Deuteration of Amines and Amino Acids Using D2O," Org Lett 18(22):5892-5895, American Chemical Society, United States (Nov. 2016).
Davies, S.G., et al., "Asymmetric conjugate reductions with samarium diiodide: asymmetric synthesis of (2S,3R)- and (2S,3S)-[2-2H,3-2H]-leucine-(S)-phenylalanine dipeptides and (2S,3R)-[2-(2)H,3-2H]-phenylalanine methyl ester," Org Biomol Chem 3(8):1435-1447, Royal Society of Chemistry, United Kingdom (Apr. 2005).
Dyson, G., et al., "The mechanism of action of medicinal substances," in *Chemistry of Synthetic Drugs*, pp. 12-19, Mir Publishers, Moscow, Union of Soviet Socialist Republics (1964).
Fletcher, M.D., et al., "Three approaches to the synthesis of L-leucine selectively labelled with carbon-13 or deuterium in either diastereotopic methyl group ," J Chem Soc, Perkin Trans 1, 43-52, Royal Society of Chemistry, United Kingdom (Jan. 2000).
Giese, A.K., et al., "A novel, highly sensitive and specific biomarker for Niemann-Pick type C1 disease," Orphanet J Rare Dis 10:78, BioMed Central, United Kingdom (Jun. 2015).
Hill, R.K., et al., "Synthesis of (2S,4S)- and (2S,4R)-[5,5,5-2H3] leucine from (R)-pulegone," Can J Chem 72(1):110-113 NRC Research Press, Canada (Jan. 1994).
Homer, R.J., et al., "The use of cystathionine gamma-synthase in the production of alpha and chiral beta deuterated amino acids," Anal Biochem 215(2):211-215, Elsevier, Netherlands (Dec. 1993).
International Search Report and Written Opinion for International Application No. PCT/IB2019/060525, European Patent Office, Netherlands, mailed on Feb. 3, 2020, 14 pages.
Kelly, N., et al., "Methods for the Synthesis of L-Leucine Selectively Labelled with Carbon-13 or Deuterium in either Diastereotopic Methyl Group," Tetrahedron Lett 36:8315-8318, Elsevier, Netherlands (Nov. 1995).
Kelly, N., et al., "Chemo-enzymatic synthesis of isotopically labelled L-Valine, L-Isoleucine and allo-isoleucine," Tetrahedron Lett 37(9):1517-1520 Elsevier, Netherlands (Feb. 1996).
Kelly, N.M., et al., "Syntheses of amino acids incorporating stable isotopes," Nat Prod Rep 14:205-219, Royal Society of Chemistry, United Kingdom (Jan. 1997).
Kümmerer, K., "Pharmaceuticals in the environment," Annu Rev Environ Resour 35:57-75, Annual Reviews, United States (Aug. 2010).
Miyanoiri, Y., et al., "Differential isotope-labeling for Leu and Val residues in a protein by *E. coli* cellular expression using stereospecifically methyl labeled amino acids," J Biomol NMR 57(3):237-249, Springer Nature, Germany (Nov. 2013).
Moss, G.P., "Basic Terminology of Stereochemistry," Pure & Appl Chem 68(12):2193-2222, International Union of Pure and Applied Chemistry, Great Britain (1996).

(56) References Cited

OTHER PUBLICATIONS

Nakajima, et al., "Enzymatic conversion of racemic methionine to the L-enantiomer," J Chem Soc, Chem Commun 13:947-948, Royal Society of Chemistry, United Kingdom (1990).

Oba, M., et al., "Synthesis of L-threo- and L-erythro-[1-13C, 2,3-2H2]amino acids: novel probes for conformational analysis of peptide side chains" J Chem Soc, Perkin Trans 1 12:1603-1609, Royal Society of Chemistry, United Kingdom (1995).

Oba, M., et al., "Stereoselective deuterium-labelling of diastereotopic methyl and methylene protons of L-leucine," Tetrahedron Lett 39:1595-1598 Elsevier, Netherlands (Mar. 1998).

Oba, M., et al., "Synthesis of (13)C/D doubly labeled L-leucines: probes for conformational analysis of the leucine side-chain," J Org Chem 66(17):5919-5922, American Chemical Society, United States (Aug. 2001).

Patterson, M.C., et al., "Miglustat for treatment of Niemann-Pick C disease: a randomised controlled study," Lancet Neurol 6(9):765-772, Elsevier, Netherlands (Sep. 2007).

Rose, J.E., et al., "Stereospecific synthesis of α-deuteriated α-amino acids: regiospecific deuteriation of chiral 3-isopropyl-2,5-dimethoxy-3,6-dihydropyrazines," J Chem Soc, Perkin Trans 1, 2:157-165 Royal Society of Chemistry, United Kingdom (1995).

Schniepp, R,, et al., "Acetyl-DL-leucine improves gait variability in patients with cerebellar ataxia-a case series," Cerebellum Ataxias 3:8, BioMed Central, United Kingdom (Apr. 2016).

Shah, S.A., et al., "Enantiomeric conversion of racemic amino acid mixtures via an oxidase-aminotransferase coupled system," Tetrahedron Lett 35:29-32, Elsevier, Netherlands (Jan. 1994).

Shao, L., et al., "The kinetic isotope effect in the search for deuterated drugs," Drug News Perspect 23(6)398-404, Thomson Reuters, Canada (Jul.-Aug. 2010).

Te Vruchte, D., et al., "Relative acidic compartment vol. as a lysosomal storage disorder-associated biomarker," J Clin Invest 124(3):1320-1328, American Society for Clinical Investigation, United States (Mar. 2014).

Timmins, G.S., "Deuterated drugs: where are we now?" Expert Opin Ther Pat 24(10):1067-1075, Informa, United Kingdom (Oct. 2014).

Upson, D.A., and Hruby, V.J., "A general method for the preparation of alpha-labeled amino acids," J Org Chem 42(13):2329-2330, American Chemical Society, United States (Jun. 1977).

Van Tonder, E.C., et al., "Preparation and physicochemical characterization of 5 niclosamide solvates and 1 hemisolvate," AAPS PharmSciTech 5(1):E12, Springer Nature, Germany (Feb. 2004).

Yamauchi, N., and Endoh, S., "Improved isotopic deuterium labeling at the diastereotopic methyl group of leucine: a synthetic route to (4S)- and (4R)-[5-2H1]leucine," Biosci Biotechnol Biochem 70(1):276-278, Oxford University Press, United Kingdom (Jan. 2006).

Yuan, S.S., and Ajami, A.M., "Trideuteromethyl labeled leucine and valine," Hua Xue—Chemistry 49(4):257-260, Zhongguo Huaxuehui, Taiwan (Dec. 1991).

English language translation of Office Action for Russian Patent Application No. 2021119633, dated May 22, 2023, Federal Service for Intellectual Property, Moscow, Russia, 6 pages.

Kinney, C.R., and Adams, R., "Dideuteriovaline and Dideuterioleucine," J Am Chem Soc 59(5):897-898, American Chemical Society, United States (May 1937).

Timmins, G.S., "Deuterated drugs: where are we now?" Expert Opin Ther Pat 24(10):1067-1075, Taylor & Francis, United Kingdom (Oct. 2014).

Office Action mailed Oct. 6, 2022, in U.S. Appl. No. 17/247,757, Factor, M., et al., filed Dec. 22, 2020, 14 pages.

Office Action mailed May 5, 2023, in U.S. Appl. No. 17/247,757, Factor, M., et al., filed Dec. 22, 2020, 17 pages.

Office Action mailed Oct. 4, 2023, in U.S. Appl. No. 17/247,757, Factor, M., et al., filed Dec. 22, 2020, 16 pages.

Notice of Allowance mailed Apr. 10, 2024 in U.S. Appl. No. 17/247,757, Factor, M., et al., filed Dec. 22, 2020, 13 pages.

\* cited by examiner

DEUTERATED ANALOGS OF ACETYL-LEUCINE

BACKGROUND OF THE INVENTION

Field of Invention

The present disclosure provides deuterated DL-, D-, and L-N-acetyl leucine analogs, and pharmaceutically acceptable salts and solvates thereof, and deuterated DL-, D-, and L-N-acetyl leucine alkyl ester analogs, and pharmaceutically acceptable salts and solvates thereof. The present disclosure also provides methods of treating or delaying the progression of a lysosomal storage disorder, methods of providing neuroprotection in a subject having a lysosomal disorder, methods of treating or delaying the progression of a neurodegenerative disease in a subject, treating or delaying the progression of a neurodegenerative disease associated with defects in lysosomal storage in a subject, treating or preventing a migraine in a subject, and the symptoms associated therewith, treating or preventing restless legs syndrome, and the symptoms associated therewith, treating or preventing vertigo, and the symptoms associated therewith, or improving mobility and/or cognitive function in a subject, comprising administering deuterated N-acetyl leucine analogs, and pharmaceutically acceptable salts and solvates thereof, or deuterated N-acetyl leucine alkyl ester analogs, and pharmaceutically acceptable salts and solvates thereof, to the subject.

Background

Neurodegenerative diseases affect neurons, and the degenerative process can involve the progressive loss of neuronal structure, the progressive loss of neuronal function, or progressive neuron cell death. Neurodegenerative diseases are frequently associated with defects in lysosomal storage. This includes both the neurodegenerative lysosomal storage disorders and many common neurodegenerative diseases, such as Alzheimer's disease and Parkinson's disease, where links to lysosomal defects have been suggested. Therapeutic agents that are broadly neuroprotective would apply to neurodegenerative diseases generally, including those caused by an underlying lysosomal storage disorder and those caused by other processes.

Lysosomal storage disorders (LSDs) are a group of inherited metabolic diseases caused by defects in lysosomal homeostasis. LSDs encompass over 70 diseases, with a collective clinical frequency of 1:5000 live births. These diseases can be classified into two main groups: primary storage disorders resulting from a direct deficiency in degradation pathways (typically lysosomal enzyme deficiency disorders) and secondary storage disorders which are caused by malfunctioning downstream lysosomal proteins. Distinct LSDs that result from the inactivation of different lysosomal proteins often share similar pathologies. In most cases, multiple organs and tissues are involved. Region-specific neurodegeneration is featured in the majority of these diseases.

Migraines are characterized by recurrent moderate to severe headaches. Typically, the headaches affect one half of the head, are pulsating in nature, and last from 2 to 72 hours. Symptoms of migraine include nausea, vomiting, and sensitivity to light, sound or smell. The pain is often accentuated by physical activity. About 15% of the world's population is affected by migraines.

The changes that occur with ageing can lead to problems with a person's ability to move around. Mobility problems may include unsteadiness while walking, difficulty getting in and out of a chair, or falls. Muscle weakness, joint problems, pain, disease and neurological (brain and nervous system) difficulties—common conditions in older people—can all contribute to mobility problems. Sometimes several mild problems occur at one time and combine to seriously affect mobility.

In addition to potential mobility problems, all ageing humans will develop some degree of decline in cognitive capacity, symptoms often including forgetfulness, decreased ability to maintain focus, decreased problem-solving capacity and/or reduced spatial awareness. Symptoms can progress into more serious conditions, such as dementia and depression, or even Alzheimer's disease.

Many factors are believed to contribute to age-related cognitive decline, including oxidative stress and free radical damage, declining hormone levels (like estrogen, testosterone, DHEA and pregnenolone), inner arterial lining (endothelium) dysfunction, insulin resistance, excess body weight, suboptimal nutrition, loneliness, lack of social network and high stress, among other things Current therapeutic approaches to treat neurodegenerative diseases, LSDs, and migraines, and to improve mobility and/or cognitive function are limited. For example, some LSDs have been responsive to bone marrow transplantation or enzyme replacement therapy. Some benefit has also been reported in a clinical trial of substrate reduction therapy (SRT) using an inhibitor of glycosphingolipid (GSL) biosynthesis: the imino sugar drug, miglustat. Patterson, et al., *Rev Neurol (separata)* 43:8 (2006). Benefit has also been reported using acetyl-DL-leucine in case studies of patients with cerebellar ataxia (showing improved gait variability) and Niemann-Pick Type C (NPC) (showing improvement in ataxia). See Schniepp, R., et al., *Cerebellum & Ataxias* 3:8 (2016); Bremova, T., et al., *Neurology* 85:1368 (2015).

Despite the beneficial effects of N-acetyl leucine there remains a need for improved treatments of LSDs. There is also a need to develop improved treatments of neurodegenerative diseases, neurodegenerative diseases associated with defects in lysosomal storage, migraines, restless legs syndrome, and vertigo. There is also a need to develop improved treatments for improving mobility and/or cognitive function.

BRIEF SUMMARY OF THE INVENTION

In one aspect, the disclosure provides deuterated N-acetyl leucine analogs, and the pharmaceutically acceptable salts and solvates thereof, and deuterated N-acetyl leucine alkyl ester analogs, and the pharmaceutically acceptable salts and solvates thereof, represented by any one of Formulae I-V, below, collectively referred to herein as "Compounds of the Disclosure." Compounds of the Disclosure are enriched with least one deuterium atom in an abundance that is at least 1000 times greater than the natural abundance of deuterium.

In another aspect, the disclosure provides a method of treating or delaying the progression of a LSD the method comprising administering to a subject in need thereof a therapeutically effective amount of a Compound of the Disclosure.

In another aspect, the disclosure provides a method of providing neuroprotection in a subject having a LSD, the method comprising administering to a subject in need thereof a therapeutically effective amount of a Compound of the Disclosure.

In another aspect, the disclosure provides a method of treating or delaying the progression of a neurodegenerative disease or a neurodegenerative disease associated with defects in lysosomal storage, the method comprising administering to a subject in need thereof a therapeutically effective amount of a Compound of the Disclosure.

In another aspect, the disclosure provides a method of treating or preventing a migraine, and the symptoms associated therewith, the method comprising administering to a subject in need thereof a therapeutically effective amount of a Compound of the Disclosure.

In another aspect, the disclosure provides a method of improving mobility and/or cognitive function, the method comprising administering to a subject in need thereof a therapeutically effective amount of a Compound of the Disclosure.

In another aspect, the disclosure provides a method of treating or preventing restless legs syndrome, and the symptoms associated therewith, the method comprising administering to a subject in need thereof a therapeutically effective amount of a Compound of the Disclosure.

In another aspect, the disclosure provides a method of treating or preventing vertigo, and the symptoms associated therewith, the method comprising administering to a subject in need thereof a therapeutically effective amount of a Compound of the Disclosure.

In another aspect, the present disclosure provides a pharmaceutical composition comprising a Compound of the Disclosure and an excipient and/or pharmaceutically acceptable carrier.

In another aspect, the present disclosure provides a pharmaceutical composition comprising a Compound of the Disclosure and an excipient and/or pharmaceutically acceptable carrier for use in treating or delaying the progression of a LSD in a subject.

In another aspect, the present disclosure provides a pharmaceutical composition comprising a Compound of the Disclosure and an excipient and/or pharmaceutically acceptable carrier for use in providing neuroprotection in a subject having a LSD.

In another aspect, the present disclosure provides a pharmaceutical composition comprising a Compound of the Disclosure and an excipient and/or pharmaceutically acceptable carrier for use in treating or delaying the progression of a neurodegenerative disease or a neurodegenerative disease associated with defects in lysosomal storage in a subject.

In another aspect, the present disclosure provides a pharmaceutical composition comprising a Compound of the Disclosure and an excipient and/or pharmaceutically acceptable carrier for use in treating or preventing a migraine, and the symptoms associated therewith, in a subject.

In another aspect, the present disclosure provides a pharmaceutical composition comprising a Compound of the Disclosure and an excipient and/or pharmaceutically acceptable carrier for use in improving mobility and/or cognitive function in a subject.

In another aspect, the disclosure provides a pharmaceutical composition comprising a Compound of the Disclosure and an excipient and/or pharmaceutically acceptable carrier for use in treating or preventing restless legs syndrome, and the symptoms associated therewith, in a subject.

In another aspect, the disclosure provides a pharmaceutical composition comprising a Compound of the Disclosure and an excipient and/or pharmaceutically acceptable carrier for use in treating or preventing vertigo, and the symptoms associated therewith, in a subject.

In another aspect, the present disclosure provides a Compound of the Disclosure for use in treating or delaying the progression of a LSD in a subject.

In another aspect, the present disclosure provides a Compound of the Disclosure for use in providing neuroprotection in a subject having a LSD.

In another aspect, the present disclosure provides a Compound of the Disclosure for use in treating or delaying the progression of a neurodegenerative disease or a neurodegenerative disease associated with defects in lysosomal storage in a subject.

In another aspect, the present disclosure provides a Compound of the Disclosure for use in treating or preventing a migraine, and the symptoms associated therewith, in a subject.

In another aspect, the present disclosure provides a Compound of the Disclosure for use in improving mobility and/or cognitive function in a subject.

In another aspect, the present disclosure provides a Compound of the Disclosure for use in treating or preventing restless legs syndrome, and the symptoms associated therewith, in a subject.

In another aspect, the present disclosure provides a Compound of the Disclosure for use in treating or preventing vertigo, and the symptoms associated therewith, in a subject.

In another aspect, the present disclosure provides a use of a Compound of the Disclosure for the manufacture of a medicament for treating or delaying the progression of a LSD in a subject.

In another aspect, the present disclosure provides a use of a Compound of the Disclosure for the manufacture of a medicament for providing neuroprotection in a subject having a LSD.

In another aspect, the present disclosure provides a use of a Compound of the Disclosure for the manufacture of a medicament for treating or delaying the progression of a neurodegenerative disease or a neurodegenerative disease associated with defects in lysosomal storage in a subject.

In another aspect, the present disclosure provides a use of a Compound of the Disclosure for the manufacture of a medicament for treating or preventing a migraine, and the symptoms associated therewith, in a subject.

In another aspect, the present disclosure provides a use of a Compound of the Disclosure for the manufacture of a medicament for improving mobility and/or cognitive function in a subject.

In another aspect, the present disclosure provides a use of a Compound of the Disclosure for the manufacture of a medicament for treating or preventing restless legs syndrome, and the symptoms associated therewith, in a subject.

In another aspect, the present disclosure provides a use of a Compound of the Disclosure for the manufacture of a medicament for treating or preventing vertigo, and the symptoms associated therewith, in a subject.

In another aspect, the present disclosure provides kits comprising a Compound of the Disclosure, and, optionally, a package insert containing directions for use in the treatment of a LSD, a neurodegenerative disease, or a neurodegenerative disease associated with defects in lysosomal storage in a subject.

In another aspect, the present disclosure provides kits comprising a Compound of the Disclosure, and, optionally, a package insert containing directions for use in treating or preventing a migraine, and the symptoms associated therewith, in a subject.

In another aspect, the present disclosure provides kits comprising a Compound of the Disclosure, and, optionally, a package insert containing directions for use in improving mobility and/or cognitive function in a subject.

In another aspect, the present disclosure provides kits comprising a Compound of the Disclosure, and, optionally, a package insert containing directions for use in treating or preventing restless legs syndrome, and the symptoms associated therewith, in a subject.

In another aspect, the present disclosure provides kits comprising a Compound of the Disclosure, and, optionally, a package insert containing directions for use in treating or preventing vertigo, and the symptoms associated therewith, in a subject.

In another embodiment, the disclosure provides procedures of personalized medicine for subjects having a LSD or a neurodegenerative disease, and encompasses the selection of treatment options with the highest likelihood of successful outcome for individual LSD or neurodegenerative subjects.

In another embodiment, the disclosure provides procedures of personalized medicine for subjects having a migraine, and the symptoms associated therewith, and encompasses the selection of treatment options with the highest likelihood of successful outcome for treating or preventing a migraine, and the symptoms associated therewith, in a subject.

In another embodiment, the disclosure provides procedures of personalized medicine for subjects in need of improving mobility and/or cognitive function, and encompasses the selection of treatment options with the highest likelihood of successful outcome for improving mobility and/or cognitive function in a subject.

In another aspect, the present disclosure provides methods of preparing Compounds of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Figure 1:
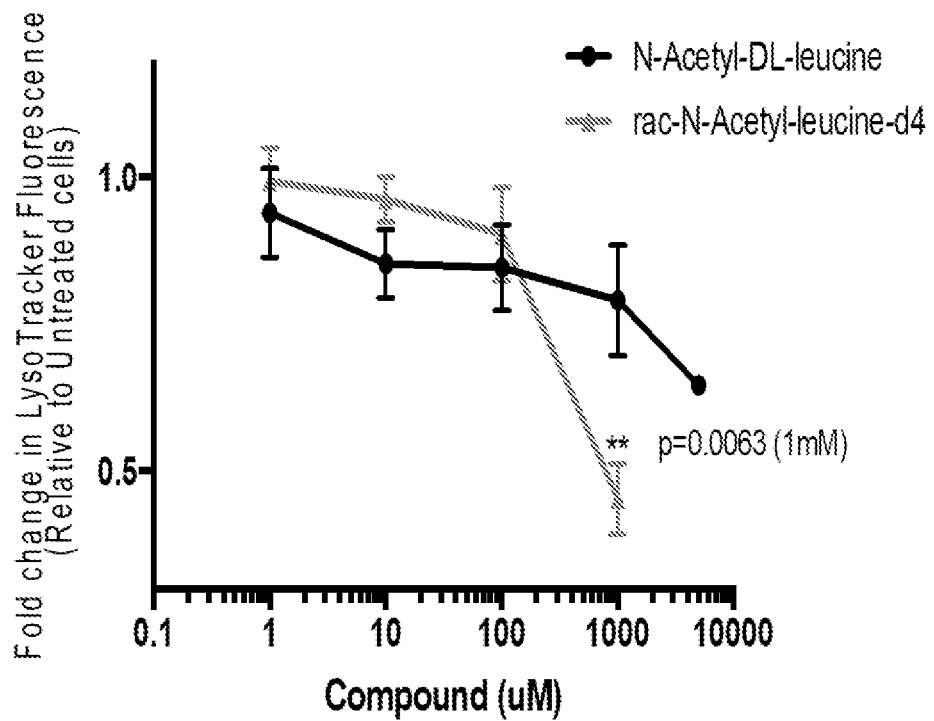
FIG. 1 is a line graph showing the effect of acetyl-leucine (referred to as IB1000) and acetyl-leucine-2,3,3,4-$d_4$ (referred to as DIB1000) in a NPC cellular phenotype assay. NPC CHO cells were treated with 1, 10, 100, 1000, and 5000 µM of acetyl-leucine or acetyl-leucine-2,3,3,4-$d_4$ for 7 days. Data shown is Mean±SD of 1-3 biological repeats. LysoTracker fluorescence is expressed as fold change relative to responses obtained from untreated samples (normalised as 1.0). Acetyl-leucine; 0.79±0.05, Acetyl-leucine-2,3,3,4-$d_4$; 0.45±0.03, unpaired t test, Two-tailed test, **$p<0.01$, n=3.

Compounds of the Disclosure can be used to treat or delay the progression of a LSD in a subject, provide neuroprotection in a subject having a LSD, treat or delay the progression of a neurodegenerative disease, treat or delay the progression a neurodegenerative disease associated with defects in lysosomal storage in a subject, treat or prevent a migraine, and the symptoms associated therewith, in a subject, treat or prevent restless legs syndrome, and the symptoms associated therewith, in a subject, treat or prevent vertigo, and the symptoms associated therewith, in a subject, or for improving mobility and/or cognitive function in a subject.

In one embodiment, Compounds of the Disclosure are compounds having Formula I:

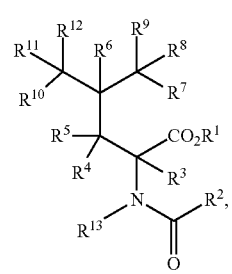

or a pharmaceutically acceptable salt or solvate thereof, wherein:

$R^1$ is selected from the group consisting of hydrogen and $C_{1-6}$ alkyl;

$R^2$ is $C_{1-6}$ alkyl; and $R^3$, $R^4$, $R^5$, $R^6$, $R^7$, $R^8$, $R^9$, $R^{10}$, $R^{11}$, $R^{12}$, and $R^{13}$ are each independently selected from the group consisting of hydrogen and deuterium, wherein the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more.

In another embodiment, Compounds of the Disclosure are compounds having Formula I, or a pharmaceutically acceptable salt or solvate thereof, wherein:

(a) at least one of $R^3$, $R^4$, $R^5$, $R^6$, $R^7$, $R^8$, $R^9$, $R^{10}$, $R^{11}$, and $R^{12}$ is hydrogen when $R^{13}$ is hydrogen; and (b) and the compound is not:

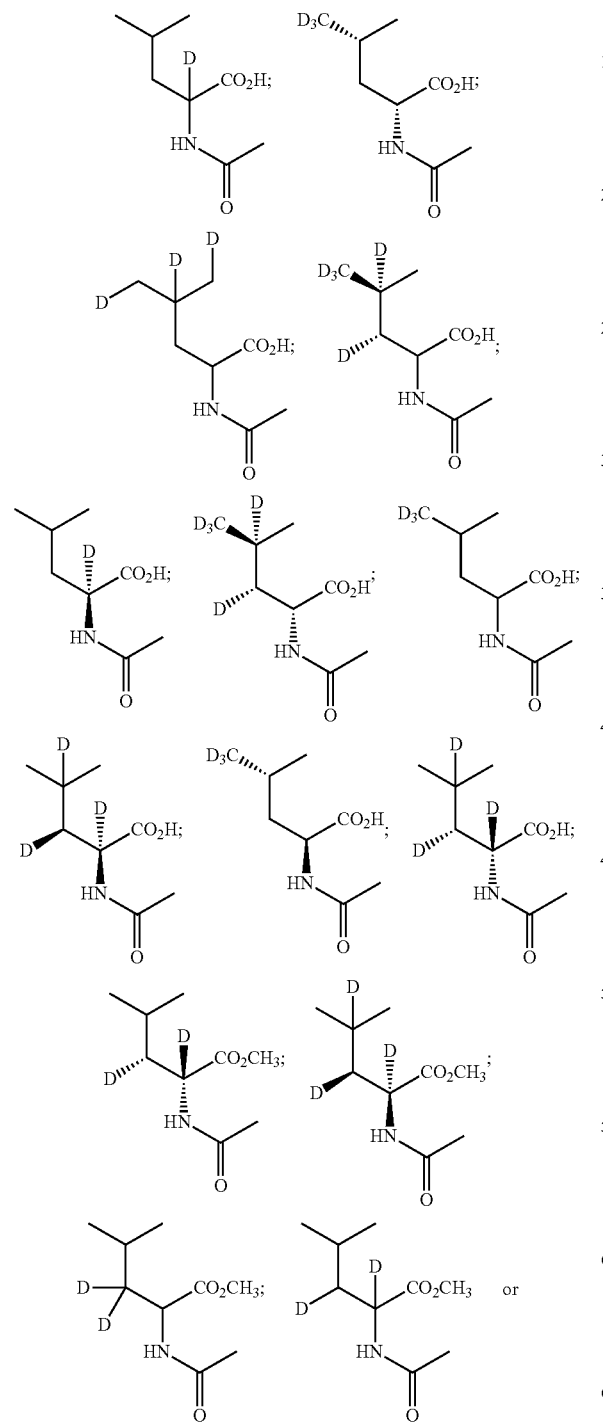

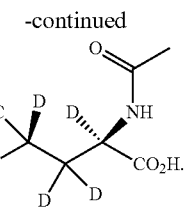

In another embodiment, Compounds of the Disclosure are optically inactive compounds having Formula I, or a pharmaceutically acceptable salt or solvate thereof, i.e., the compound is racemic.

In another embodiment, Compounds of the Disclosure are optically active compounds having Formula I, or a pharmaceutically acceptable salt or solvate thereof.

In another embodiment, Compounds of the Disclosure are compounds having Formula II:

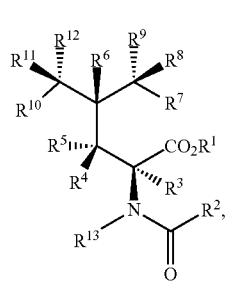

II or a pharmaceutically acceptable salt or solvate thereof, wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined in connection with Formula I.

In another embodiment, Compounds of the Disclosure are compounds having Formula III:

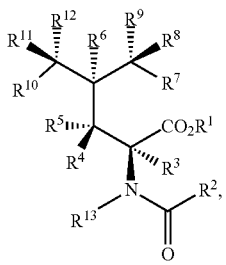

III or a pharmaceutically acceptable salt or solvate thereof, wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined in connection with Formula I.

In another embodiment, Compounds of the Disclosure are compounds having Formula IV:

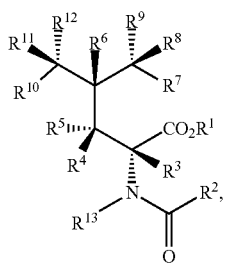

IV or a pharmaceutically acceptable salt or solvate thereof, wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined in connection with Formula I.

In another embodiment, Compounds of the Disclosure are compounds having Formula V:

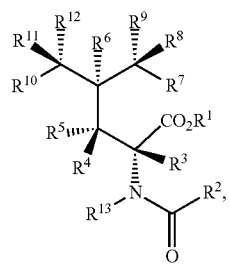

V or a pharmaceutically acceptable salt or solvate thereof, wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined in connection with Formula I.

In another embodiment, Compounds of the Disclosure are compounds having any one of Formulae I-V, or a pharmaceutically acceptable salt or solvate thereof, having an enantiomeric excess (ee) of about 50% or more. In another embodiment, the ee is about 55% or more, about 60% or more, about 65% or more, about 70% or more, about 75% or more, about 80% or more, about 85% or more, about 90% or more, about 95% or more, about 98% or more, or about 99% or more. In another embodiment, the ee is about 100%.

In another embodiment, Compounds of the Disclosure are compounds having any one of Formulae I-V, or a pharmaceutically acceptable salt or solvate thereof, wherein $R^1$ is hydrogen.

In another embodiment, Compounds of the Disclosure are compounds having any one of Formulae I-V, or a pharmaceutically acceptable salt or solvate thereof, wherein $R^2$ is methyl.

In another embodiment, Compounds of the Disclosure are compounds having any one of Formulae I-V, or a pharmaceutically acceptable salt or solvate thereof, wherein $R^{13}$ is hydrogen.

In another embodiment, Compounds of the Disclosure are compounds having any one of Formulae I-V, or a pharmaceutically acceptable salt or solvate thereof, wherein the deuterium enrichment of any two or more of $R^3$, $R^4$, $R^5$, $R^6$, $R^7$, $R^8$, $R^9$, $R^{10}$, $R^{11}$, and $R^{12}$ is about 15% or more.

In another embodiment, Compounds of the Disclosure are compounds having any one of Formulae I-V, or a pharmaceutically acceptable salt or solvate thereof, wherein the deuterium enrichment of any three or more of $R^3$, $R^4$, $R^5$, $R^6$, $R^7$, $R^8$, $R^9$, $R^{10}$, $R^{11}$, and $R^{12}$ is about 15% or more.

In another embodiment, Compounds of the Disclosure are compounds having any one of Formulae I-V, or a pharmaceutically acceptable salt or solvate thereof, wherein the deuterium enrichment of any four or more of $R^3$, $R^4$, $R^5$, $R^6$, $R^7$, $R^8$, $R^9$, $R^{10}$, $R^{11}$, and $R^{12}$ is about 15% or more.

In another embodiment, Compounds of the Disclosure are compounds having any one of Formulae I-V, or a pharmaceutically acceptable salt or solvate thereof, wherein the deuterium enrichment of any five or more of $R^3$, $R^4$, $R^5$, $R^6$, $R^7$, $R^8$, $R^9$, $R^{10}$, $R^{11}$, and $R^{12}$ is about 15% or more.

In another embodiment, Compounds of the Disclosure are compounds having any one of Formulae I-V, or a pharmaceutically acceptable salt or solvate thereof, wherein the deuterium enrichment of any six or more of $R^3$, $R^4$, $R^5$, $R^6$, $R^7$, $R^8$, $R^9$, $R^{10}$, $R^{11}$, and $R^{12}$ is about 15% or more.

In another embodiment, Compounds of the Disclosure are compounds having any one of Formulae I-V, or a pharmaceutically acceptable salt or solvate thereof, wherein the deuterium enrichment of any seven or more of $R^3$, $R^4$, $R^5$, $R^6$, $R^7$, $R^8$, $R^9$, $R^{10}$, $R^{11}$, and $R^{12}$ is about 15% or more.

In another embodiment, Compounds of the Disclosure are compounds having any one of Formulae I-V, or a pharmaceutically acceptable salt or solvate thereof, wherein the deuterium enrichment of any eight or more of $R^3$, $R^4$, $R^5$, $R^6$, $R^7$, $R^8$, $R^9$, $R^{10}$, $R^{11}$, and $R^{12}$ is about 15% or more.

In another embodiment, Compounds of the Disclosure are compounds having any one of Formulae I-V, or a pharmaceutically acceptable salt or solvate thereof, wherein:

the deuterium enrichment of $R^7$ is about 15% or more;

the deuterium enrichment of $R^{10}$ is about 15% or more; and $R^6$, $R^8$, $R^9$, $R^{11}$, and $R^{12}$ are hydrogen.

In another embodiment, Compounds of the Disclosure are compounds having any one of Formulae I-V, or a pharmaceutically acceptable salt or solvate thereof, wherein:

the deuterium enrichment of $R^7$ and $R^8$ is about 15% or more;

the deuterium enrichment of $R^{10}$ and $R^{11}$ is about 15% or more; and $R^9$ and $R^{12}$ are hydrogen.

In another embodiment, Compounds of the Disclosure are compounds selected from the group consisting of:

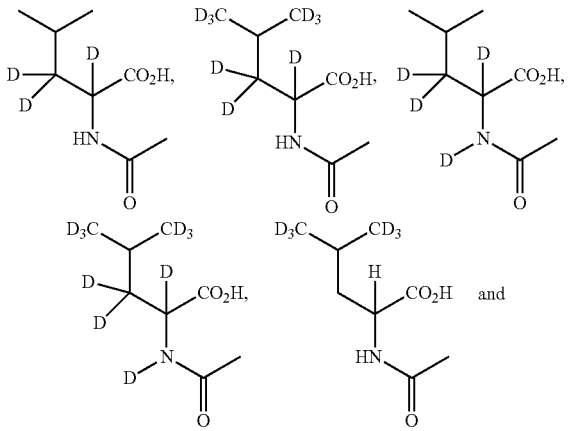

-continued

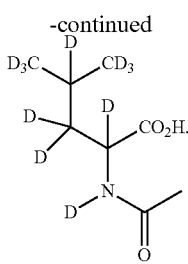

or a pharmaceutically acceptable salt or solvate thereof.

In another embodiment, Compounds of the Disclosure are compounds selected from the group consisting of:

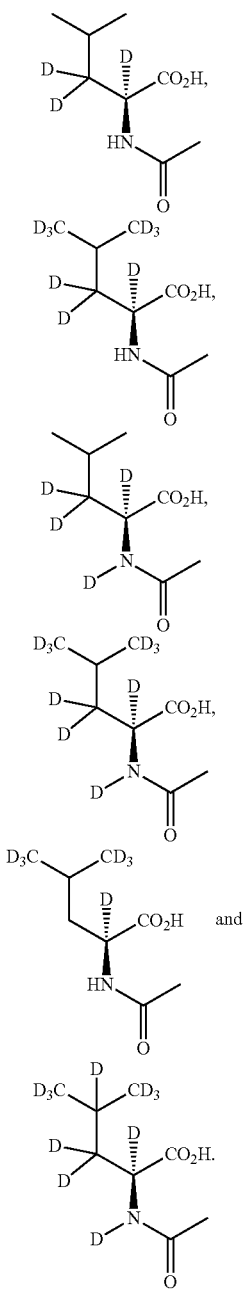

or a pharmaceutically acceptable salt or solvate thereof.

In another embodiment, Compounds of the Disclosure are compounds selected from the group consisting of:

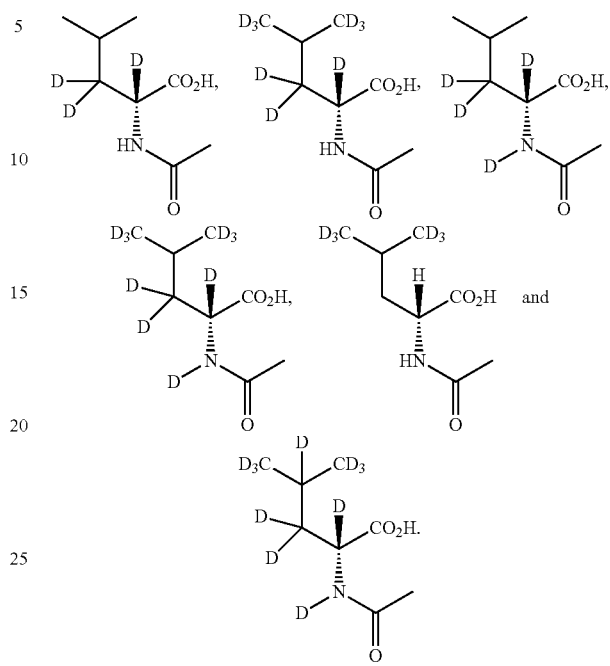

or a pharmaceutically acceptable salt or solvate thereof.

In another embodiment, Compounds of the Disclosure are compounds selected from the group consisting of:

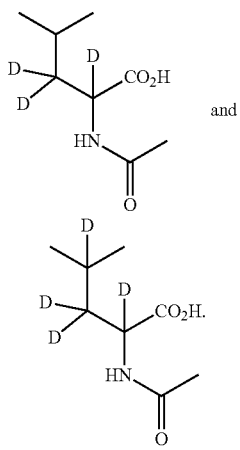

In another embodiment, Compounds of the Disclosure are compounds selected from the group consisting of:

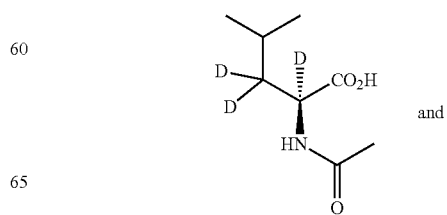

-continued

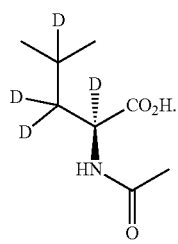

In another embodiment, Compounds of the Disclosure are compounds selected from the group consisting of:

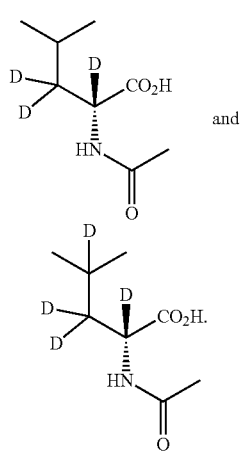

In another embodiment, the Compound of the Disclosure is:

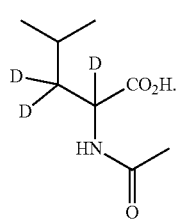

In another embodiment, the Compound of the Disclosure is:

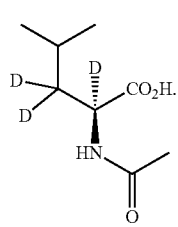

In another embodiment, the Compound of the Disclosure is:

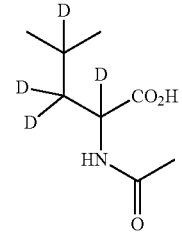

In another embodiment, the Compound of the Disclosure is:

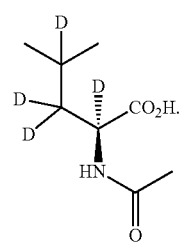

The term "N-acetyl-DL-leucine" or "aceyl-leucine" refers to a compound having the following structure:

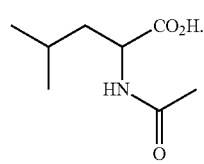

The term "N-acetyl-D-leucine" or "aceyl-D-leucine" refers to a compound having the following structure:

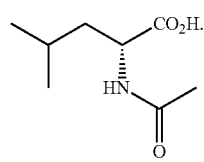

The term "N-acetyl-L-leucine" or "aceyl-L-leucine" refers to a compound having the following structure:

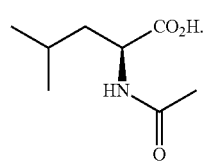

The term "$C_{1-6}$ alkyl" as used herein refers to a straight- or branched-chain aliphatic hydrocarbon containing one to six carbon atoms In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{3-4}$ alkyl group. The term $C_{1-6}$ alkyl includes analogs having at least one deuterium in place of hydrogen at an abundance that is at least about 1000 times greater than the natural abundance of deuterium. Non-limiting exemplary $C_{1-6}$ alkyl groups include methyl, —$CH_2D$, —$CHD_2$, —$CD_3$, ethyl, propyl, isopropyl, butyl, sec-butyl, tert-butyl, iso-butyl, 3-pentyl, and hexyl.

When a position of any one of Formulae I-V is designated specifically as "H" or "hydrogen," the position is understood to have hydrogen at its natural abundance isotopic composition.

When a position of any one of Formulae I-V is designated specifically as "D" or "deuterium," the position is understood to have deuterium at an abundance that is at least about 1000 times greater than the natural abundance of deuterium, which is about 0.015%.

The term "deuterium enrichment" as used herein refers to the percentage of incorporation of deuterium at a given position of any one of Formulae I-V in place of hydrogen at that position. In one embodiment, the deuterium enrichment is about 15% or more, i.e., at least about 1000 times greater than the natural abundance of deuterium. In another embodiment, the deuterium enrichment is about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 98% or more, or about 99% or more. In another embodiment, the deuterium enrichment is about 100%. The deuterium enrichment can be determined using conventional analytical methods known to one of ordinary skill in the art, including mass spectrometry and nuclear magnetic resonance spectroscopy.

As used herein, the term "stereoisomers" is a general term for all isomers of an individual molecule that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in Pure & Appl. Chem (55:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography, or optical polarimetry.

Salts and solvates, e.g., hydrates, of the Compounds of the Disclosure can also be used in the methods disclosed herein.

The present disclosure encompasses the preparation and use of salts of Compounds of the Disclosure. As used herein, a "pharmaceutically acceptable salt" refers to salts or zwitterionic forms of Compounds of the Disclosure. Salts of Compounds of the Disclosure can be prepared during the final isolation and purification of the compounds or separately by reacting the compound with an acid having a suitable cation. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to Compounds of the Disclosure appearing herein is intended to include Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g., a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure.

One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by van Tonder et al., *AAPS Pharm. Sci. Tech.,* 5(7):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

Pharmaceutical Compositions

In another embodiment, the disclosure provides a pharmaceutical composition comprising a Compound of the Disclosure, or a pharmaceutically acceptable salt or solvate thereof, and a pharmaceutically acceptable carrier and/or excipient.

Compounds of the Disclosure typically are administered in admixture with a pharmaceutical excipient selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compounds of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, e.g., from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, e.g., about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A composition for intravenous, cutaneous, or subcutaneous injection typically contains an isotonic vehicle.

Compounds of the Disclosure can be readily combined with pharmaceutically acceptable carriers and excipients well-known in the art. Standard pharmaceutical carriers and excipients are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a subject to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In one embodiment, the pharmaceutically acceptable carrier is a solid, and the composition is in the form of a powder or tablet. A solid pharmaceutically acceptable carrier may include one or more substances which may also act as flavouring agents, buffers, lubricants, stabilisers, solubilisers, suspending agents, wetting agents, emulsifiers, dyes, fillers, glidants, compression aids, inert binders, sweeteners, preservatives, dyes, coatings, or tablet-disintegrating agents. The carrier may also be an encapsulating material. In powders, the carrier is a finely divided solid that is in admixture with the finely divided active agents according to the invention. In tablets, the active agent may be mixed with a carrier having the necessary compression properties in suitable proportions and compacted in the shape and size desired. The powders and tablets may contain up to 99% of the active agents. Suitable solid carriers include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutically acceptable carrier may be a gel and the composition may be in the form of a cream or the like.

The carrier may include one or more excipients or diluents. Examples of such excipients are gelatin, gum *arabicum*, lactose, microcrystalline cellulose, starch, sodium starch glycolate, calcium hydrogen phosphate, magnesium stearate, talcum, colloidal silicon dioxide and the like.

In another embodiment, the pharmaceutically acceptable carrier is a liquid, and the pharmaceutical composition is in the form of a solution. Liquid carriers are used in preparing solutions, suspensions, emulsions, syrups, elixirs and pressurized compositions. A Compound of the Disclosure may be dissolved or suspended in a pharmaceutically acceptable liquid carrier such as water, an organic solvent, a mixture of both or pharmaceutically acceptable oils or fats. The liquid carrier may contain other suitable pharmaceutical additives such as solubilisers, emulsifiers, buffers, preservatives, sweeteners, flavouring agents, suspending agents, thickening agents, colors, viscosity regulators, stabilizers or osmoregulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The active agent may be prepared as a sterile solid composition that may be dissolved or suspended at the time of administration using sterile water, saline, or other appropriate sterile injectable medium.

The Compounds of the Disclosure and their compositions may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

Compounds of the Disclosure and their compositions can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Compounds of the Disclosure and their compositions may alternatively be administered by inhalation (e.g. intranasally). Compositions may also be formulated for topical use. For instance, creams or ointments may be applied to the skin.

Compounds of the Disclosure and their compositions may be incorporated within a slow- or delayed-release device. Such devices may, for example, be inserted on or under the skin, and the medicament may be released over weeks or even months. Such devices may be particularly advantageous when long-term treatment with a Compound of the Disclosure is required and which would normally require frequent administration (e.g. at least daily administration).

In another embodiment, the pharmaceutical composition is in the form of a tablet suitable for oral administration. In tablets, the Compound of the Disclosure may be mixed with a vehicle having the necessary compression properties in suitable proportions and compacted in the shape and size desired. The tablets may contain up to 99% by weight of the Compound of the Disclosure.

Pharmaceutical formulations in solid oral dosage form, such as tablets, may be prepared by any method known in the art of pharmacy. Pharmaceutical formulations are usually prepared by mixing a Compound of the Disclosure, or a pharmaceutically acceptable salt thereof, with conventional pharmaceutically acceptable carriers, diluents or excipients.

Methods of Use

In another embodiment, the disclosure provides a method of treating or delaying the progression of a lysosomal storage disorder, the method comprising administering to a subject in need thereof a therapeutically effective amount of a Compound of the Disclosure.

In another embodiment, the disclosure provides a method of providing neuroprotection in a subject having a lysosomal storage disorder, the method comprising administering to a subject in need thereof a therapeutically effective amount of a Compound of the Disclosure.

In another embodiment, the disclosure provides a method of treating or delaying the progression of a neurodegenerative disease, the method comprising administering to a subject in need thereof a therapeutically effective amount of a Compound of the Disclosure.

In another embodiment, the disclosure provides a method of treating or delaying the progression of a neurodegenerative disease associated with defects in lysosomal storage, the method comprising administering to a subject in need thereof a therapeutically effective amount of a Compound of the Disclosure.

In another embodiment, the disclosure provides a method of treating or preventing a migraine, and the symptoms associated therewith, the method comprising administering to a subject in need thereof a therapeutically effective amount of a Compound of the Disclosure.

In another aspect, the disclosure provides a method of improving mobility and/or cognitive function, the method comprising administering to a subject in need thereof a therapeutically effective amount of a Compound of the Disclosure.

In another aspect, the disclosure provides a method of treating or preventing restless legs syndrome, the method comprising administering to a subject in need thereof a therapeutically effective amount of a Compound of the Disclosure.

In another aspect, the disclosure provides a method of treating or preventing vertigo, the method comprising administering to a subject in need thereof a therapeutically effective amount of a Compound of the Disclosure.

The disclosure also provides the following particular embodiments.

Embodiment I. A method of treating or delaying the progression of a lysosomal storage disorder, the method comprising administering to a patient in need thereof a therapeutically effective amount of a Compound of the Disclosure having Formula I, see above, or a pharmaceutically acceptable salt or solvate thereof, wherein:

$R^1$ is selected from the group consisting of hydrogen and $C_{1-6}$ alkyl;

$R^2$ is $C_{1-6}$ alkyl; and $R^3$, $R^4$, $R^5$, $R^6$, $R^7$, $R^8$, $R^9$, $R^{10}$, $R^{11}$, $R^{12}$, and $R^{13}$ are each independently selected from the group consisting of hydrogen and deuterium, wherein the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more.

Embodiment II. A method of providing neuroprotection in a subject having a lysosomal storage disorder, treating or delaying the progression of a neurodegenerative disease, or treating or delaying the progression of a neurodegenerative disease associated with defects in lysosomal storage, treating or preventing a migraine, and the symptoms associated therewith, treating or preventing restless legs syndrome, and the symptoms associated therewith, treating or preventing vertigo, and the symptoms associated therewith, or improving mobility and/or cognitive function, the method comprising administering to a subject in need thereof a therapeutically effective amount of a Compound of the Disclosure having Formula I, see above, or a pharmaceutically acceptable salt or solvate thereof, wherein:

$R^1$ is selected from the group consisting of hydrogen and $C_{1-6}$ alkyl;

$R^2$ is $C_{1-6}$ alkyl; and $R^3$, $R^4$, $R^5$, $R^6$, $R^7$, $R^8$, $R^9$, $R^{10}$, $R^{11}$, $R^{12}$, and $R^{13}$ are each independently selected from the group consisting of hydrogen and deuterium, wherein the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more.

Embodiment III. The method of Embodiments I or II, wherein the compound having Formula I is optically active.

Embodiment IV. The method of Embodiment III, wherein the optically active compound having Formula I is a compound having Formula II, see above.

Embodiment V. The method of Embodiment III, wherein the compound having Formula I is a compound having Formula III, see above.

Embodiment VI. The method of Embodiment III, wherein the compound having Formula I is a compound having Formula IV, see above.

Embodiment VII. The method of Embodiment III, wherein the compound having Formula I is a compound having Formula V, see above.

Embodiment VIII. The method of any one of Embodiments I-VII, wherein $R^1$ is hydrogen.

Embodiment IX. The method of any one of Embodiments I-VIII, wherein: $R^2$ is $-CR^{2a}R^{2b}R^{2c}$; and $R^{2a}$, $R^{2b}$, and $R^{2c}$ are independently selected from the group consisting of hydrogen and deuterium, wherein the deuterium enrichment of any one or more of $R^{2a}$, $R^{2b}$, and $R^{2c}$ is about 15% or more. In another embodiment, $R^{2a}$, $R^{2b}$, and $R^{2c}$ are each hydrogen, i.e., $R^2$ is methyl.

Embodiment X. The method of any one of Embodiments I-IX, wherein $R^{13}$ is hydrogen.

Embodiment XI. The method of any one of Embodiments I-X, wherein the deuterium enrichment of any two or more of $R^3$, $R^4$, $R^5$, $R^6$, $R^7$, $R^8$, $R^9$, $R^{10}$, $R^{11}$, and $R^{12}$ is about 15% or more.

Embodiment XII. The method of Embodiment XI, wherein the deuterium enrichment of any three or more of $R^3$, $R^4$, $R^5$, $R^6$, $R^7$, $R^8$, $R^9$, $R^{10}$, $R^{11}$, and $R^{12}$ is about 15% or more.

Embodiment XIII. The method of Embodiment XII, wherein the deuterium enrichment of any four or more of $R^3$, $R^4$, $R^5$, $R^6$, $R^7$, $R^8$, $R^9$, $R^{10}$, $R^{11}$, and $R^{12}$ is about 15% or more.

Embodiment XIV. The method of Embodiment XIII, wherein the deuterium enrichment of any five or more of $R^3$, $R^4$, $R^5$, $R^6$, $R^7$, $R^8$, $R^9$, $R^{10}$, $R^{11}$, and $R^{12}$ is about 15% or more.

Embodiment XV. The method of Embodiment XIV, wherein the deuterium enrichment of any six or more of $R^3$, $R^4$, $R^5$, $R^6$, $R^7$, $R^8$, $R^9$, $R^{10}$, $R^{11}$, and $R^{12}$ is about 15% or more.

Embodiment XVI. The method of Embodiment XV, wherein the deuterium enrichment of any seven or more of $R^3$, $R^4$, $R^5$, $R^6$, $R^7$, $R^8$, $R^9$, $R^{10}$, $R^{11}$, and $R^{12}$ is about 15% or more.

Embodiment XVII. The method of Embodiment XVI, wherein the deuterium enrichment of any eight or more of $R^3$, $R^4$, $R^5$, $R^6$, $R^7$, $R^8$, $R^9$, $R^{10}$, $R^{11}$, and $R^{12}$ is about 15% or more.

Embodiment XVIII. The method of Embodiment XI, or a pharmaceutically acceptable salt or solvate thereof, wherein:

the deuterium enrichment of $R^7$ is about 15% or more;

the deuterium enrichment of $R^{10}$ is about 15% or more; and $R^6$, $R^8$, $R^9$, $R^{11}$, and $R^{12}$ are hydrogen.

Embodiment XIX. The method of Embodiment XIII, or a pharmaceutically acceptable salt or solvate thereof, wherein:

the deuterium enrichment of $R^7$ and $R^8$ is about 15% or more;

the deuterium enrichment of $R^{10}$ and $R^{11}$ is about 15% or more; and $R^9$ and $R^{12}$ are hydrogen.

Embodiment XX. The method of Embodiments I or II, wherein the compound having Formula I is selected from the group consisting of:

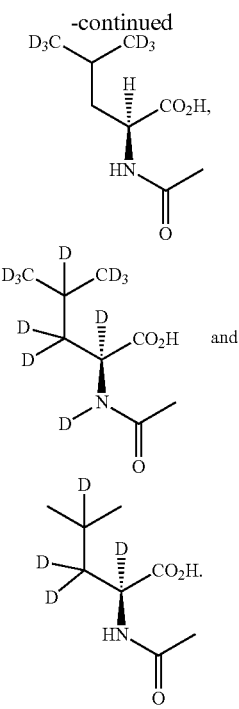

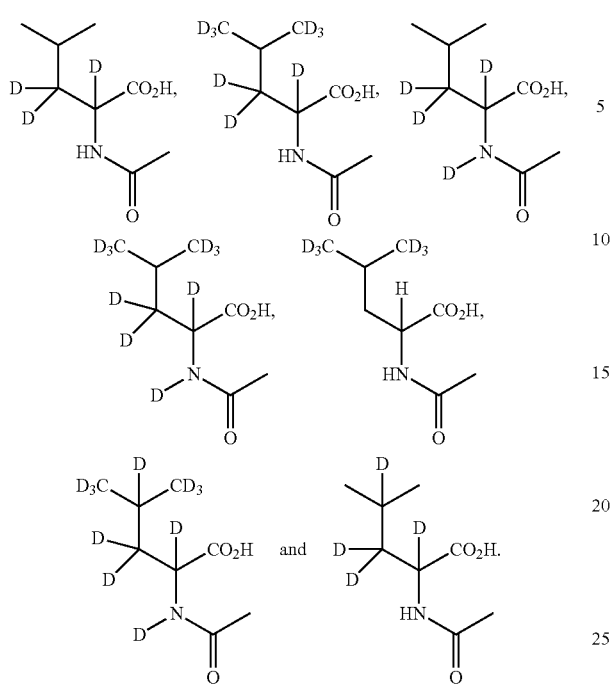

Embodiment XXI. The method of Embodiment III, or a pharmaceutically acceptable salt or solvate thereof, wherein the compound having Formula I is selected from the group consisting of:

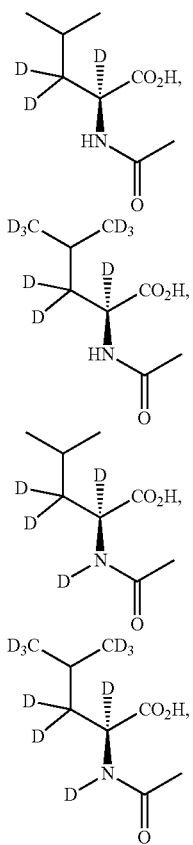

Embodiment XXII. The method of Embodiment III, or a pharmaceutically acceptable salt or solvate thereof, wherein the compound having Formula I is selected from the group consisting of:

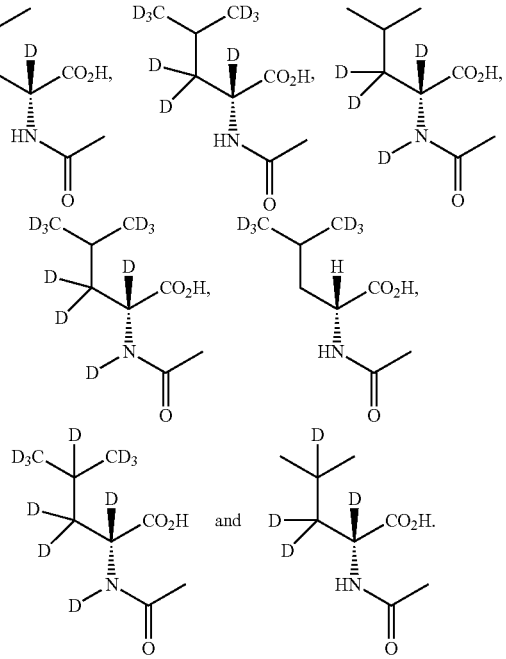

Embodiment XXIII. A Compound of the Disclosure having Formula I, see above, or a pharmaceutically acceptable salt or solvate thereof, wherein:

$R^1$ is selected from the group consisting of hydrogen and $C_{1-6}$ alkyl;

$R^2$ is $C_{1-6}$ alkyl; and $R^3$, $R^4$, $R^5$, $R^6$, $R^7$, $R^8$, $R^9$, $R^{10}$, $R^{11}$, $R^{12}$, and $R^{13}$ are each independently selected from the group consisting of hydrogen and deuterium, wherein the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more, for use in a method of treating or delaying progression of a lysosomal storage disorder.

Embodiment XXIV. A Compound of the Disclosure having Formula I, see above, or a pharmaceutically acceptable salt or solvate thereof, wherein:

$R^1$ is selected from the group consisting of hydrogen and $C_{1-6}$ alkyl;

$R^2$ is $C_{1-6}$ alkyl; and $R^3$, $R^4$, $R^5$, $R^6$, $R^7$, $R^8$, $R^9$, $R^{10}$, $R^{11}$, $R^{12}$, and $R^{13}$ are each independently selected from the group consisting of hydrogen and deuterium, wherein the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more, for use in providing neuroprotection in a subject having a lysosomal disorder, treating or delaying the progression of a neurodegenerative disease, treating or delaying the progression of a neurodegenerative disease associated with defects in lysosomal storage, treating or preventing a migraine, and the symptoms associated therewith, treating or preventing restless legs syndrome, and the symptoms associated therewith, treating or preventing vertigo, and the symptoms associated therewith, or improving mobility and/or cognitive function.

Embodiment XXV. The compound for use of Embodiments XXIII or XXIV, wherein the compound having Formula I is optically active.

Embodiment XXVI. The compound for use of Embodiment XXV, wherein the optically active compound having Formula I is a compound having Formula II, see above.

Embodiment XXVII. The compound for use of Embodiment XXV, wherein the compound having Formula I is a compound having Formula III, see above.

Embodiment XXVIII. The compound for use of Embodiment XXV, wherein the compound having Formula I is a compound having Formula IV, see above.

Embodiment XXIX. The compound for use of Embodiment XXV, wherein the compound having Formula I is a compound having Formula V, see above.

Embodiment XXX. The compound for use of any one of Embodiments XXIII-XXIX, wherein $R^1$ is hydrogen.

Embodiment XXXI. The compound for use of any one of Embodiments XXIII-XXX, wherein:

$R^2$ is —$CR^{2a}R^{2b}R^{2c}$; and $R^{2a}$, $R^{2b}$, and $R^{2c}$ are independently selected from the group consisting of hydrogen and deuterium, wherein the deuterium enrichment of any one or more of $R^{2a}$, $R^{2b}$, and $R^{2c}$ is about 15% or more. In another embodiment, $R^{2a}$, $R^{2b}$, and $R^{2c}$ are each hydrogen, i.e., $R^2$ is methyl.

Embodiment XXXII. The compound for use of any one of Embodiments XXIII-XXXI, wherein $R^{13}$ is hydrogen.

Embodiment XXXIII. The compound for use of any one of Embodiments XXIII-XXXII, wherein the deuterium enrichment of any two or more of $R^3$, $R^4$, $R^5$, $R^6$, $R^7$, $R^8$, $R^9$, $R^{10}$, $R^{11}$, and $R^{12}$ is about 15% or more.

Embodiment XXXIV. The compound for use of Embodiment XXXIII, wherein the deuterium enrichment of any three or more of $R^3$, $R^4$, $R^5$, $R^6$, $R^7$, $R^8$, $R^9$, $R^{10}$, $R^{11}$, and $R^{12}$ is about 15% or more.

Embodiment XXXV. The compound for use of Embodiment XXXIV, wherein the deuterium enrichment of any four or more of $R^3$, $R^4$, $R^5$, $R^6$, $R^7$, $R^8$, $R^9$, $R^{10}$, $R^{11}$, and $R^{12}$ is about 15% or more.

Embodiment XXXVI. The compound for use of Embodiment XXXV, wherein the deuterium enrichment of any five or more of $R^3$, $R^4$, $R^5$, $R^6$, $R^7$, $R^8$, $R^9$, $R^{10}$, $R^{11}$, and $R^{12}$ is about 15% or more.

Embodiment XXXVII. The compound for use of Embodiment XXXVI, wherein the deuterium enrichment of any six or more of $R^3$, $R^4$, $R^5$, $R^6$, $R^7$, $R^8$, $R^9$, $R^{10}$, $R^{11}$, and $R^{12}$ is about 15% or more.

Embodiment XXXVIII. The compound for use of Embodiment XXXVII, wherein the deuterium enrichment of any seven or more of $R^3$, $R^4$, $R^5$, $R^6$, $R^7$, $R^8$, $R^9$, $R^{10}$, $R^{11}$, and $R^{12}$ is about 15% or more.

Embodiment XXXIX. The compound for use of Embodiment XXXVIII, wherein the deuterium enrichment of any eight or more of $R^3$, $R^4$, $R^5$, $R^6$, $R^7$, $R^8$, $R^9$, $R^{10}$, $R^{11}$, and $R^{12}$ is about 15% or more.

Embodiment XL. The compound for use of Embodiment XXXIII, or a pharmaceutically acceptable salt or solvate thereof, wherein:

the deuterium enrichment of $R^7$ is about 15% or more;

the deuterium enrichment of $R^{10}$ is about 15% or more; and $R^6$, $R^8$, $R^9$, $R^{11}$, and $R^{12}$ are hydrogen.

Embodiment XLI. The compound for use of Embodiment XXXV, or a pharmaceutically acceptable salt or solvate thereof, wherein:

the deuterium enrichment of $R^7$ and $R^8$ is about 15% or more;

the deuterium enrichment of $R^{10}$ and $R^{11}$ is about 15% or more; and $R^9$ and $R^{12}$ are hydrogen.

Embodiment XLII. The compound for use of Embodiments XXIII or XXIV, wherein the compound having Formula I is selected from the group consisting of:

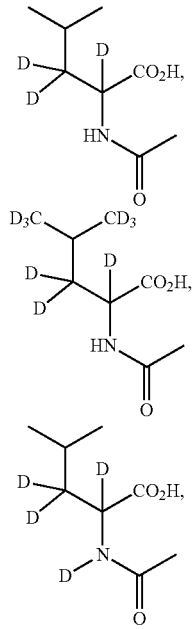

-continued

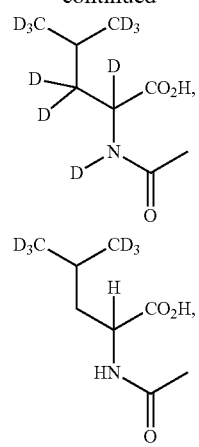

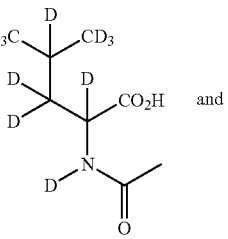

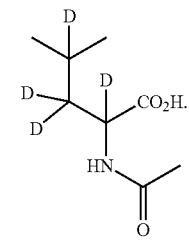

Embodiment XLIII. The compound for use of Embodiment XXV, or a pharmaceutically acceptable salt or solvate thereof, wherein the compound having Formula I is selected from the group consisting of:

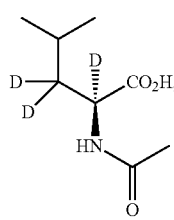 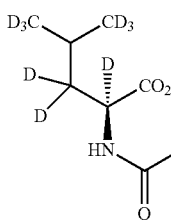 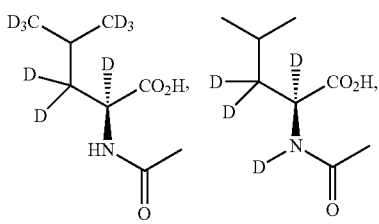

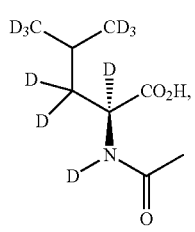 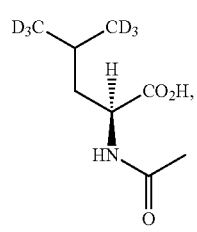

-continued

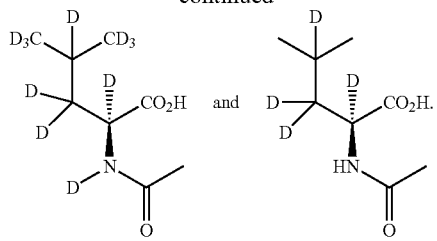

Embodiment XLIV. The compound for use of Embodiment XXV, or a pharmaceutically acceptable salt or solvate thereof, wherein the compound having Formula I is selected from the group consisting of:

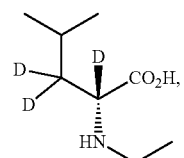

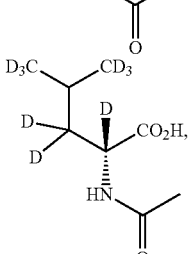

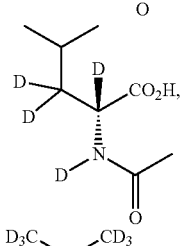

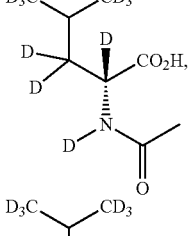

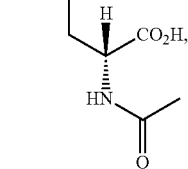

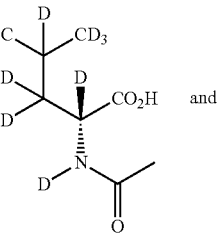

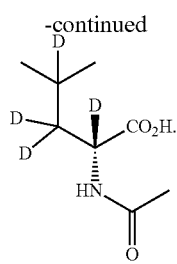

Embodiment XLV. Else of a Compound of the Disclosure having Formula I, see above, or a pharmaceutically acceptable salt or solvate thereof, wherein:

$R^1$ is selected from the group consisting of hydrogen and $C_{1-6}$ alkyl;

$R^2$ is $C_{1-6}$ alkyl; and $R^3$, $R^4$, $R^5$, $R^6$, $R^7$, $R^8$, $R^9$, $R^{10}$, $R^{11}$, $R^{12}$, and $R^{13}$ are each independently selected from the group consisting of hydrogen and deuterium, wherein the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more, in the manufacture of a medicament for treating or delaying progression of a lysosomal storage disorder.

Embodiment XLVI. A Compound of the Disclosure having Formula I, see above, or a pharmaceutically acceptable salt or solvate thereof, wherein:

$R^1$ is selected from the group consisting of hydrogen and $C_{1-6}$ alkyl;

$R^2$ is $C_{1-6}$ alkyl; and $R^3$, $R^4$, $R^5$, $R^6$, $R^7$, $R^8$, $R^9$, $R^{10}$, $R^{11}$, $R^{12}$, and $R^{13}$ are each independently selected from the group consisting of hydrogen and deuterium, wherein the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more, in the manufacture of a medicament for providing neuroprotection in a subject having a lysosomal disorder, treating or delaying the progression of a neurodegenerative disease, treating or delaying the progression of a neurodegenerative disease associated with defects in lysosomal storage, treating or preventing a migraine, and the symptoms associated therewith, treating or preventing restless legs syndrome, and the symptoms associated therewith, treating or preventing vertigo, and the symptoms associated therewith, or improving mobility and/or cognitive function.

Embodiment XL VII. The use of Embodiments XLV or XLVI, wherein the compound having Formula I is optically active.

Embodiment XL VIII. The use of Embodiment XL VII, wherein the optically active compound having Formula I is a compound having Formula II, see above.

Embodiment XLIX. The use of Embodiment XLVII, wherein the compound having Formula I is a compound having Formula III, see above.

Embodiment L. The use of Embodiment XLVII, wherein the compound having Formula I is a compound having Formula IV, see above.

Embodiment LI The use of Embodiment XLVII, wherein the compound having Formula I is a compound having Formula V, see above.

Embodiment LII. The use of any one of Embodiments XLV-LI, wherein $R^1$ is hydrogen.

Embodiment LIII. The use of any one of Embodiments XLV-LII, wherein:

$R^2$ is $-CR^{2a}R^{2b}R^{2c}$; and $R^{2a}$, $R^{2b}$, and $R^{2c}$ are independently selected from the group consisting of hydrogen and deuterium, wherein the deuterium enrichment of any one or more of $R^{2a}$, $R^{2b}$, and $R^{2c}$ is about 15% or more. In another embodiment, $R^{2a}$, $R^{2b}$, and $R^{2c}$ are each hydrogen, i.e., $R^2$ is methyl.

Embodiment LIV. The use of any one of Embodiments XLV-LIII, wherein $R^{13}$ is hydrogen.

Embodiment LV. The use of any one of Embodiments XLV-LIV, wherein the deuterium enrichment of any two or more of $R^3$, $R^4$, $R^5$, $R^6$, $R^7$, $R^8$, $R^9$, $R^{10}$, $R^{11}$, and $R^{12}$ is about 15% or more.

Embodiment LVI. The use of Embodiment LV, wherein the deuterium enrichment of any three or more of $R^3$, $R^4$, $R^5$, $R^6$, $R^7$, $R^8$, $R^9$, $R^{10}$, $R^{11}$, and $R^{12}$ is about 15% or more.

Embodiment LVII. The use of Embodiment LVI, wherein the deuterium enrichment of any four or more of $R^3$, $R^4$, $R^5$, $R^6$, $R^7$, $R^8$, $R^9$, $R^{10}$, $R^{11}$, and $R^{12}$ is about 15% or more.

Embodiment LVIII. The use of Embodiment LVII, wherein the deuterium enrichment of any five or more of $R^3$, $R^4$, $R^5$, $R^6$, $R^7$, $R^8$, $R^9$, $R^{10}$, $R^{11}$, and $R^{12}$ is about 15% or more.

Embodiment LIX. The use of Embodiment LVIII, wherein the deuterium enrichment of any six or more of $R^3$, $R^4$, $R^5$, $R^6$, $R^7$, $R^8$, $R^9$, $R^{10}$, $R^{11}$, and $R^{12}$ is about 15% or more.

Embodiment LX. The use of Embodiment LIX, wherein the deuterium enrichment of any seven or more of $R^3$, $R^4$, $R^5$, $R^6$, $R^7$, $R^8$, $R^9$, $R^{10}$, $R^{11}$, and $R^{12}$ is about 15% or more.

Embodiment LXI. The use of Embodiment LX, wherein the deuterium enrichment of any eight or more of $R^3$, $R^4$, $R^5$, $R^6$, $R^7$, $R^8$, $R^9$, $R^{10}$, $R^{11}$, and $R^{12}$ is about 15% or more.

Embodiment LXII. The use of Embodiment LV, or a pharmaceutically acceptable salt or solvate thereof, wherein:

the deuterium enrichment of $R^7$ is about 15% or more;

the deuterium enrichment of $R^{10}$ is about 15% or more; and $R^6$, $R^8$, $R^9$, $R^{11}$, and $R^{12}$ are hydrogen.

Embodiment LXIII. The use of Embodiment LVII, or a pharmaceutically acceptable salt or solvate thereof, wherein:

the deuterium enrichment of $R^7$ and $R^8$ is about 15% or more;

the deuterium enrichment of $R^{10}$ and $R^{11}$ is about 15% or more; and $R^9$ and $R^{12}$ are hydrogen.

Embodiment LXIV. The use of Embodiments XLV or XLVI, wherein the compound having Formula I is selected from the group consisting of:

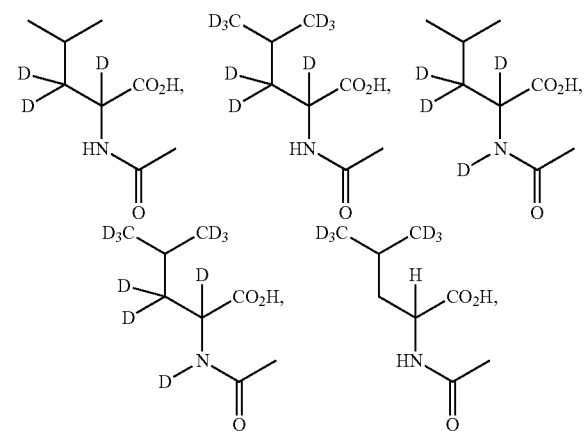

-continued

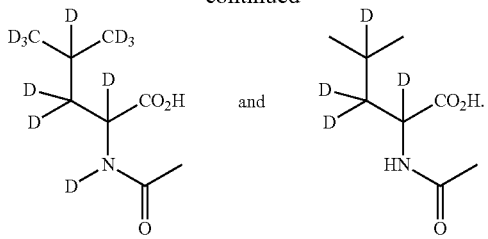 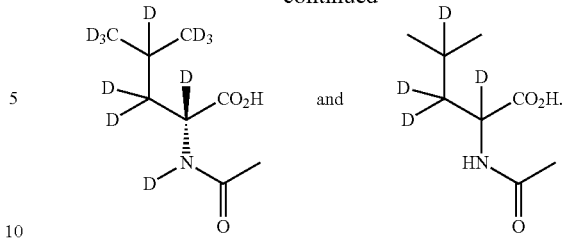

Embodiment LXV. The use of Embodiment XLVII, or a pharmaceutically acceptable salt or solvate thereof, wherein the compound having Formula I is selected from the group consisting of:

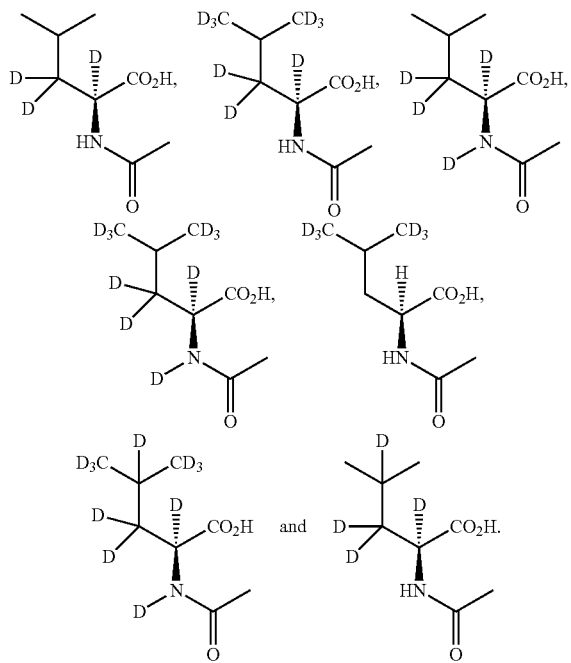

Embodiment LXVI. The use of Embodiment XLVII, or a pharmaceutically acceptable salt or solvate thereof, wherein the compound having Formula I is selected from the group consisting of:

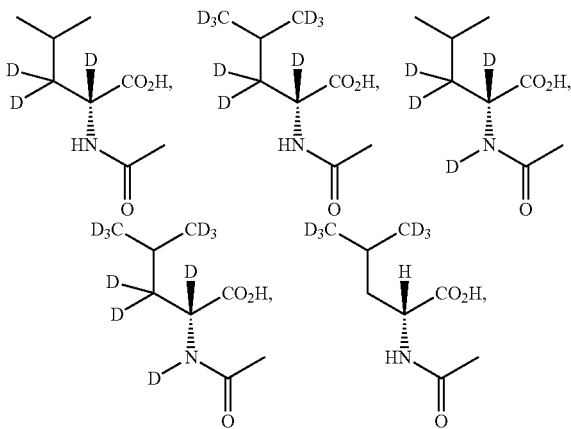

Embodiment LXVII. A pharmaceutical composition comprising a Compound of the Disclosure having Formula I, see above, or a pharmaceutically acceptable salt or solvate thereof, wherein:
$R^1$ is selected from the group consisting of hydrogen and $C_{1-6}$ alkyl;
$R^2$ is $C_{1-6}$ alkyl; and
$R^3$, $R^4$, $R^5$, $R^6$, $R^7$, $R^8$, $R^9$, $R^{10}$, $R^{11}$, $R^{12}$, and $R^{13}$ are each independently selected from the group consisting of hydrogen and deuterium,
wherein the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more,
for use in a method of treating or delaying progression of a lysosomal storage disorder.

Embodiment LXVIII. A pharmaceutical composition comprising a Compound of the Disclosure having Formula I, see above, or a pharmaceutically acceptable salt or solvate thereof, wherein:
$R^1$ is selected from the group consisting of hydrogen and $C_{1-6}$ alkyl;
$R^2$ is $C_{1-6}$ alkyl; and
$R^3$, $R^4$, $R^5$, $R^6$, $R^7$, $R^8$, $R^9$, $R^{10}$, $R^{11}$, $R^{12}$, and $R^{13}$ are each independently selected from the group consisting of hydrogen and deuterium,
wherein the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more,
for use in providing neuroprotection in a subject having a lysosomal disorder, treating or delaying the progression of a neurodegenerative disease, treating or delaying the progression of a neurodegenerative disease associated with defects in lysosomal storage, treating or preventing a migraine, and the symptoms associated therewith, treating or preventing restless legs syndrome, and the symptoms associated therewith, treating or preventing vertigo, and the symptoms associated therewith, or improving mobility and/or cognitive function.

Embodiment LXIX. The pharmaceutical composition of Embodiments LXVII or LXVIII, wherein the compound having Formula I is optically active.

Embodiment LXX. The pharmaceutical composition of Embodiment LXIX, wherein the optically active compound having Formula I is a compound having Formula II, see above.

Embodiment LXXI. The pharmaceutical composition of Embodiment LXIX, wherein the compound having Formula I is a compound having Formula III, see above.

Embodiment LXXII. The pharmaceutical composition of Embodiment LXIX, wherein the compound having Formula I is a compound having Formula IV, see above.

Embodiment LXXIII. The pharmaceutical composition of Embodiment LXIX, wherein the compound having Formula I is a compound having Formula V, see above.

Embodiment LXXIV. The pharmaceutical composition of any one of Embodiments LXVII-LXXIII, wherein $R^1$ is hydrogen.

Embodiment LXXV. The pharmaceutical composition of any one of Embodiments LXVII-LXXIV, wherein:

$R^2$ is —$CR^{2a}R^{2b}R^{2c}$; and $R^{2a}$, $R^{2b}$, and $R^{2c}$ are independently selected from the group consisting of hydrogen and deuterium, wherein the deuterium enrichment of any one or more of $R^{2a}$, $R^{2b}$, and $R^{2c}$ is about 15% or more. In another embodiment, $R^{2a}$, $R^{2b}$, and $R^{2c}$ are each hydrogen, i.e., $R^2$ is methyl.

Embodiment LXXVI. The pharmaceutical composition of any one of Embodiments LXVII-LXXV, wherein $R^{13}$ is hydrogen.

Embodiment LXXVII. The pharmaceutical composition of any one of Embodiments LXVII-LXXVI, wherein the deuterium enrichment of any two or more of $R^3$, $R^4$, $R^5$, $R^6$, $R^7$, $R^8$, $R^9$, $R^{10}$, $R^{11}$, and $R^{12}$ is about 15% or more.

Embodiment LXXVIII. The pharmaceutical composition of Embodiment LXXVII, wherein the deuterium enrichment of any three or more of $R^3$, $R^4$, $R^5$, $R^6$, $R^7$, $R^8$, $R^9$, $R^{10}$, $R^{11}$, and $R^{12}$ is about 15% or more.

Embodiment LXXIX. The pharmaceutical composition of Embodiment LXXVIII, wherein the deuterium enrichment of any four or more of $R^3$, $R^4$, $R^5$, $R^6$, $R^7$, $R^8$, $R^9$, $R^{10}$, $R^{11}$, and $R^{12}$ is about 15% or more.

Embodiment LXXX. The pharmaceutical composition of Embodiment LXXIX, wherein the deuterium enrichment of any five or more of $R^3$, $R^4$, $R^5$, $R^6$, $R^7$, $R^8$, $R^9$, $R^{10}$, $R^{11}$, and $R^{12}$ is about 15% or more.

Embodiment LXXXI. The pharmaceutical composition of Embodiment LXXX, wherein the deuterium enrichment of any six or more of $R^3$, $R^4$, $R^5$, $R^6$, $R^7$, $R^8$, $R^9$, $R^{10}$, $R^{11}$, and $R^{12}$ is about 15% or more.

Embodiment LXXXII. The pharmaceutical composition of Embodiment LXXXI, wherein the deuterium enrichment of any seven or more of $R^3$, $R^4$, $R^5$, $R^6$, $R^7$, $R^8$, $R^9$, $R^{10}$, $R^{11}$, and $R^{12}$ is about 15% or more.

Embodiment LXXXIII. The pharmaceutical composition of Embodiment LXXXII, wherein the deuterium enrichment of any eight or more of $R^3$, $R^4$, $R^5$, $R^6$, $R^7$, $R^8$, $R^9$, $R^{10}$, $R^{11}$, and $R^{12}$ is about 15% or more.

Embodiment LXXXIV. The pharmaceutical composition of Embodiment LXXVII, or a pharmaceutically acceptable salt or solvate thereof, wherein:

the deuterium enrichment of $R^7$ is about 15% or more;

the deuterium enrichment of $R^{10}$ is about 15% or more; and $R^6$, $R^8$, $R^9$, $R^{11}$, and $R^{12}$ are hydrogen.

Embodiment LXXXV. The pharmaceutical composition of Embodiment LXXIX, or a pharmaceutically acceptable salt or solvate thereof, wherein:

the deuterium enrichment of $R^7$ and $R^8$ is about 15% or more;

the deuterium enrichment of $R^{10}$ and $R^{11}$ is about 15% or more; and $R^9$ and $R^{12}$ are hydrogen.

Embodiment LXXXVI. The pharmaceutical composition of Embodiments LXVII or LXVIII, wherein the compound having Formula I is selected from the group consisting of:

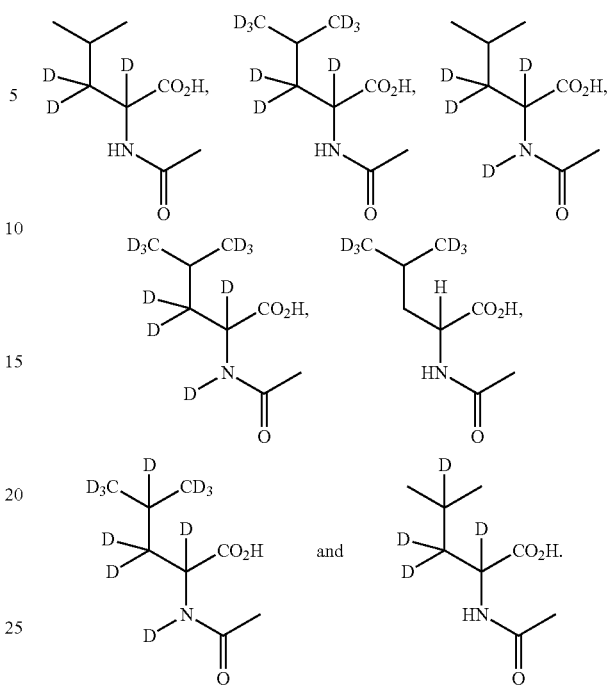

Embodiment LXXXVII. The pharmaceutical composition of Embodiment LXIX, or a pharmaceutically acceptable salt or solvate thereof, wherein the compound having Formula I is selected from the group consisting of:

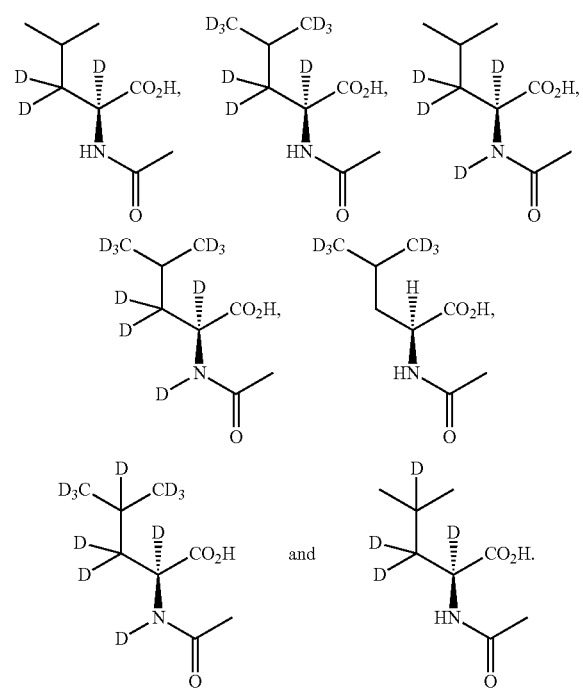

Embodiment LXXXVIII. The pharmaceutical composition of Embodiment LXIX, or a pharmaceutically acceptable salt or solvate thereof, wherein the compound having Formula I is selected from the group consisting of:

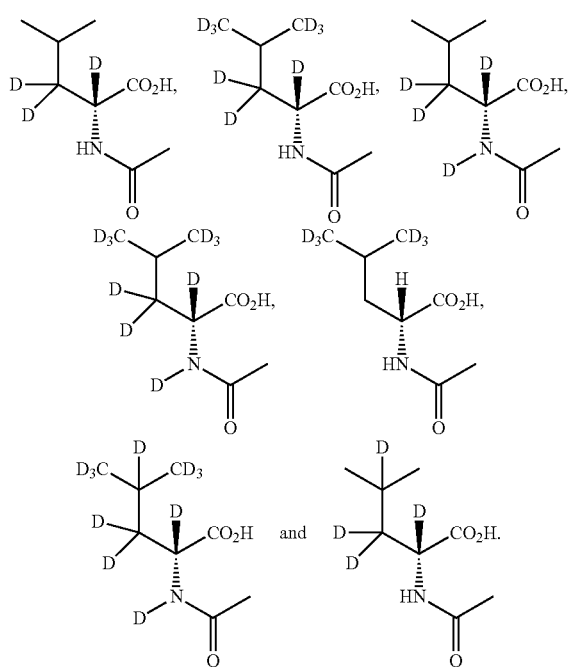

Embodiment LXXXIX. A kit comprising a Compound of the Disclosure having Formula I, see above, or a pharmaceutically acceptable salt or solvate thereof, wherein:

$R^1$ is selected from the group consisting of hydrogen and $C_{1-6}$ alkyl;

$R^2$ is $C_{1-6}$ alkyl; and $R^3$, $R^4$, $R^5$, $R^6$, $R^7$, $R^8$, $R^9$, $R^{10}$, $R^{11}$, $R^{12}$, and $R^{13}$ are each independently selected from the group consisting of hydrogen and deuterium, wherein the deuterium enrichment of any one or more of $R^3$, $R^4$, $R^5$, $R^6$, $R^7$, $R^8$, $R^9$, $R^{10}$, $R^{11}$, $R^{12}$, and $R^{13}$ is about 15% or more, and instructions for administering the compound to a subject to treat or delay progression of a lysosomal storage disorder, or for providing neuroprotection in a subject having a lysosomal disorder, or treat or delay the progression of a neurodegenerative disease, treating or delaying the progression of a neurodegenerative disease associated with defects in lysosomal storage, treating or preventing a migraine, and the symptoms associated therewith, treating or preventing restless legs syndrome, and the symptoms associated therewith, treating or preventing vertigo, and the symptoms associated therewith, or improving mobility and/or cognitive function.

Embodiment XC. The kit of Embodiment LXXXIX, wherein the compound having Formula I is optically active.

Embodiment XCI. The kit of Embodiment XC, wherein the optically active compound having Formula I is a compound having Formula II, see above.

Embodiment XCII. The kit of Embodiment XC, wherein the compound having Formula I is a compound having Formula III, see above.

Embodiment XCIII. The kit of Embodiment XC, wherein the compound having Formula I is a compound having Formula IV, see above.

Embodiment XCIV. The kit of Embodiment XC, wherein the compound having Formula I is a compound having Formula V, see above.

Embodiment XCV. The kit of any one of Embodiments LXXXIX-XCIV, wherein $R^1$ is hydrogen.

Embodiment XC VI. The kit of any one of Embodiments LXXXIX-XCV, wherein:

$R^2$ is $-CR^{2a}R^{2b}R^{2c}$; and $R^{2a}$, $R^{2b}$, and $R^{2c}$ are independently selected from the group consisting of hydrogen and deuterium, wherein the deuterium enrichment of any one or more of $R^{2a}$, $R^{2b}$, and $R^{2c}$ is about 15% or more. In another embodiment, $R^{2a}$, $R^{2b}$, and $R^{2c}$ are each hydrogen, i.e., $R^2$ is methyl.

Embodiment XC VII. The kit of any one of Embodiments LXXXIX-XC VI, wherein $R^{13}$ is hydrogen.

Embodiment XCVIII. The kit of any one of Embodiments LXXXIX-XC VII, wherein the deuterium enrichment of any two or more of $R^3$, $R^4$, $R^5$, $R^6$, $R^7$, $R^8$, $R^9$, $R^{10}$, $R^{11}$, and $R^{12}$ is about 15% or more.

Embodiment XCIX. The kit of Embodiment XCVIII, wherein the deuterium enrichment of any three or more of $R^3$, $R^4$, $R^5$, $R^6$, $R^7$, $R^8$, $R^9$, $R^{10}$, $R^{11}$, and $R^{12}$ is about 15% or more.

Embodiment C. The kit of Embodiment XCIX, wherein the deuterium enrichment of any four or more of $R^3$, $R^4$, $R^5$, $R^6$, $R^7$, $R^8$, $R^9$, $R^{10}$, $R^{11}$, and $R^{12}$ is about 15% or more.

Embodiment CI. The kit of Embodiment C, wherein the deuterium enrichment of any five or more of $R^3$, $R^4$, $R^5$, $R^6$, $R^7$, $R^8$, $R^9$, $R^{10}$, $R^{11}$, and $R^{12}$ is about 15% or more.

Embodiment CII. The kit of Embodiment CI, wherein the deuterium enrichment of any six or more of $R^3$, $R^4$, $R^5$, $R^6$, $R^7$, $R^8$, $R^9$, $R^{10}$, $R^{11}$, and $R^{12}$ is about 15% or more.

Embodiment CIII. The kit of Embodiment CII, wherein the deuterium enrichment of any seven or more of $R^3$, $R^4$, $R^5$, $R^6$, $R^7$, $R^8$, $R^9$, $R^{10}$, $R^{11}$, and $R^{12}$ is about 15% or more.

Embodiment CIV. The kit of Embodiment CIII, wherein the deuterium enrichment of any eight or more of $R^3$, $R^4$, $R^5$, $R^6$, $R^7$, $R^8$, $R^9$, $R^{10}$, $R^{11}$, and $R^{12}$ is about 15% or more.

Embodiment CV. The kit of Embodiment XCVIII, or a pharmaceutically acceptable salt or solvate thereof, wherein:

the deuterium enrichment of $R^7$ is about 15% or more;

the deuterium enrichment of $R^{10}$ is about 15% or more; and $R^6$, $R^8$, $R^9$, $R^{11}$, and $R^{12}$ are hydrogen.

Embodiment CVI. The kit of Embodiment C, or a pharmaceutically acceptable salt or solvate thereof, wherein:

the deuterium enrichment of $R^7$ and $R^8$ is about 15% or more;

the deuterium enrichment of $R^{10}$ and $R^{11}$ is about 15% or more; and $R^9$ and $R^{12}$ are hydrogen.

Embodiment CVII. The kit of Embodiment LXXXIX, wherein the compound having Formula I is selected from the group consisting of:

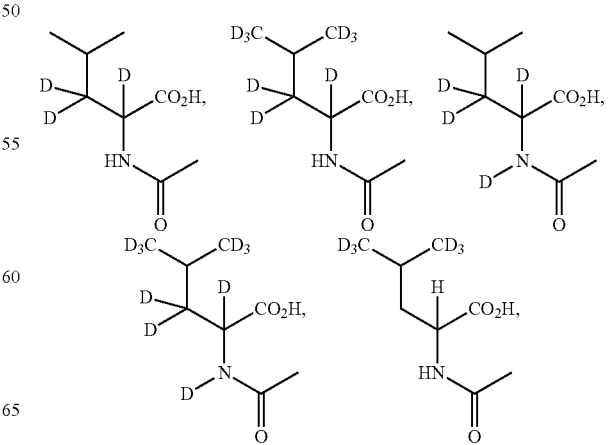

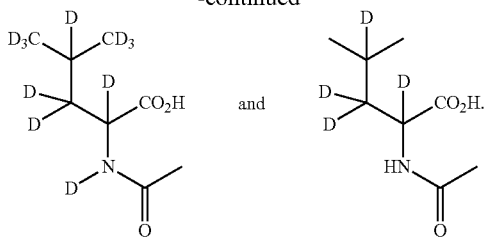
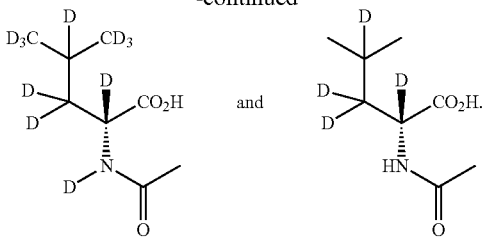

Embodiment CVIII. The kit of Embodiment XC, or a pharmaceutically acceptable salt or solvate thereof, wherein the compound having Formula I is selected from the group consisting of:

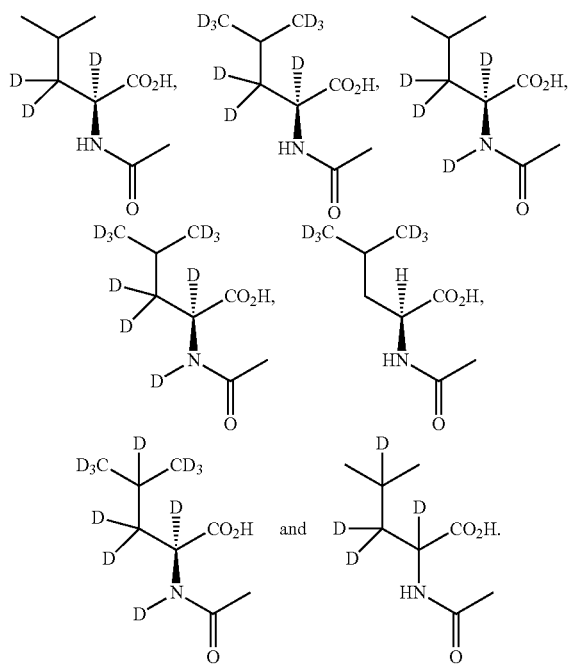

Embodiment CIX. The kit of Embodiment XC, or a pharmaceutically acceptable salt or solvate thereof, wherein the compound having Formula I is selected from the group consisting of:

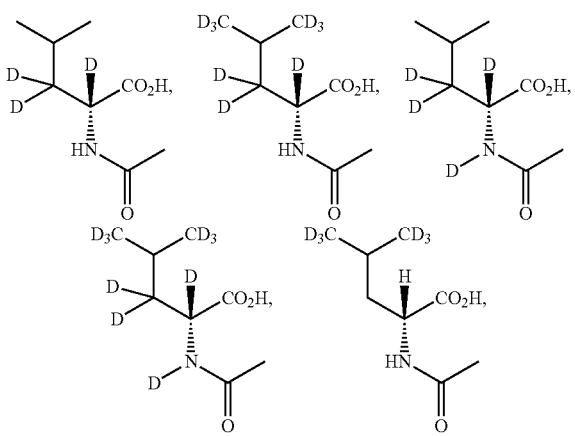

In another embodiment, a Compound of the Disclosure is administered in combination with a second therapeutic agent useful in the treatment of a LSD, a neurodegenerative disease, or a migraine, restless legs syndrome, or vertigo, or useful for improving mobility and/or cognitive function. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is typically known in the art, and the second therapeutic agent is administered to a subject in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered.

The term "subject" as used herein may be a vertebrate, mammal, or domestic animal. Hence, compositions according to the disclosure may be used to treat any mammal, for example livestock, e.g. a horse, cow, sheep or pig, pets, e.g. a cat, dog, rabbit or guinea pig, a laboratory animal, e.g. a mouse or rat, or may be used in other veterinary applications. In one embodiment, the subject is a human being.

The terms "treat," "treating," "treatment," and the like as used herein, unless otherwise indicated, refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

The terms "prevent," "preventing," and "prevention" as used herein refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of a Compound of the Disclosure that is sufficient, when administered by a method of the disclosure, to deliver the compound for the treatment of the condition or disease of interest to a subject in need thereof, and produces a desired effect in the subject. In the case of a LSD or a neurodegenerative disease, the therapeutically effective amount of a Compound of the Disclosure may, e.g., delay the time to appearance of a symptom of a LSD or a mark associated with a LSD or delay the time to appearance of a symptom of a neurodegenerative disease.

The term "lysosomal storage disorder" or "LSD" as used herein refers to any disorder that involves dysfunction or disruption in the late endosomal/lysosomal system. A LSD may involve an increased volume and/or pH of the endosomal/lysosomal system. A LSD may also involve increased storage of lipid or non-lipids.

The LSD may be a primary lysosomal hydrolase defect, a post-translational processing defect of lysosomal enzymes, a trafficking defect for lysosomal enzymes, a defect in lysosomal enzyme protection, a defect in soluble non-enzymatic lysosomal proteins, a transmembrane (non-enzyme) protein defect or an unclassified defect.

Primary lysosomal hydrolase defects include, but are not limited to, Gaucher disease (glucosylceramidase defect), GM1 gangliosidosis (GM1-β-galactosidase defect), Tay-Sachs disease (β-hexosaminidase A defect), Sandhoff disease (β-hexosaminidase A+B defect), Fabry disease (α-galactosidase A defect), Krabbe disease (β-galactosyl ceramidase defect), Niemann-Pick Type A and B (sphingomyelinase defect), metachromatic leukodystrophy (arylsulphatase A defect), MPS IH (Hurler syndrome; α-iduronidase defect), MPS IS (Scheie syndrome; α-iduronidase defect), MPS IH-S(Hurler-Scheie syndrome; α-iduronidase defect), MPS II (Hunter syndrome; iduronate sulphatase defect), MPS IIIA (Sanfdippo A syndrome; heparan sulphamidase defect), MPS MB (Sanfdippo B syndrome; acetyl α-glucosaminidase defect), MPS IIIC (Sanfdippo C syndrome; acetyl CoA: α-glucosaminide N-acetyltransferase defect), MPS HID (Sanfdippo D syndrome; N-acetyl glucosamine-6-sulphatase defect), MPS IV A (Morquio A disease; acetyl galactosamine-6-sulphatase defect), MPS IVB (Morquio B disease; β-galactosidase defect), MPS V (redesignated MPS IS), MPS VI (Maroteaux Lamy Syndrome; acetyl galactosamine-4-sulphatase (arylsulphatase B) defect), MPS VII (Sly Syndrome; β-glucuronidase defect), MPS IX (hyaluronidase defect), Wolman disease (WD; acid lipase defect), Farber disease (acid ceramidase defect), cholesteryl ester storage disease (acid lipase defect), Pompe disease (Type II; a 1,4-glucosidase defect), aspartylglucosaminuria (glycosylasparaginase defect), fucosidosis (α-fucosidase defect), α-mannosidosis (α-mannosidase defect), β-mannosidosis (β-mannosidase defect), Schindler disease (N-acetylgalactosaminidase defect), sialidosis (α-neuraminidase defect), infantile neuronal ceroid lipofuscinoses (CLN1; palmitoyl protein thioesterase defect), late infantile neuronal ceroid lipofuscinoses (CLN2; carboxypeptidase defect), early infantile GM1 gangliosidosis, late infantile GM1 gangliosidosis, adult infantile GM1 gangliosidosis, Gaucher Disease Type 1 (Non-Neuronopathic), Gaucher Disease Type 2/3 (Neuronopathic), ML1 (MLI; Sialidosis, alpha-N-acetyl neuraminidase (sialidase) deficiency, ML2 (MLII, I-cell disease; N-acetyl glucosamine phosphoryl transferase defect) ML3 (MLIII, pseudo-Hurler polydystrophy; N-acetyl glucosamine phosphoryl transferase defect), ML4 (MLIV, Mucolipin 1 deficiency), Neuronal Ceroid Lipofuscinoses Type 4 (CLN4; Kufs disease; Adult NCL; palmotoyl-protein thioesterase-1 deficiency (Type A); Cathepsin F deficiency (Type B)), Neuronal Ceroid Lipofuscinoses Type 8—Northern Epilepsy (CLN8), Neuronal Ceroid Lipofuscinoses Type 8—Turkish Late Infantile (CLN8), Neuronal Ceroid Lipofuscinoses Type 9—German/Serbian Late Infantile (CLN9), Neuronal Ceroid Lipofuscinoses Type 10 (CLN10; Congenital Cathepsin D Deficiency), Pycnodysostosis (Cathepsin K defect), Infantile-Onset Pompe Disease, Late-Onset Pompe Disease, and Cholesteryl Ester Storage Disease.

Post-translational processing defects of lysosomal enzymes include, but are not limited to, mucosulphatidosis (MSD; multiple sulphatase defect).

Trafficking defects for lysosomal enzymes include, but are not limited to, mucolipidosis type II (I-cell disease; N-acetyl glucosamine phosphoryl transferase defect), mucolipidosis type IDA (pseudo-Hurler polydystrophy; N-acetyl glucosamine phosphoryl transferase defect) and mucolipidosis type IIIC.

Defects in lysosomal enzyme protection include, but are not limited to, galactosialidosis (protective protein cathepsin A (PPCA) defect), β-galactosidase defects and neuraminidase defects. Defects in soluble non-enzymatic lysosomal proteins include, but are not limited to, GM2 activator protein deficiency (variant AB), sphingolipid activator protein (SAP) deficiency and neuronal ceroid lipofuscinoses (NCL) (CLN5).

Transmembrane (non-enzyme) protein defects include, but are not limited to, Danon disease (lysosome-associated membrane protein 2 (LAMP2) defect), NPC (NPC1 and/or NPC2 defect), cystinosis (cystinosin defect), infantile free sialic acid storage disease (ISSD; sialin defect), Salla disease (free sialic acid storage; sialin defect), juvenile neuronal ceroid lipofuscinoses (CLN3, Batten disease), neuronal ceroid lipofuscinoses (NCL) (CLN6 and CLN8) and mucolipidosis type IV (mucolipin defect).

Unclassified defects include, but are not limited to, neuronal ceroid lipofuscinoses (NCL) (CLN4 and CLN7).

The LSD to be treated, delayed, or ameliorated by the compounds, compositions, and methods of the disclosure is any of NPC (NPC1 and/or NPC2 defect, primary or secondary), Smith-Lemli-Opitz Syndrome (SLOS), an inborn error of cholesterol synthesis, Tangier disease, Pelizaeus-Merzbacher disease, the neuronal ceroid lipofuscinoses, primary glycosphingolipidoses (i.e. Gaucher, Fabry, GM1, GM2 gangliosidoses, Krabbe and metachromatic leukodystrophy (MLD)), Farber disease and multiple sulphatase deficiency.

In some embodiments, LSDs having a significant central nervous system (CNS) involvement, such as NPC, Tay-Sachs disease, Sandhoff disease, GM1 gangliosidosis or Fabry disease are treated or delayed by Compounds of the Disclosure and the compositions and methods described herein.

Niemann-Pick diseases are a heterogeneous group of autosomal recessive LSDs. Common cellular features include abnormal sphingomyelin (SM) storage in mononuclear phagocytic cells and parenchymal tissues, as well as (hepato)splenomegaly. Among the three main subgroups (A-C), NPC (previously classified as NPC and NPD and now appreciated to be a single disease) is classified as a fatal neurovisceral LSD caused by abnormal intracellular cholesterol transport-induced accumulation of unesterified cholesterol in late endosome/lysosomal compartments.

Outside the CNS, the cellular characteristics of NPC include abnormal accumulation of unesterified cholesterol and other lipids (e.g. GSLs) within late endosome/lysosomal compartments. Conversely, there is no net elevation in cholesterol in the CNS (although it does have an altered distribution) but there are highly elevated levels of GSLs. Progressive neurodegeneration is particularly characterized by sequential degeneration of GABAergic Purkinje neurons in the cerebellum, which parallels the onset and progression of cerebellar ataxia and other aspects of neurological dysfunctions seen during the course of NPC. Genetic studies have shown that NPC disease is caused by mutations in either the Npc1 or Npc2 genes. The precise mechanistic link between these two genes remains unknown and the functional roles of these proteins remains enigmatic. NPC1 encodes a multimembrane spanning protein of the limiting membrane of the late endosome/lysosome, whereas NPC2 is a soluble cholesterol binding protein of the lysosome. When NPC1 is inactivated, sphingosine is the first lipid to be stored, suggesting that NPC1 plays a role in the transport of sphingosine from the lysosome, where it is normally generated as part of sphingolipid catabolism. Elevated sphingosine in turn causes a defect in calcium entry into acidic stores resulting in greatly reduced calcium release from this compartment. This then prevents late endosome-lysosome fusion, which is a calcium dependent process, and causes the secondary accumulation of lipids (cholesterol, sphingomyelin and glycosphingolipids) that are cargos in transit through the late endocytic pathway.

Other secondary consequences of inhibiting NPC1 function include defective endocytosis and failure to clear autophagic vacuoles. It has been shown that the NPC1/NPC2 cellular pathway is targeted by pathogenic mycobacteria to promote their survival in late endosomes. In one embodiment, the Niemann-Pick disease is a Niemann-Pick type A, B, C1 or C2 disease.

Tay-Sachs disease is a fatal hereditary disorder of lipid metabolism characterized especially in CNS tissue due to deficiency of the A (acidic) isozyme of β-hexosaminidase. Mutations in the HEXA gene, which encodes the a subunit of β-hexosaminidase, cause the A isozyme deficiency. Tay-Sachs is a prototype of a group of disorders, the GM2 gangliosidoses, characterized by defective GM2 ganglioside degradation. The GM2 ganglioside (monosialylated ganglioside 2) accumulates in the neurons beginning already in fetal life. In one embodiment, the Tay-Sachs disease is the Tay-Sachs AB variant.

Sandhoff disease results from a deficiency of both the A and B (basic) isozymes of β-hexosaminidase. Mutations in the HEXB gene, which encodes the β subunit of β-hexosaminidase, cause the B isozyme deficiency.

GM1 gangliosidosis is caused by a deficiency of β-galactosidase, which results in lysosomal storage of GM1 ganglioside (monosialylated ganglioside 1).

Fabry disease is caused by a deficiency of α-galactosidase, which results in lysosomal storage of a ceramide trihexoside.

The term "neurodegenerative disease", as used herein, refers to any disorder that affects neurons and involves the progressive loss of neuronal structure, the progressive loss of neuronal function, or progressive neuron cell death.

Neurodegenerative diseases include, but are not limited to, alcoholism, Alexander's disease, Alper's disease, Alzheimer's Disease, amyotrophic lateral sclerosis (ALS), ataxia telangiectasia, neuronal ceroid lipofuscinoses, Batten disease, bovine spongiform encephalopathy (BSE), Canavan disease, cerebral palsy, Cockayne syndrome, corticobasal degeneration, Creutzfeldt-Jakob disease, frontotemporal lobar degeneration, Gaucher's disease, Huntington's disease, HIV-associated dementia, Kennedy's disease, Krabbe's disease, Lewy body dementia, lysosomal storage disorders, neuroborreliosis, Machado-Joseph disease, multiple system atrophy, multiple sclerosis, multiple sulfatase deficiency, mucolipidoses, narcolepsy, Niemann-Pick type C, Niemann Pick disease, Parkinson's Disease, lower body Parkinson's syndrome, Pelizaeus-Merzbacher Disease, Pick's disease, Pompe disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Ba 5 tten disease, cerebellar ataxia, spinocerebellar ataxia, spinal muscular atrophy, Steele-Richardson-Olszewski disease, Tabes *dorsalis*, Tay-Sachs disease, dentatorubral-pallidoluysian atrophy, Episodic Ataxia (EA) 1, Episodic Ataxia (EA) 2, Episodic Ataxia (EA) 3, Episodic Ataxia (EA) 4, Episodic Ataxia (EA) 5, Episodic Ataxia (EA) 6, Episodic Ataxia (EA) 7, Autosomal Recessive Spastic Ataxia of Charlevoix-Saguenay (ARSACS), Autosomal Recessive Cerebellar Ataxia Type 1 (Recessive Ataxia of Beauce (RAB)), Autosomal Recessive Cerebellar Ataxia Type 2 (spinocerebellar ataxia autosomal recessive 9, SCAR9), Ataxia with Oculomotor Apraxia Type 1 (AOA1), Ataxia with Oculomotor Apraxia Type 2 (AOA2), Ataxia with Vitamin E Deficiency (AVED), Freidreich's Ataxia (FRDA), mitochondrial recessive ataxia syndrome (MIRAS), Myclonic Epilepsy Myopathy Sensory Ataxia (MEMSA), Sensory Ataxic Neuropathy Dysarthria Opthalmoparesis (SANDO), ataxia with coenzyme Q10 deficiency, mitochondrial myopathy, encephalopathy, lactacidosis, stroke syndrome (MELAS), myoclonic epilepsy with ragged red fibers (MERRF), neurogenic muscle weakness, ataxia, and retinitis pigmentosa (NARP), Kearns-Sayre (KSS), Fragile X tremor/ataxia syndrome (FXTAS), Arts Syndrome, Christianson type X-linked syndromic mental retardation, X-linked sideroblastic anemia, Idiopathic Late-Onset Cerebellar Ataxia, Sporadic Adult-Onset Ataxia of Unknown Etiology (SAOA), transmissible mink encephalopathy, chronic wasting disease, feline spongiform encephalopathy, exotic ungulate encephalopathy, Kuru, variant Creutzfeldt-Jakob disease, Gerstmann-Sträussler-Scheinker syndrome, fatal familial insomnia, hereditary motor and sensory neuropathy with proximal dominance, Wobbly Hedgehog Syndrome (WHS), progressive muscular atrophy (Duchenne-Aran muscular atrophy), progressive bulbar palsy, pseudobulbar palsy, HIV-associated neurocognitive disorders (HAND), parkinsonism, and scrapie.

In one embodiment, the spinocerebellar ataxia is infantile-onset spinocerebellar ataxia, Spinocerebellar Ataxia (SCA) 1, Spinocerebellar Ataxia (SCA) 2, Spinocerebellar Ataxia (SCA) 3 (Machado-Joseph disease), Spinocerebellar Ataxia (SCA) 4, Spinocerebellar Ataxia (SCA) 5 (Lincoln's Ataxia), Spinocerebellar Ataxia (SCA) 6, Spinocerebellar Ataxia (SCA) 7, Spinocerebellar Ataxia (SCA) 8, Spinocerebellar Ataxia (SCA) 10, Spinocerebellar Ataxia (SCA) 11, Spinocerebellar Ataxia (SCA) 12, Spinocerebellar Ataxia (SCA) 13, Spinocerebellar Ataxia (SCA) 14, Spinocerebellar Ataxia (SCA) 15/16, Spinocerebellar Ataxia (SCA) 17, Spinocerebellar Ataxia (SCA) 18 (sensory/motor neuropathy with ataxia), Spinocerebellar Ataxia (SCA) 19/22, Spinocerebellar Ataxia (SCA) 20, Spinocerebellar Ataxia (SCA) 21, Spinocerebellar Ataxia (SCA) 23, Spinocerebellar 5 Ataxia (SCA) 24, Spinocerebellar Ataxia (SCA) 25, Spinocerebellar Ataxia (SCA) 26, Spinocerebellar Ataxia (SCA) 27, Spinocerebellar Ataxia (SCA) 28 (spinocerebellar ataxia autosomal recessive type 4 (SCAR4); Spinocerebellar ataxia with saccadic intrusions), Spinocerebellar Ataxia (SCA) 29, Spinocerebellar Ataxia (SCA) 30, Spinocerebellar Ataxia (SCA) 31, Spinocerebellar Ataxia (SCA) 32, Spinocerebellar Ataxia (SCA) 35, Spinocerebellar Ataxia (SCA) 36, X-linked Spinocerebellar Ataxia 1, X-linked Spinocerebellar Ataxia 2, X-linked Spinocerebellar Ataxia 3, X-linked Spinocerebellar Ataxia 4 or X-linked Spinocerebellar Ataxia 5.

In one embodiment, the neurodegenerative disease is cerebellar ataxia. In one embodiment, the neurodegenerative disease is Niemann Pick disease. In one embodiment, the neurodegenerative disease is parkinsonism. In one embodiment, the neurodegenerative disease is neuronopathic Gaucher disease. In one embodiment, the neurodegenerative disease is Sandhoff's disease. In one embodiment, the neurodegenerative disease is Louis-Barr syndrome. In one embodiment, the neurodegenerative disease is Alzheimer's disease. In one embodiment, the neurodegenerative disease is Parkinson's disease. In one embodiment, the neurodegenerative disease is multiple systems atrophy. In one embodiment, the neurodegenerative disease is fronto-temporal dementia. In one embodiment, the neurodegenerative disease is lower body Parkinson's syndrome.

The main symptoms of Parkinson's Disease (PD) are rigidity, tremor, and slow movement. There are other diseases in which these symptoms are prevalent. These diseases, and PD itself, fall under the umbrella term Parkinsonism. PD can be referred to as Primary Parkinsonism. Other examples of Parkinsonisms include: Multiple System Atrophy; Progressive Supranuclear Palsy; Normal pressure hydrocephalus; and Vascular or arteriosclerotic parkinsonism. Those diseases that can be classed as Parkinsonisms, but are not PD, can also be referred to as "Parkinson-Plus Syndromes." Unlike PD patients, individuals with Parkinson-Plus Syndromes do not respond to LDopa. The term "parkinsonism" as used herein may refer to a motor syndrome whose main symptoms are tremor at rest, stiffness, slowing of movement and postural instability. Parkinsonian syndromes can be divided into four subtypes, according to their origin: primary or idiopathic; secondary or acquired; hereditary parkinsonism; and Parkinson plus syndromes or multiple system degeneration.

In one embodiment, the parkinsonism is a Parkinson plus syndrome or multiple system degeneration. In one embodiment, the parkinsonism is vascular Parkinsonism (arteriosclerotic Parkinsonism; lower-body Parkinsonism), Multiple System Atrophy with predominant parkinsonism (MSA-P), Multiple System Atrophy with cerebellar features (MSA-C; Sporadic olivopontocerebellar atrophy (OPCA)), Shy-Drager syndrome, Progressive supranuclear Palsy (Steele-Richardson-Olszewski syndrome), Lewy body dementia, Pick's disease, or frontotemporal dementia and parkinsonism linked to chromosome 17.

The phrase "delay progression of a LSD" and the like as used herein means delaying the onset, i.e., increasing the time to appearance, of a symptom of a LSD or a mark associated with a LSD in a subject (compared to that typically observed). It may include substantially slowing, preventing, or even entirely preventing, the onset of the disease or of one or more symptoms and/or complications associated with the disease.

The phrase "delaying progression of a neurodegenerative disease" or "delaying progression of a neurodegenerative disease associated with defects in lysosomal storage" refer to delaying the onset, i.e., increasing the time to appearance, of a symptom of a neurodegenerative disease or neurodegenerative disease associated with defects in lysosomal storage, or a mark associated with a neurodegenerative disease or neurodegenerative disease associated with defects in lysosomal storage (compared to that typically observed). It may include substantially slowing, preventing, or even entirely preventing, the onset of the disease or of one or more symptoms and/or complications associated with the disease.

Delaying progression thus includes, but is not limited to, delaying or preventing symptoms and/or complications resulting from or associated with, e.g., a LSD, a neurodegenerative disease, or a neurodegenerative disease associated with defects in lysosomal storage. When provided prophylactically, acetyl-leucine is typically provided before the onset of a symptom of a LSD, a neurodegenerative disease, or a neurodegenerative disease associated with defects in lysosomal storage. Such prophylactic administration is typically to delay or prevent the onset of symptoms of the LSD, a neurodegenerative disease, or a neurodegenerative disease associated with defects in lysosomal storage.

A "symptom" of a LSD includes any clinical or laboratory manifestation associated with a LSD and is not limited to what the subject can feel or observe. Symptoms as described herein include neurological symptoms. Examples of neurological symptoms include ataxia, dystonia, vertical and horizontal supranuclear saccade/gaze palsy and dementia. Also included are psychiatric symptoms such as depression or psychosis. Most of the LSDs can be diagnosed based on the subject history, clinical findings, biochemical markers and genetic testing.

A "symptom" of a neurodegenerative disease, optionally associated with defects in lysosomal storage, includes any clinical or laboratory manifestation associated with a neurodegenerative disease and is not limited to what the subject can feel or observe. Symptoms as described herein include neurological symptoms.

Progression could be said to be delayed when the time to appearance of a symptom of a LSD or a mark associated with a LSD, or appearance of a symptom of a neurodegenerative disease takes at least 5% longer than that typically observed for a subject having a LSD or neurodegenerative disease. In some embodiments, an increase in time of at least 10%, at least 15%, at least 20%, at least 25%, at least 30%, at least 40%, at least 50%, at least 60%, at least 70%, at least 80%, at least 90% or at least 100% is observed.

Disease treatment or progression can be assessed using one or more of the following: the Scale for the Assessment and Rating of Ataxia (SARA), Spinocerebellar Ataxia Functional Index (SCAFI), the modified Disability Rating Scale (mDRS), EuroQol 5Q-5D-5L (EQ-5D-5L), the visual analogue scale (VAS), Wechsler Adult Intelligence Scale-Revised (WAIS-R), Wechsler Intelligence Scale for Children-IV (WISC-IV), or Montreal Cognitive Assessment (MoCA). For certain LSDs, such as NPC, particular scores have been developed and validated over the last decades, for instance the modified 6-Domain NP-C disability Scale (mDRS score). In this regard, certain scores in these tests are characteristic of symptomatic LSD or neurodegenerative subjects. Thus, "delaying progression of a LSD" or "delaying progression of a neurodegenerative disease" can mean increasing the time taken for a subject to reach a SARA, SCAFI, mDRS, EQ-5D-5L, VAS, WAIS-R, WISC-IV and/or MoCA score, or other relevant test, that is characteristic of a symptomatic LSD subject or neurodegenerative subject (compared to that typically observed).

"Treating a neurodegenerative disease," "treating a neurodegenerative disease associated with defects in lysosomal storage," or "treating a LSD" may be equated with an improvement in a SARA, SCAFI, mDRS, EQ-5D-5L, VAS, WAIS-R, WISC-IV and/or MoCA score, or result of another test suitable for characterizing a neurodegenerative disease or LSD subject. In some embodiments, treatment improves such as score from a value characteristic of a symptomatic subject to a value characteristic of a non-symptomatic subject.

Any change in LSD or neurodegenerative disease progression, for example, over time or through treatment, can be monitored by using one or more well-established tests, as discussed further herein, at two or more time points and comparing the results.

Thus, to evaluate overall neurological status, mDRS, a four-domain scale (ambulation, manipulation, language and swallowing), can be applied. Cerebellar function can be evaluated using SARA, an eight-item clinical rating scale (gait, stance, sitting, speech, fine motor function and taxis; range 0-40, where 0 is the best neurological status and 40 the worst), and SCAFI, comprising the 8-m-Walking-Time (8 MW; performed by having subjects walking twice as quickly as possible from one line to another excluding turning), 9-Hole-Peg-Test (9HPT) and the number of "PATA" repetitions over 10 s. Subjective impairment and quality of life can be evaluated using the EQ-5D-5L questionnaire and VAS. To assess ocular motor function, 3-dimensional videooculography (EyeSeeCam) can be used to measure the peak velocity of saccades, gain of smooth pursuit, peak slow phase velocity of gaze-evoked nystagmus (gaze-holding function), peak slow phase velocity of optokinetic nystagmus, and gain of horizontal vestibulo-ocular reflex. To evaluate the cognitive state, WAIS-R or WISC-IV, and MoCA, assessing different cognitive domains, including attention and concentration, executive functions, memory, language, visuoconstructional skills, conceptual thinking, calculations, and orientation with a maximum of 30 points and a cut-off score of 26, can be used. The skilled person will know how to perform such tests.

The term "treating a migraine," as used herein refers to reducing the frequency of, alleviating or eliminating migraines, or one or more symptoms related thereto.

The term "preventing a migraine," as used herein refers to preventing migraines, or one or more symptoms associated therewith. A Compound of the Disclosure may be used prophylactically.

The term "alleviating" as used herein means rendering migraines, or one or more symptoms associated therewith, less severe or less intense than in the absence of treatment.

As used herein, the term "reducing the frequency of a migraine" means reducing the occurrence of migraines, or one or more symptoms associated therewith, within a particular time frame relative to the occurrence in the absence of treatment.

In one embodiment, the Compound of the Disclosure reduces the frequency of, alleviates or eliminates one or more migraine symptoms selected from headache, tiredness, aura, nausea, vomiting, sensitivity to light, sensitivity to sound, sensitivity to smell, sweating, poor concentration, feeling hot or cold, abdominal pain and diarrhea.

As used herein, a symptom associated with migraine includes any clinical or laboratory manifestation associated with a migraine and is not limited to what the subject can feel or observe.

In another embodiment, the disclosure provides a Compound of the Disclosure for use in treating, or more preferably preventing, an aura, e.g., a visual aura.

In another embodiment, the disclosure provides a Compound of the Disclosure for use in treating or preventing a migraine associated with an aura (for example, a "classic migraine").

In another embodiment, the disclosure provides a Compound of the Disclosure for use in treating or preventing a migraine that is not associated with an aura (for example, a "common migraine").

In another embodiment, the disclosure provides a Compound of the Disclosure for use in treating or preventing an aura associated with a migraine headache.

In another embodiment, the disclosure provides a Compound of the Disclosure for use in treating or preventing an aura that is not associated with a migraine headache.

In another embodiment, the disclosure provides a Compound of the Disclosure for use in treating or preventing a hemiplegic migraine. For this embodiment, the migraine typically comprises a headache and an aura that are accompanied by motor weakness.

In another embodiment, the disclosure provides a Compound of the Disclosure for use in treating or preventing a sporadic hemiplegic migraine.

In another embodiment, the disclosure provides a Compound of the Disclosure for use in treating or preventing a vestibular migraine. Vestibular migraines can be defined according to diagnostic criteria set forth by the International Classification Committee of the Barany Society and are typically characterized by:

A. At least 5 episodes with vestibular symptoms (as defined by the Barany Society's Classification of Vestibular Symptoms) of moderate or severe intensity, lasting 5 minutes to 72 hours;

B. Current or previous history of migraine with or without aura according to the International Classification Headache Disorders (ICHD);

C. One or more migraine features with at least 50% of the vestibular episodes:

1. headache with at least two of the following characteristics: one sided location, pulsating quality, moderate or severe pain intensity, aggravation by routine physical activity;

2. photophobia and phonophobia;

3. visual aura;

D. Not better accounted for by another vestibular or ICHD diagnosis.

In another embodiment, the disclosure provides a Compound of the Disclosure for use in treating or preventing a basilar-type migraine. For this embodiment, the migraine typically comprises a headache and an aura that are accompanied by one or more of the following symptoms: difficulty speaking, world spinning, ringing in ears, and other brainstem-related symptoms.

In another embodiment, the disclosure provides a Compound of the Disclosure for use in treating or preventing a retinal migraine. For this embodiment, the retinal migraine typically includes headaches accompanied by visual disturbances or temporary blindness.

In another embodiment, the disclosure provides a Compound of the Disclosure for use in treating or preventing chronic migraine. As used herein, the term "chronic migraine" refers to a subject suffering more than fifteen headache days per month over a three month period of which more than eight are migrainous, in the absence of medication (as defined by The International Headache Society).

In another embodiment, the disclosure provides a Compound of the Disclosure for use in treating or preventing episodic migraine. As used herein, "episodic migraine" refers to a subject suffering less than fifteen headache days per month over a three month period, in the absence of medication (as defined by The International Headache Society).

In another embodiment, the disclosure provides a Compound of the Disclosure for use in treating or preventing acute migraine.

In another embodiment, the disclosure provides a Compound of the Disclosure for use in treating or preventing one or more prodromal symptoms associated with a migraine. Preferably, the prodromal symptoms are selected from one or more of altered mood, irritability, depression or euphoria, fatigue, craving for certain food(s), stiff muscles (especially in the neck), constipation, diarrhea, and sensitivity to smells and noise In another embodiment, the disclosure provides a Compound of the Disclosure for use in treating or preventing pain associated with a migraine.

In another embodiment, the disclosure provides a Compound of the Disclosure for use in treating or preventing one or more postdromal symptoms associated with a migraine. Preferably, the postdromal symptoms are selected from one or more of soreness in the area where the migraine was, impaired thinking, tiredness, head pain, cognitive difficulties, gastrointestinal symptoms, mood changes and weakness.

In another embodiment, the disclosure provides a Compound of the Disclosure that reduces, alleviates or eliminates migraine headaches.

In another embodiment, the disclosure provides a Compound of the Disclosure that alleviates or eliminates aura.

In another embodiment, the disclosure provides a Compound of the Disclosure that reduces the frequency of, alleviates or eliminates one or more symptoms selected from visual problems or visual disturbances, numbness or tingling, dizziness, balance problems, motor problems, speech difficulties and loss of consciousness.

In another embodiment, the disclosure provides a Compound of the Disclosure that prevents an aura from occurring, for example, by preventing one or more of the above-mentioned symptoms from occurring.

In one embodiment, the disclosure provides a Compound of the Disclosure for use in a method of improving cognitive function, mobility, or cognitive function and mobility in a subject.

In another embodiment, the disclosure provides a Compound of the Disclosure for use in a method of improving cognitive function in a subject.

In another embodiment, the disclosure provides a Compound of the Disclosure for use in a method of improving mobility in a subject.

In another embodiment, the subject is an elderly subject.

In another embodiment, the disclosure provides a Compound of the Disclosure for use in a method of improving mobility and/or cognitive function in an elderly subject.

In another embodiment, the disclosure provides a method of improving mobility and/or cognitive function in an elderly subject, the method comprising administering a therapeutically effective amount of a Compound of the Disclosure to the subject.

In another embodiment, the cognitive function is one or more selected from the group consisting of perception, memory, creation of imagery, awareness, reasoning, thinking and capacity for judgment.

According to the present disclosure, a Compound of the Disclosure may be used to treat an age-related decrease in cognitive function and/or mobility.

In another embodiment, the disclosure provides a Compound of the Disclosure for use in treating restless legs syndrome.

In another embodiment, the disclosure provides a Compound of the Disclosure for use in treating vertigo.

"Mobility" refers to the ability of a subject to move. Mobility may be assessed in the elderly using one or more simple tests. For example, the "get up and go" test is a simple test capable of measuring mobility. In this test, the speed of sit to stand and walking to a target point is analyzed.

For example, the test may begin with the subject sitting in a chair. At the start of the stop clock, the subject should rise unaided and walk to a target point. The target point may be 2-10 m away, optionally 4-6 m away. The stop clock should be stopped upon the subject reaching the target point. Any change in mobility, for example, over time or through treatment, can be monitored by using the "get up and go" test at two or more time points and comparing the results. Other suitable tests for measuring mobility include those used in the Elderly Mobility Scale (EMS), a 20-point validated assessment tool for the assessment of frail elderly subjects considering locomotion, balance and key position changes.

The phrase "improving mobility," as referred to herein, means a positive change in the ability of the subject to move. The positive change can be measured using any of the aforementioned tests on two or more occasions, for example, a first occasion to measure baseline mobility and a second occasion to measure mobility following a period of time (in which treatment may have been administered). The more confident the subject feels due to improved steadiness (with treatment, for example) the more rapidly he or she completes the test. Mobility could be said to be improved when at least a about 5% increase in performance in the relevant test, between two time points, is observed. For example, an increase in performance of at least about 10%, at least about 15%, at least about 20%, at least about 25%, at least about 30%, at least about 40%, at least about 50%, at least about 60%, at least about 70%, at least about 80%, at least about 90% or at least about 100% in the relevant test, between the two time points, is observed. Further for example, an increase in performance of at least 5%, at least 10%, at least 15%, at least 20%, at least 25%, at least 30%, at least 40%, at least 50%, at least 60%, at least 70%, at least 80%, at least 90% or at least 100% in the relevant test, between the two time points, is observed. The two time points may be one week apart, two weeks apart, three weeks apart, four weeks apart, two months apart, three months apart, four months apart, five months apart or even six months apart. Treatment may be administered during the intervening period. Thus, as an example, "improving mobility" can mean that the subject will demonstrate an at least about 5% increase in speed from a baseline measurement, as measured using the "get up and go" test as defined herein. For example, the subject may demonstrate an increase in speed in this test of at least about 10%, at least about 15%, at least about 20%, at least about 25%, at least about 30%, at least about 40%, at least about 50%, at least about 60%, at least about 70%, at least about 80%, at least about 90% or at least about 100%. Further for example, the subject may demonstrate an increase in speed in this test of at least 5%, at least 10%, at least 15%, at least 20%, at least 25%, at least 30%, at least 40%, at least 50%, at least 60%, at least 70%, at least 80%, at least 90% or at least 100%.

In one embodiment, the subject has a mobility disorder associated with ageing.

The term "mobility disorder associated with ageing" as used herein refers to an impairment in mobility that is a direct consequence of the ageing process; this is in contrast with an impairment in mobility that is not a direct consequence of the ageing process. Clinical presentation may differ between subjects with a mobility disorder associated with ageing and subjects with impairment in mobility that is not a direct consequence of the ageing process, for example subjects with ataxia. Ataxia may present as a subject slaloming during walking, while a mobility disorder associated with ageing may present as an increased propensity to falls. Thus, for example, cerebellar ataxia is not a mobility disorder associated with ageing.

In addition to the mobility assessments disclosed above, mobility in a subject having a mobility disorder associated with ageing may be tested, for example, using assessments of balance and/or through monitoring the number of falls experienced by the subject and/or using the "get up and go" test.

In another embodiment, the disclosure provides a Compound of the Disclosure for use to improve balance in a subject, wherein the subject has impaired balance associated with ageing. According to the present disclosure, the impaired balance associated with ageing is not vertigo.

According to the present disclosure, the subject may, for example, not have benign paroxysmal positional vertigo (BPPV); vestibular neuritis; vertigo related to Meniere's disease, Wallenberg's syndrome, cerebellar ischemia, perilymph fistula or acoustic neurinoma; or recurring vertigo of traumatic or toxic origin.

In another embodiment, the disclosure provides a Compound of the Disclosure for use to treat balance disorder associated with ageing.

In another embodiment, the disclosure provides a Compound of the Disclosure for use to increase a subject's stability, for example when standing and/or walking, wherein the subject has decreased stability associated with ageing.

In another embodiment, the disclosure provides a Compound of the Disclosure for use to reduce a subject's unsteadiness whilst walking, wherein the subject has increased unsteadiness associated with ageing.

In another embodiment, the disclosure provides a Compound of the Disclosure for use to treat a subject with impaired gait wherein the impaired gait is associated with ageing. The subject may have senile gait disorder.

In another embodiment, the disclosure provides a Compound of the Disclosure for use to increase gait velocity and or cadence in a subject wherein the subject has impaired gait velocity and or cadence associated with ageing.

In another embodiment, the disclosure provides a Compound of the Disclosure for use to treat a subject that has a pre-disposition to falls, wherein the pre-disposition to falls is associated with ageing.

"Cognitive function" can mean any mental process that involves a symbolic operation, for example, perception, memory, creation of imagery, awareness, reasoning, thinking and capacity for judgment. Measures of cognitive functioning include assessment tools designed to measure, for example: (a) general intelligence, (b) nonverbal intelligence, (c) achievement, (d) attention/executive functioning, (e) memory and learning, (f) visual-motor and motor functioning and (g) language. Such assessment tools are well-known in the art and include, for example, Wechsler Adult Intelligence Scale and Woodcock-Johnson III Tests of Cognitive Abilities (both for assessing general intelligence), Raven Progressive Matrices (for assessing nonverbal intelligence), Wide Range Achievement Test and Woodcock-Johnson III Tests of Achievement (for assessing academic achievement), Conners' Continuous Performance Test II (for assessing attention/executive functioning), Wide Range Assessment of Memory and Learning (for assessing memory and learning), Bender Visual-Motor Gestalt Test, Halstead-Reitan Grip Strength Test, Halstead-Reitan Finger Tapping Test and Lafayette Grooved Pegboard Task (all for assessing visual-motor and motor functioning) and Peabody Picture Vocabulary Test (for assessing language).

Cognitive function may also be assessed using reaction speed and/or alertness tests, such as the Psychomotor Vigilance Task (e.g. as disclosed in the Examples). This test assesses components including fine motor skills; psychomotor speed; lapses of attention; instability of alertness; and impulsivity induced by fatigue.

For example, the Psychomotor Vigilance Task (PVT) is a sustained-attention, reaction timed task that measures the speed with which subjects respond to a visual stimulus. The subject monitors a screen and presses the screen as quickly as possible upon the appearance of visual stimuli. The visual stimuli will then disappear and reappear (at irregular time intervals) e.g., 10 times over the course of the test, with the subject touching the screen as quickly as possible upon each reappearance. Test performance is quantified from an average of the e.g. 10 reaction times. Any change in cognitive function, for example, over time or through treatment, can be monitored by using one or more of these well-established tests at two or more time points and comparing the results.

The phrase "improving cognitive function," as referred to herein, means a positive change in the ability of the subject to perform a symbolic operation, for example, to perceive, remember, create a mental image, have clarity of thought, be aware, to reason, think or judge. The positive change can be measured using any of the aforementioned tests on two or more occasions, for example, a first occasion to measure baseline cognitive function and a second occasion to measure cognitive function following a period of time (in which treatment may have been administered). Cognitive function could be said to be improved when at least about a 5% increase in performance in the relevant test, between two time points, is observed. For example, an increase in performance of at least about 10%, at least about 15%, at least about 20%, at least about 2S %, at least about 30%, at least about 40%, at least about 50%, at least about 60%, at least about 70%, at least about 80%, at least about 90% or at least about 100% in the relevant test, between the two time points, is observed. Further for example, an increase in performance of at least 5%, at least 10%, at least 15%, at least 20%, at least 25%, at least 30%, at least 40%, at least 50%, at least 60%, at least 70%, at least 80%, at least 90% or at least 100% in the relevant test, between the two time points, is observed. The two time points may be one week apart, two weeks apart, three weeks apart, four weeks apart, two months apart, three months apart, four months apart, five months apart or even six months apart. Treatment may be administered during the intervening period. Thus, as an example, "improving cognitive function" can mean that the subject will demonstrate an at least about 5% increase in performance from a baseline measurement, as measured using the well-established Wechsler Adult Intelligence Scale. For example, the subject may demonstrate an increase in performance in this test of at least about 10%, at least about 15%, at least about 20%, at least about 25%, at least about 30%, at least about 40%, at least about 50%, at least about 60%, at least about 70%, at least about 80%, at least about 90% or at least about 100%. Further for example, the subject may demonstrate an increase in performance in this test of at least 5%, at least 10%, at least 15%, at least 20%, at least 25%, at least 30%, at least 40%, at least 50%, at least 60%, at least 70%, at least 80%, at least 90% or at least 100%.

In another embodiment, the disclosure provides a Compound of the Disclosure for use to increase reaction speed, for example the speed in which a subject responds to a visual stimulus.

In one embodiment, the subject has a decrease in cognitive function associated with ageing.

The term "decrease in cognitive function associated with ageing" as used herein refers to a decrease in cognitive function that is a direct consequence of the ageing process; in contrast with a decrease in cognitive function that is not a direct consequence of the ageing process. Clinical presentation may differ between subjects with a decrease in cognitive function associated with ageing and subjects with decrease in cognitive function that is not a direct consequence of the ageing process.

The term "improving" when used in reference to mobility and/or cognitive function may encompass treating and/or ameliorating any impaired mobility and/or cognitive decline in the subject. An age-related decrease in mobility and/or cognitive function may thus be partially or wholly reversed using a Compound of the Disclosure as described herein.

The term "restless legs syndrome" or "RLS" as used herein includes any form of RLS, including primary RLS and secondary RLS. In one embodiment, the RLS is primary RLS. In another embodiment, the RLS is secondary RLS. In another embodiment, the RLS is secondary to a disease or medical condition. Examples of such diseases or medical conditions include iron deficiency, renal failure, uremia, peripheral neuropathy, varicose veins, a neurodegenerative disease, stress, sleep deprivation, fibromyalgia, hyper- or hypothyroidism, pregnancy, cigarette smoking, vitamin deficiency (e.g., vitamin B-12 deficiency), mineral deficiency (e.g., magnesium deficiency), amyloidosis, lyme disease, spinal nerve damage, rheumatoid arthritis, and Sjögren syndrome. In another embodiment, the RLS is secondary to a medication or substance. Examples of such medications or substances include alcohol, caffeine, anticonvulsant drugs (e.g., phenytoin), antidepressants (e.g., amitriptyline, paroxetine), medication for high blood pressure (e.g., beta-blockers), antipsychotics, and withdrawal from medication(s) (e.g., vasodilator drugs, sedatives, antidepressants). Examples of neurodegenerative diseases include Parkinson's Disease, Huntington's disease, hereditary spastic paraparesis, amyotrophic lateral sclerosis (ALS), Alzheimer's disease, frontotemporal dementia, dementia with Lewy bodies, multiple system atrophy, progressive supranuclear palsy, and corticobasal degeneration. In one embodiment, the neurodegenerative disease is a Motor Neuron Disease (e.g., progressive bulbar palsy (PBP), pseudobulbar palsy, primary lateral sclerosis (PLS), amyotrophic lateral sclerosis (ALS), progressive muscular atrophy (PMA), Huntington's disease, multiple sclerosis, Parkinson's Disease, Canavan disease, frontotemporal lobar degeneration, narcolepsy, Pelizaeus-Merzbacher disease, and spinal muscular atrophy). In one embodiment, the neurodegenerative disease is parkinsonism, including primary or idiopathic, secondary or acquired, hereditary parkinsonism, and Parkinson plus syndromes or multiple system degeneration. In another embodiment, the disease or medical condition is associated with dopaminergic system dysfunction, such as dopaminergic cell loss.

A symptom associated with RLS includes any clinical or laboratory manifestation associated with RLS. Symptoms of RLS are often, but need not be, manifestations associated with the disease that the subject can feel or observe. Symptoms associated with RLS include, but are not limited to, lower leg sensations, periodic limb movements of sleep (PLMS), unpleasant leg sensation, urge to move, restlessness, sleep disturbances, excessive daytime sleepiness and the like.

In another embodiment, a Compound of the Disclosure is used in a method for diminishing, inhibiting, or eliminating one or more symptoms associated with RLS in a subject in need thereof. The method comprises administering to the subject a therapeutically effective amount of the Compound of the Disclosure.

In another embodiment, the one or more symptoms are chosen from any one or combination of lower leg sensations, periodic leg movements of sleep, unpleasant leg sensations, urge to move, restlessness, excessive daytime sleepiness, and sleep disturbances.

The severity of RLS or one or more symptoms of RLS may be assessed, e.g., using a known scale, index, rating, or score. For example, the scale, index, rating, score, or other suitable test may correspond to the severity of the RLS overall or to the severity of one or more symptoms associated with RLS. In one embodiment, the treatment described herein improves such an assessment from a value or degree characteristic of a symptomatic subject to a value or degree characteristic of a non-symptomatic subject.

In one embodiment, the treatment described herein improves such an assessment compared to a baseline. The baseline may be, for example, the subject's condition before initiating any treatment for RLS or before initiating treatment for RLS with a Compound of the Disclosure. Alternatively, the baseline may be, for example, the subject's condition after a certain time period on treatment for RLS.

In one embodiment, treatment with a Compound of the Disclosure decreases the subject's International Restless Leg Syndrome Study Group Rating Scale ("IRLS") compared to a baseline. In one embodiment, the IRLS is reduced compared to baseline by at least 10%, at least 20%, at least 30%, at least 40%, or at least 50%. In one embodiment, the IRLS is reduced by at least 60%, at least 70%, at least 80%, at least 90%, or 100%.

The term "vertigo" as used herein includes any form of vertigo including, for example, benign paroxysmal positional vertigo (BPPV), vestibular neuritis; vertigo related to Meniere's disease, Wallenberg's syndrome, cerebellar ischemia, perilymph fistula or acoustic neurinoma, or recurring vertigo of traumatic or toxic origin.

A symptom of vertigo includes any clinical or laboratory manifestation associated with vertigo. Symptoms of vertigo include, but are not limited to, feeling nauseated, vomiting, abnormal or jerking eye movements (nystagmus), headache, sweating, ringing in the ears, and/or hearing loss.

In methods of the present disclosure, a therapeutically effective amount of a Compound of the Disclosure, typically formulated in accordance with pharmaceutical practice, is administered to a subject, e.g., a human being, in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high-pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects, e.g., delay progression of a LSD or neurodegenerative disease, is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the subject, and ultimately is determined by the attendant physician. Dosage amounts and intervals can be adjusted individually to provide plasma levels that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance. In situations where chronic treatment is required, multiple doses per day may administered to the patient for extended periods of time, e.g., for about 3 months, about 6 months, about 1 year, about 2 years, about 3 years, about 5 years, about 10 years, or more.

A Compound of the Disclosure used in a method of the present disclosure can be administered in an amount of about 1 to about 2,000 milligrams (mg) per dose, about 100 to about 1,000 mg per dose, or about 250 to about 750 mg per dose. For example, a Compound of the Disclosure can be administered, per dose, in an amount of about 100, 150, 200, 250, 300, 350, 400, 450, 500, 550, 600, 650, 700, 750, 800, 850, 900, 950, or 1.000 mg, including all doses between 1 and 1000 mg.

A Compound of the Disclosure used in a method of the present disclosure can be administered to a subject at an amount of between 250 and 15,000 mg per day, between 500 and 10,000 mg per day, between 1,000 and 5,000 mg per day, or between 1,500 and 2,500 per day. For example, a Compound of the Disclosure can be administered to a subject, per day, in an amount of about 250 mg, about 500 mg, about 750 mg, about 1,000 mg, about 1,500 mg, about 2,000 mg, about 2,500 mg, about 3,000 mg, about 3,500 mg, about 4,000 mg, about 4,500 mg, about 5,000 mg, about 6,000 mg, about 7,000 mg, about 8.000 mg, about 9,000 mg, about 10,000 mg, about 11,000 mg, about 12,000 mg, about 13.000 mg, about 14,000 mg, or about 15,000 mg.

The total daily dose may be spread across multiple administrations, i.e., administration may be required two or more times a day to achieve the required dose. As an example, the required number of tablets to provide the total daily dose of a Compound of the Disclosure may be split across two administrations (for example, in the morning and evening) or three administrations (for example, in the morning, noon and evening).

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual subject, which can vary with the age, weight, and response of the particular subject.

Kits

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label (and/or instructions) affixed to the container or included in the kit that describes use of the compound or composition to practice methods of the disclosure. In one embodiment, the compound or composition is packaged in a unit dosage form.

The kit further can include a device suitable for administering the composition according to the intended route of administration.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and subject to make an informed decision regarding use of the product. The package insert generally is regarded as the "label" for a pharmaceutical product.

Personalized Medicine

In another embodiment, the disclosure provides procedures of personalized medicine for subjects having a LSD or neurodegenerative disease, a migraine, restless legs syndrome, or vertigo, and the symptoms associated therewith, or for subjects in need of improving mobility and/or cognitive function, and encompasses the selection of treatment options with the highest likelihood of successful outcome for individual subjects having a LSD or neurodegenerative disease, a migraine, restless legs syndrome, or vertigo, and the symptoms associated therewith, or for subjects in need of improving mobility and/or cognitive function. In another aspect, the disclosure relates to the use of an assay(s) to predict the treatment outcome, e.g., the likelihood of favorable responses or treatment success, in subjects having a LSD or neurodegenerative disease, a migraine, restless legs syndrome, or vertigo, and the symptoms associated therewith, or for subjects in need of improving mobility and/or cognitive function.

In another embodiment, the disclosure provides methods of selecting a subject, e.g., human subject for treatment of a LSD or neurodegenerative disease with a Compound of the Disclosure, comprising obtaining a biological sample, e.g., blood cells or cerebrospinal fluid, from the subject, testing a biological sample from the subject for the presence of a LSD-related biomarker or neurodegenerative disease-related biomarker, and selecting the subject for treatment if the biological sample contains the biomarker, e.g., an aberrant level of the biomarker in body fluids such as an accumulation or elevated level of the biomarker in body fluids or a depletion or decreased level of the biomarker in body fluids. In another embodiment, the methods further comprise administering a therapeutically effective amount of a Compound of the Disclosure to the subject if the biological sample contains the biomarker. In another embodiment, the same methods can be applied to subject for treatment of a migraine, restless legs syndrome, or vertigo, and the symptoms associated therewith, or for improving mobility and/or cognitive function.

In another embodiment, the disclosure provides methods for predicting treatment outcomes in a subject having a LSD or neurodegenerative disease, comprising obtaining a biological sample from the subject, testing the biological sample from the subject for the presence of a LSD-related biomarker or neurodegenerative disease-related biomarker, wherein the detection of the biomarker indicates the subject will respond favorably to administration of a therapeutically effective amount of a Compound of the Disclosure. Favorable responses include, but are not limited to, delaying the onset of symptoms that would normally be expected in a subject afflicted with a LSD or neurodegenerative disease. In another embodiment, the same methods for predicting treatment outcomes in a subject can be applied to a subject having a migraine, restless legs syndrome, or vertigo, and the symptoms associated therewith, or to a subject in need of improving mobility and/or cognitive function.

In another embodiment, the disclosure provides methods of treating a LSD or neurodegenerative disease, comprising administering a therapeutically effective amount of a Compound of the Disclosure to a subject, e.g., a human subject, with a LSD or neurodegenerative disease in whom the subject's cells contain a LSD-related biomarker or neurodegenerative disease-related biomarker. In one embodiment, the subject is selected for treatment with a Compound of the Disclosure after the subject's cells have been determined to contain a biomarker, e.g., an elevated level of a LSD-related biomarker or neurodegenerative disease-related biomarker, or a decreased level of a LSD-related biomarker or neurodegenerative disease-related biomarker. In another embodiment, the same methods can be applied to a subject for treatment of a migraine, restless legs syndrome, or vertigo, and the symptoms associated therewith, or for improving mobility and/or cognitive function.

In another embodiment, the method of treating a subject having a LSD or neurodegenerative disease comprises obtaining a biological sample from the subject, determining whether the biological sample contains an elevated level of a LSD-related biomarker or neurodegenerative disease-related biomarker, or a decreased level of a LSD-related biomarker or neurodegenerative disease-related biomarker, and administering to the subject a therapeutically effective amount a Compound of the Disclosure if the biological sample contains an elevated level or decreased level of the biomarker. In another embodiment, the same methods can be applied to a subject for treatment of a subject having a migraine, restless legs syndrome, or vertigo, and the symptoms associated therewith, or for improving mobility and/or cognitive function in a subject.

The term "biomarker" as used herein refers to any biological compound, such as a protein, a fragment of a protein, a peptide, a polypeptide, a nucleic acid, etc. that can be detected and/or quantified in a subject in vivo or in a biological sample obtained from a subject. Furthermore, a biomarker can be the entire intact molecule, or it can be a portion or fragment thereof. In one embodiment, the expression level of the biomarker is measured. The expression level of the biomarker can be measured, for example, by detecting the protein or RNA (e.g., mRNA) level of the biomarker. Biomarkers can also be measure by HPLC-MS/MS. In some embodiments, portions or fragments of biomarkers can be detected or measured, for example, by an antibody or other specific binding agent. In some embodiments, a measurable aspect of the biomarker is associated with a given state of the subject, such as a particular stage of a LSD. For biomarkers that are detected at the protein or RNA level, such measurable aspects may include, for example, the presence, absence, or concentration (i.e., expression level) of the biomarker in a subject, or biological sample obtained from the subject. For biomarkers that are detected at the nucleic acid level, such measurable aspects may include, for example, allelic versions of the biomarker or type, rate, and/or degree of mutation of the biomarker, also referred to herein as mutation status.

The term "LSD-related biomarker" as used herein refers to any biological compound, such as a protein, a fragment of a protein, a peptide, a polypeptide, a nucleic acid, etc. that accumulates or decreases in a subject as a consequence of the pathological enzyme defect or as a result of cytopathological process associated with a LSD. Examples of LSD-related biomarkers include, but are not limited to, globotriaosylceramide (Gb3), globotriaosylsphingosine (LysoGb3), LysoGb3 analogs, or methylated/non-methylated Gb3 isoforms in connection with Fabry disease; glucosylceramide, chitotriosidase (ChT), pulmonary and activation-regulated chemokine (CCL18/PARC), macrophage inflammatory protein 1-alpha and 1-beta (MIP-1α and MIP-1β), Cathepsin K, ganglioside, GM3/monosialodihexosylganglioside, glucosylsphingosine, or osteopontin in connection with Gaucher disease; galactosylceramide, galactosylsphingosine/psychosine in connection with Krabbe disease; dermatan sulfate, heparan sulfate, keratan sulfate, chondroitin-6-sulfate, chondroitin-4,6-sulfate, hyaluronic acid, glycosaminoglycan fragments, β-galactosidase, collagen Iα, fatty-acid-binding-protein 5, nidogen-1, cartilage oligomeric matrix protein, insulin-like growth factor binding protein 7, or protein HEG1 in connection with mucopolysaccharidoses; sphingomyelin, free cholesterol (in fibroblasts), lysosphingomyelin (Lyso-SPM), cholestane-3β,5α,6β triol (C-triol), 7-ketocholesterol (7-KC), 24(S)-hydroxycholesterol, NPCBA1 (3β-hydroxy,7β-N-acetylglucosaminyl-5-cholenoic acid), NPCBA2 (probably 3β,5α,6β-trihydroxycholanoyl-glycine), Calbindin D, Lyso-sphingomyelin-509 in connection with Niemann-Pick disease; and/or glycogen, tetrasaccharide glucose (Glc4), myostatin, or insulin-like growth factor-I (IGF-I) in connection with Pompe disease. See, e.g., Labato et al., *Diseases* 4:40 (2016); Aerts et al., *J Inherit Metab Dis* 34:605-619 (2011); and Giese et al., *Orphanet Journal of Rare Diseases* 70:78 (2015) for LSD-related biomarkers.

The term "neurodegenerative disease-related biomarker" as used herein refers to any biological compound, such as a protein, a fragment of a protein, a peptide, a polypeptide, a nucleic acid, etc. that accumulates in a subject as a consequence of a neurodegenerative disease.

The term "migraine-related biomarker" as used herein refers to any biological compound, such as a protein, a fragment of a protein, a peptide, a polypeptide, a nucleic acid, etc. that accumulates or decreases in a subject as a consequence of a migraine.

The term "mobility-related biomarker" as used herein refers to any biological compound, such as a protein, a fragment of a protein, a peptide, a polypeptide, a nucleic acid, etc. that accumulates or decreases in a subject as a consequence of a decrease in mobility.

The term "cognitive function-related biomarker" as used herein refers to any biological compound, such as a protein, a fragment of a protein, a peptide, a polypeptide, a nucleic acid, etc. that accumulates or decreases in a subject as a consequence of a decrease or change in cognitive function.

In certain aspects of the disclosure, the biomarker is differentially present in a subject of one phenotypic status (e.g., a subject having a LSD) as compared with another phenotypic status (e.g., a normal undiseased subject).

In addition to individual biological compounds, the term "biomarker" as used herein is meant to include groups or sets of multiple biological compounds. For example, the combination of lyso-SM-509, lyso-Gb3, may comprise a biomarker. Thus, a "biomarker" may comprise one, two, three, four, five, six, seven, eight, nine, ten, fifteen, twenty, twenty-five, thirty, or more, biological compounds.

The determination of the plasma levels of a biomarker in a subject can be performed using any of the many methods known in the art, e.g., using HPLC-MS/MS or LysoTracker® technology. Any method known in the art for quantitating specific LSD-related biomarkers in a subject or a biological sample may be used in the methods of the disclosure.

The term "biological sample" as used herein refers any tissue or fluid from a subject that is suitable for detecting a biomarker, such as lyso-SM-509 plasma levels. Examples of useful biological samples include, but are not limited to, biopsied tissues and/or cells, e.g., solid tumor, lymph gland, inflamed tissue, tissue and/or cells involved in a condition or disease, blood, plasma, serous fluid, cerebrospinal fluid, saliva, urine, lymph, cerebral spinal fluid, and the like. Other suitable biological samples will be familiar to those of ordinary skill in the relevant arts. A biological sample can be analyzed for biomarker expression and/or mutation using any technique known in the art and can be obtained using techniques that are well within the scope of ordinary knowledge of a clinical practioner. In one embodiment of the disclosure, the biological sample comprises blood cells.

The present disclosure provides the following particular embodiments with respect to personalized medicine for subjects having a LSD:

Embodiment I: A method of treating a subject having a LSD, the method comprising administering a therapeutically effective amount of a Compound of the Disclosure to the subject, wherein cells of the subject contain an elevated concentration or a decreased concentration of a LSD-related biomarker.

Embodiment II: A method of treating a subject having a LSD, the method comprising:

(a) determining the concentration of a LSD-related biomarker in a biological sample from the subject, and when the concentration is determined to be higher than that of a control sample, e.g., a sample from a normal undiseased subject, or lower than that of a control sample; and (b) administering to the subject a therapeutically effective amount of a Compound of the Disclosure.

Embodiment III: A method for treating a LSD in a subject having an elevated concentration or decreased concentration of a LSD-related biomarker, the method comprising administering to the subject a therapeutically effective amount of a Compound of the Disclosure.

The present disclosure provides the following particular embodiments with respect to personalized medicine for subjects having a neurodegenerative disease:

Embodiment I: A method of treating a subject having a neurodegenerative disease, the method comprising administering a therapeutically effective amount of a Compound of the Disclosure to the subject, wherein cells of the subject contain an elevated concentration or a decreased concentration of a neurodegenerative disease-related biomarker.

Embodiment II: A method of treating a subject having a LSD, the method comprising:

(a) determining the concentration of a neurodegenerative disease-related biomarker in a biological sample from the subject, and when the concentration is determined to be higher than that of a control sample, e.g., a sample from a normal undiseased subject, or lower than that of a control sample; and (b) administering to the subject a therapeutically effective amount of a Compound of the Disclosure.

Embodiment III: A method for treating a neurodegenerative disease in a subject having an elevated concentration or decreased concentration of a neurodegenerative disease-related biomarker, the method comprising administering to the subject a therapeutically effective amount of a Compound of the Disclosure.

The present disclosure provides the following particular embodiments with respect to personalized medicine for subjects having a migraine, and the symptoms associated therewith:

Embodiment I: A method of treating a subject having a migraine, and the symptoms associated therewith, the method comprising administering a therapeutically effective amount of a Compound of the Disclosure to the subject, wherein cells of the subject contain an elevated concentration or a decreased concentration of a migraine-related biomarker.

Embodiment II: A method of treating a subject having a migraine, and the symptoms associated therewith, the method comprising:

(a) determining the concentration of a migraine-related biomarker in a biological sample from the subject, and when the concentration is determined to be higher than that of a control sample, e.g., a sample from a normal undiseased subject, or lower than that of a control sample; and (b) administering to the subject a therapeutically effective amount of a Compound of the Disclosure.

Embodiment III: A method for treating a migraine, and the symptoms associated therewith in a subject having an elevated concentration or decreased concentration of a migraine-related biomarker, the method comprising administering to the subject a therapeutically effective amount of a Compound of the Disclosure.

The present disclosure provides the following particular embodiments with respect to personalized medicine for subjects in need of improving mobility:

Embodiment I: A method of treating a subject in need of improving mobility, the method comprising administering a therapeutically effective amount of a Compound of the Disclosure to the subject, wherein cells of the subject contain an elevated concentration or a decreased concentration of a mobility-related biomarker.

Embodiment II: A method of treating a subject in need of improving mobility, the method comprising:

(a) determining the concentration of a mobility-related biomarker in a biological sample from the subject, and when the concentration is determined to be higher than that of a control sample, e.g., a sample from a normal undiseased subject, or lower than that of a control sample; and (b) administering to the subject a therapeutically effective amount of a Compound of the Disclosure.

Embodiment III: A method for improving mobility in a subject having an elevated concentration or a decreased concentration of a mobility-related biomarker, the method comprising administering to the subject a therapeutically effective amount of a Compound of the Disclosure.

The present disclosure provides the following particular embodiments with respect to personalized medicine for subjects in need of improving cognitive function:

Embodiment I: A method of treating a subject in need of improving cognitive function, the method comprising administering a therapeutically effective amount of a Compound of the Disclosure to the subject, wherein cells of the subject contain an elevated concentration or a decreased concentration of a cognitive function-related biomarker.

Embodiment II: A method of treating a subject in need of improving cognitive function, the method comprising:

(a) determining the concentration of a cognitive function-related biomarker in a biological sample from the subject, and when the concentration is determined to be higher than that of a control sample, e.g., a sample from a normal undiseased subject, or lower than that of a control sample; and (b) administering to the subject a therapeutically effective amount of a Compound of the Disclosure.

Embodiment III: A method for improving cognitive function in a subject having an elevated concentration or a decreased concentration of a cognitive function-related biomarker, the method comprising administering to the subject a therapeutically effective amount of a Compound of the Disclosure.

EXAMPLES

Example 1

General Preparation of Deuterated N-Acetyl-Leucine (D-Enantiomer, L-Enantiomer and D,L-Mixtures)

A wide variety of methods can be used to selectively replace one or more hydrogen atoms in leucine with deuterium ("D" or "2H"). Such compounds can be prepared wherein at each position D has an isotopic enrichment of 90% or more. One general method involves deuterating leucine and then converting it to the N-acetyl form. In some instances, the N-acetyl form can be deuterated, e.g., "labelled," directly. The methods are general for D-, L- and D,L-mixtures unless specified otherwise. See, e.g., Yamauchi et al., *Biosci. Biotechnol. Biochem.* 70:276-278 (2006); Kelly et al., *Nat. Prod. Rep.* 14:205-219 (1997); August et al., *Tetrahedron Lett.* 33:4617-4620 (1992); Oba et al., *Tetrahedron Lett.* 39:1595-1598 (1998); Hill et al., *Can. J. Chem.* 72:110-113 (1994); Kelly et al., *Tetrahedron Lett.* 36:8315-8318 (1995); and Fletcher et al., *J. Chem. Soc., Perkin Trans. I*, 43-52 (2000).

Example 2

Preparation of Compounds Based on D-Leucine

The synthesis of D-leucine and its labelled analogs can be achieved via reductive amination of 2-oxo-4-methylvaleric acid with D-amino acid dehydrogenase (DAADH).

A reaction mixture (1 mL) containing 100 mM glycine-KOH (pH 10.5), 5.0 mM NADPH, 70 mM $NH_4Cl$, 5.0 mM 2-oxo acid (sodium salt), and 2.9 mg DAADH is incubated at 50° C. for 1 h while keeping pH at 10.5 by addition of 1.0 M KOH solution. The pH value is measured using pH meter. The reaction is terminated by adding trichloroacetic acid to a final concentration of 10%. After clarifying the mixture by centrifugation and filtration, the D-leucine produced can be separated and purified on a reversed-phase column and detected using a fluorometric detector (excitation at 350 nm and detection at 450 nm). Alternatively, a regenerating system for NADPH can be used with glucose dehydrogenase (GDH) in a reaction mixture (1 mL) containing 100 mM glycine-KOH (pH 10.5), 1.0 mM NADPH or NADP+, 20 mM glucose, 70 mM $NH_4Cl$, 5.0 mM 2-oxo acid, 2.9 mg DAADH, and 0.32 mg. GDH is incubated at 50° C. for 1 h while keeping pH at 10.5 by addition of 1.0 M KOH solution. D-leucine is separated and purified as described above. The above reactions can be conducted in deuterium dioxide to incorporate D into on the alpha carbon. DAADH catalyzes the production of D-amino acids from the corresponding 2-oxo acids in the presence of ammonia and results in excellent yields (>99%) and high enantioselectivity (>99%). (Akita et al., *Biotechnol Lett* 34:1693 (2012) and Akita et al., *Biotechnol Lett* 36: 2245 (2014)).

Example 3

Method for Conversion of Racemic Leucine to the L-Enantiomer

Racemic amino acids may be resolved to their L- and D-enantiomers by enzymatic or chemical procedures. A general method for the conversion of racemic amino acids to homochiral products has been reported that uses an oxidase-aminotransferase coupled system (Shah et al., *Tetrahedron Lett.* 35:29-32 (1994)). This method can be used for the production of L-leucine from the racemate by means of D-amino acid oxidase (EC 1.4.3.3), catalase (EC 1.11.1.6), leucine dehydrogenase (EC 1.4.1.9), and formate dehydrogenase (EC 1.2.1.2), D-leucine is fully converted to the L-enantiomer in situ through an achiral intermediate, α-oxo-γ-methylthio-butyrate, in an enzymatic system containing oxygen, $NAD^+$, and ammonium formate. Leucine dehydrogenase catalyses the reversible deamination of various aliphatic L-amino acids including methionine to their α-oxo analogues in the presence of $NAD^+$. The reaction is favourable for reductive amination, which is accelerated by combination with the formate dehydrogenase reaction. Formate dehydrogenase catalyses the irreversible oxidation of formate to $CO_2$ with concomitant reduction of NAD+ to NADH. α-oxo acids are spontaneously decarboxylated by oxidation with $H_2O_2$.

The reaction mixture contains DL-leucine (100 μmol), NADH (1 μmol), ammonium chloride (25 μmol), sodium formate (500 μmol), Tris-HCl buffer (pH 8.5; 100 μmol), D-amino acid oxidase from Sigma (5 units), catalase from Sigma (2 units), leucine dehydrogenase from *Clostridium thermoaceticum* AN 28-4 (10 units), and formate dehydrogenase from Boehringer (2 units) in a final volume of 1 mL at 37° C. and pH 8.0-8.5. After incubation for 10 h, HCl is added to the reaction mixture to a final concentration of 1.0 M. The solution is applied to a Dowex 50($H^+$) column (1×10 cm), and L-leucine is eluted with 1 M $NH_4OH$. The fractions containing L-leucine are pooled and concentrated to a small volume, followed by evaporation to dryness under reduced pressure. The residue is dissolved in a small volume of hot 80% ethanol, and L-leucine is crystallized at 4° C. Using this method, DL-leucine (0.1 M) can be converted to the L-enantiomer (95% yield; 99% e.e. in 2 h) based on separation with an enantioselective HPLC with a Daicel Crown pack column (0.4 i.d.×50 cm). (Nakajima et al., *J. Chem. Soc., Chem. Commun.* 13: 947-948 (1990)).

Example 4

Preparation of N-Acetylated Versions of Deuterated Leucine Analogues

Methods for the N-acetylation of amines and alpha-amino acids including leucine are widely reported. The deuterated leucine analogues synthesized by the methods reported above are not N-acetylated from the method described, the resulting deuterated leucine analogues will be N-acetylated by one of the methods described below. In one method described, the acetylating agent is acetic acid that proceeds as follows: $(CH_3CO)_2O+H_2N—CH(R)—COOH \rightarrow CH_3CONH—CH(R)—COOH+CH_3COOH$. This reaction is conducted in an acetic acid environment or in a mixture of water with pyridine. The acetylation of L-leucine and D-leucine by acetic anhydride proceed efficiently in aqueous solutions of the starting compounds on heating the reaction mixes from 50-70° C. The optimum molar ratio of amino acid to acetic anhydride is 1.25-1.5. Acetylation products can be crystallized from aqueous solution on cooling forming the monohydrate with yields of 75-80%. Distilled water (760 mL) is placed in a glass rector fitted with a stirrer and a thermometer and L-leucine (14.0 mol) is added in portions with stirring and heating to 50-55° C. and the mixture is stirred to complete dissolution. Acetic anhydride (1980 mL, 21.0 mol) is added through the dropper funnel over 2.0-2.5 h. This is added at such a rate that the temperature of the mixture did not exceed 70° C. The reaction is then heated to 70° C. for 0.5 h and left for crystallization to occur on cooling. The reaction mix is mixed for 40 min, after which hydrochloric acid (1060 ml, 37%) is added dropwise to pH 2.0-2.5. The resulting precipitate is collected by filtration, washed on a filter with iced water followed by alcohol, and dried at 50-60° C., then in air at 25-30° C. Anhydrous product is obtained by drying in vacuo at 85° C. to constant weight. A further 360 g of product is obtained after evaporation of aqueous acetic acid from the mother liquor in a rotary evaporator at a bath temperature of 70° C.

Example 5

Preparation of Compounds Deuterated on the Alpha Carbon (C-2)

A preparation for labelling the α position of amino acids starting from commercially available amino acids has been reported that is rapid, inexpensive, and generally applicable, and shown to be effective for leucine (Upson and Hruby, *J. Org. Chem.* 42:2329-2330 (1977)). In this method, leucine is refluxed in acetic acid and acetic anhydride to give racemic N-acetyl leucine. A mixture of excess acetic anhydride with $D_2O$ is used to give a solution of $Ac_2O$ in AcOD. Treatment of amino acids with this solution at reflux for a few minutes leads to acylation, racemization, and exchange at the α position. The N-acetyl-leucine is then the starting compound for enzymatic resolution using hog renal acylase, carboxypeptidase, or other enzymes capable of selective cleavage of an acetyl group from one stereoisomer without a significant cleavage of the enantiomeric compound. To achieve high levels of exchange, a high 2H/1H ratio is required. This condition can be approached in several ways: (a) a high molar excess of acetic acid-d relative to the amino acid can be used; (b) labile hydrogens of the amino acid can be subjected to prior exchange; (c) the exchange reaction can be repeated. One treatment leads to 83% exchange, and a second treatment raises the level of exchange to 91%.

All-protio leucine (0.01 mol) is shaken with 3.7 mL of $D_2O$ to exchange labile protons. The mixture is frozen and lyophilized to dryness. Immediately, 21.7 mL of $Ac_2O$ and 2.5 mL of $D_2O$ are added to the resulting powder and the flask is placed in a 170° C. bath. The solution is refluxed for 2 min, then cooled (drying tube) and 2 mL of $D_2O$ is added to destroy the remaining $Ac_2O$ and convert any azlactone back to the N-acetyl leucine. The solvents are removed by rotary evaporation. α hydrogens are detectable by proton nuclear magnetic resonance spectroscopy, yield (80%).

In another example, leucine dehydrogenase can be used to catalyse the exchange of the α-proton so, when the reaction is conducted in $^2H_2O$, L-[2-$^2$H] leucine could be prepared. Deuteriation is also extended to the β-position by pre-exchanging the α-keto acid in $^2H_2O$-base prior to the enzymatic transformations. This methodology enables the synthesis of a variety of isotopically labelled α-amino acids, including [2,3,3-$^2H_3$]Leucine on a gram scale. A formate dehydrogenase (FDH) catalysed system can be used to recycle NADH to prepare leucine from its α-keto acid and leucine dehydrogenases. Formate dehydrogenase catalyses the oxidation of formate ions to carbon dioxide and releases hydride ions which react with NAD+, thus driving the reversible reductive amination reaction in the required direction. Additionally, A general method for the conversion of racemic amino acids to homochiral products has been reported using an oxidase-aminotransferase coupled system. (Kelly et al., *Tetrahedron Lett.* 37:1517-1520 (1996) and Kelly et al., *Nat. Prod. Rep.* 14:205-219 (1997)).

In another method, transformations based upon enzyme catalysis have proved valuable for the preparation of a series of α-deuteriated L-amino acids including leucine ((Kelly et al., *Tetrahedron Lett.* 37:1517-1520 (1996)). The approach involves incubation of an unlabelled L-amino acid in $D_2O$ with lyophilised *E. coli* B/It7-A cells abundant in tryptophanase. The relatively broad substrate specificity enables the preparation of a range of α-deuteriated L-amino acids. including leucine, in reasonable yields (43-95%).

In another method, racemic [2-$^2$H]amino acids were prepared by heating the corresponding amino acid with 0.05 equiv. of benzaldehyde in deuteriated acetic acid (Kelly et al., *Tetrahedron Lett.* 37:1517-1520 (1996)). Conversion of the acid to the methyl ester followed by an alcalase catalysed resolution gave the homochiral amino acid with >99% incorporation of deuterium.

In another method, to synthesize α-deuteriated α-amino acids chiral auxiliaries and templates are used (Rose et al., *J. Chem. Soc., Perkin Trans.* 1, 157-165 (1995)). Specifically, base catalysed deuteriation of Schöllkopf's bis-lactim ethers, (3R)- or (3S)-3-isopropyl-2,5-dimethoxy-3,6-dihydro-pyrazine, in refluxing MeO$^2$H-$^2$H$_2$O gives the [6-$^2$H$_2$] isotopomer 9 without disturbing the stereogenic centre at C-3.

A ruthenium-catalyzed selective α-deuteration of amino acids has been demonstrated by Chatterjee et al., *Org. Lett.* 18:5892-5895 (2016). The high deuterium incorporation, selectivity for α-$CH_2$ protons to the amine functional group and low loadings of catalyst make this protocol attractive and advantageous for both laboratory and large-scale preparation of amino acids. Complex 1 can be used to efficiently label amino acids including leucine. A series of amino acids were subjected to catalysis by using deuterium oxide, including leucine. See Table 3 of Chatterjee et al., *Org. Lett.* 18:5892-5895 (2016).

Example 6

Preparation of Compounds Deuterated on the Beta Carbon (C-3)

The aminotransferase-catalysed exchange of the alpha-proton with deuterium described in the section above, can also be used to incorporate deuterium into the beta-position by pre-exchanging the alpha-keto acid in $^2$H$_2$O-base prior to the enzymatic transformations as described by Kelly et al., *Tetrahedron Lett.* 37:1517-1520 (1996). In another method, the prochiral beta-methylene groups of certain can be exchanged using the enzyme cystathionine gamma-synthase, which is suitable for preparing multigram quantities of homochiral deuterated L-leucine (Homer et al., *Anal Biochem.* 215:211-215 (1993). The reaction is conducted in a buffer of 33 mM $Na_2HPO_4$, 17 mM $KH_2PO_4$, 1 mM EDTA and 0.2 mM pyridoxal phosphate in $^2$H$_2$O, pH 7.2. After pre-exchanging solvent-exchangeable protons in $^2$H$_2$O, L-leucine (20 mg/mL) is incubated with cystathionine gamma-synthase at 37° C. for three days in the dark. The product [2S, 3R-$^2$H$_2$]leucine is then isolated by standard procedures. To stereoselectively label the prochiral beta-methylene groups of L-leucine, a combined chemical-enzymatic approach can be used as an variation of that reported for the synthesis of L-threo- and L-erythro-[1-$^{13}$C, 2,3_$^2$H$_2$] amino acids, including leucine (Oba et al., *Tetrahedron Lett.* 39:1595-1598 (1998); Oba et al., *J. Chem. Soc., Perkin Trans.* 1, 1603-1609 (1995)). Stereoselective incorporation of deuterium into the α,β-positions of protected amino acid is accomplished by catalytic deuteration of dehydroamino acid derivatives and is followed by a resolution with acylase giving good yields of the L-threo-[2,3-$^2$H$_2$]amino acids. For the L-erythro isomers it is then necessary to racemize the remaining D-threo isomer (from the initial resolution) and then to conduct a further resolution. This approach can be extended to stereospecifically label with deuterium combinations of the beta-methylene and pro-chiral delta-methyl groups.

Example 7

Preparation of Compounds Deuterated on the Gamma Carbon (C-4)

This chemo-enzymatic approach described for labelling the delta carbons of L-leucine with deuterium described in detail below (Fletcher et al., *J. Chem. Soc., Perkin Trans.* 1, 43-51 2000) can be used in the synthesis of leucine analogues with deuterium at the gamma carbon (C-4). This can be achieved by using sodium [$^2$H]acetate as the source of isotopic label. For example, treatment of sodium [2-$^2$H] acetate with pivaloyl chloride gives a mixed anhydride which on reaction with the lithium salt of 1 gives the acylated product 12 in 70% yield, the precursor to [4-$^2$H]-L-leucine.

Example 8

Preparation of Compounds Deuterated on the Delta Carbons (C-5)

Strategies for the stereo-selective syntheses of leucine and valine with deuterium labelled methyl groups have been reported.

In one method, (Hill et al., *Canadian Journal of Chemistry* 72:10-113 (1994)) (R)-Pulegone 1 is converted to (R)-citronellic acid 2 (R=H) by the published procedure. See Scheme 1. Reduction of the methyl ester 2 (R=$CH_3$) with lithium aluminum deuteride gives citronellol-1,1-d$_2$ 3, which can be oxidized by pyridinium chlorochromate to citronellal-1-d 4. The acidic hydrogens at C-2 are exchanged for deuterium by several exchanges with $Na_2CO_3$ in $D_2O$-$CH_3OD$, leading to citronellal-1,2,2-d3 5. Decarbonylation of the aldehyde is achieved with Wilkinson's catalyst, affording (6S)-[7,7,7-$^2$H$_3$]-2,6-dimethyl-2-heptene 6, in which the pivotal asymmetric centre containing methyl and trideuteriomethyl has been introduced with unambiguous configuration and conservation of the enantiomeric purity of pulegone. The double bond of 6 is oxidized by the Lemieux-Rudloff procedure (10) to (4s)-[5,5,5-2~3]-4-methylpentanoic acid 7. The amino group is introduced in the usual way by α-bromination followed by ammonolysis, and the amino acid is resolved by hog kidney acylase-catalyzed hydrolysis of the N-acetyl derivative 9. This reaction yielded the (2S,4S) diastereomer 10 of leucine-5-d$_3$, and acid hydrolysis of the recovered amide 11 gave the (2R,4S) diastereomer 12.

Scheme 1
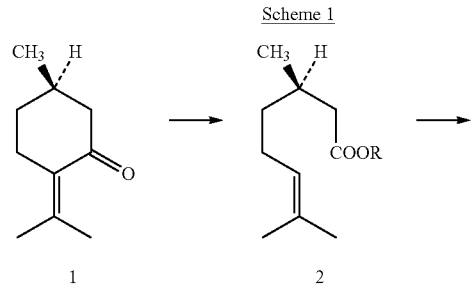
1    2
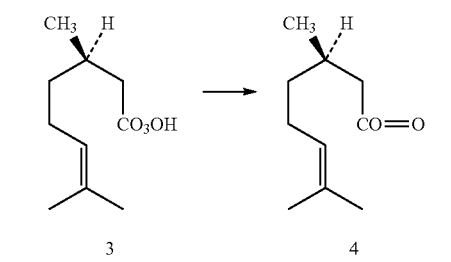
3    4
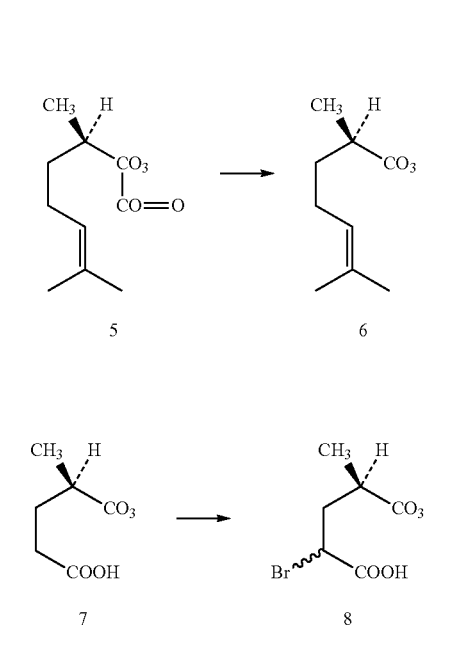
5    6
7    8
9    10
11    12
-continued
SCHEME 2. Conversion of (R)-pulegone to leucine-$d_3$.
Fig. 1 Fischer projections of labeled leucines.
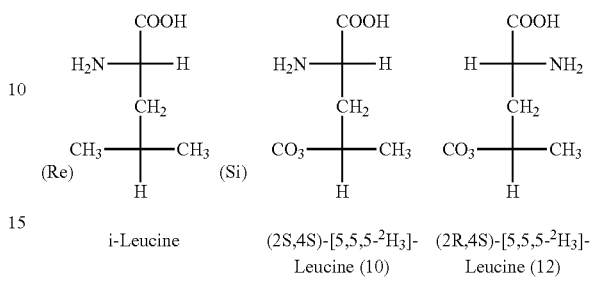
i-Leucine  (2S,4S)-[5,5,5-$^2$H$_3$]-  (2R,4S)-[5,5,5-$^2$H$_3$]-
            Leucine (10)              Leucine (12)
Example 9
Synthesis of Acetyl-leucine-2,3,3,4-$d_4$ and Acetyl-L-leucine-2,3,3,4-$d_4$
Scheme 2
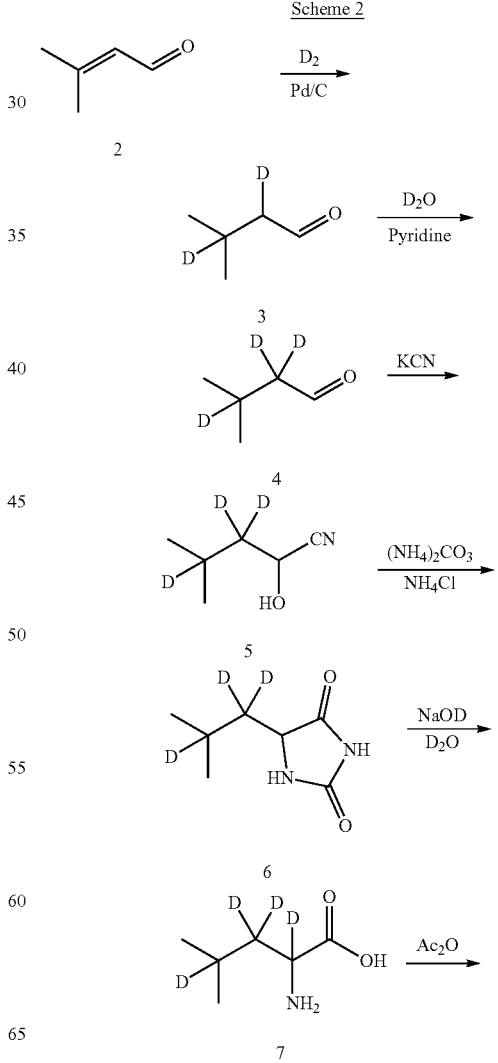

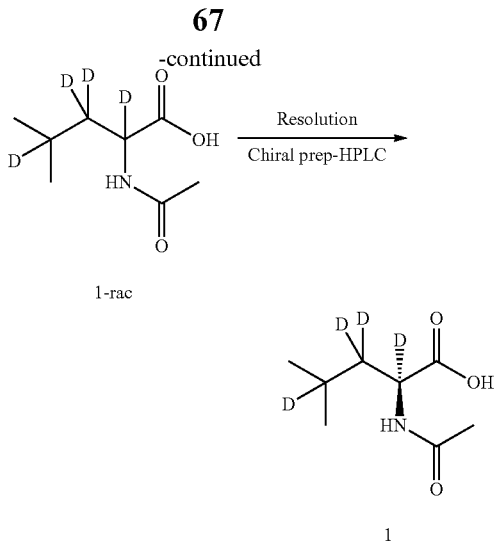

Step 1: 3-Methylbutanal-2,3-$d_2$ (3)

To a mixture of palladium on carbon (1 g, 0.08 Eq, 9 mmol) in deuterium oxide (50 mL), 3-methylbut-2-enal 2 (10.0 g, 11.5 mL, 1 Eq, 119 mmol) was added at room temperature. The equipment was evacuated 2 times and charged with $D_2$ gas using a deuterium filled balloon. The reaction mixture was stirred at room temperature while monitoring conversion by GC-MS. After 7 days GC-MS showed nearly complete consumption of the starting material (<2% remaining). The Pd/C was removed by filtration over Celite. The flask and filter were washed with $D_2O$ (3×4 mL). The filtrate and washings were combined and the solution of 3-methylbutanal-2,3-$d_2$ (3) in $D_2O$ was used as such in the next step. The structure of (3) was confirmed by $^1H$ NMR and GC-MS.

Step 2: 3-Methylbutanal-2,3,3-$d_3$ (4)

The crude 3-methylbutanal-2,3-$d_2$ (3) (119 mmol) in $D_2O$ (29861-24) was poured into a pressure tube. Pyridine (941 mg, 0.96 mL, 0.1 Eq, 11.9 mmol) was added and the mixture was heated at 130° C. in the closed pressure tube overnight. $^1$H-NMR analysis showed partial H/D exchange. The mixture was heated for 5 more days after which full deuterium incorporation was observed. The resulting solution of 3-methylbutanal-2,3,3-$d_3$ (4) in $D_2O$/pyridine was used as such in the next step. The structure of (4) was confirmed by $^1H$ NMR.

Step 3: 2-Hydroxy-4-methylpentanenitrile-3,3,4-$d_3$ (5)

The crude solution of 3-methylbutanal-2,3,3-$d_3$ (4) (in $D_2O$ with 0.1 eq of pyridine) was cooled to 10° C. and sodium metabisulfite (11.73 g, 61.69 mmol) was added in small portions. After nearly all solid dissolved, the mixture was cooled to 4-5° C. and potassium cyanide (7.305 g, 1 Eq, 112.2 mmol) was added in portions. The mixture was stirred at room temperature for 2 h. The product was extracted with ethyl acetate (3×). The combined organic phases were dried over $Na_2SO_4$, filtered and concentrated in vacuo to afford 2-hydroxy-4-methylpentanenitrile-3,3,4-$d_3$ (5) as an orange oil (4.8 g, 41 mmol). The material contained an impurity but was used as such in the next step. The structure of (5) was confirmed by $^1H$ NMR.

Step 4: 5-(2-Methylpropyl-1,1,2-d3)imidazolidine-2,4-dione (6)

Finely powdered ammonium carbonate (9.3 g, 2.33 Eq, 96 mmol) was added to deuterium oxide (15 mL) and stirred until nearly all solids dissolved. The crude 2-hydroxy-4-methylpentanenitrile-3,3,4-$d_3$ (5) (4.8 g, 1 Eq, 41 mmol) was transferred to the reaction mixture with the aid of THF (15 mL). The mixture was heated at 100° C. in a sealed tube overnight. Volatiles (THF) were removed in vacuo leaving a suspension in deuterium oxide. The solids were isolated by filtration consisting of mainly the desired hydantoin 6 (2.6 g). The solids were triturated in DCM (10 mL) to afford 1.5 g of 6 as a yellowish solid with an impurity. Based on $^1$H-NMR spectrum incorporation of deuterium at the alpha position to the carbonyl was 60%.

Step 5: Acetyl-leucine-2,3,3,4-$d_4$ (1-rac)

5-(2-Methylpropyl-1,1,2-d3)imidazolidine-2,4-dione (6) (1.5 g, 1 Eq, 9.4 mmol) was suspended in a 40% solution of sodium deuteroxide in $D_2O$ (21 g, 15 mL, 1 Eq, 9.4 mmol) and heated at reflux for 72 h. The mixture was neutralized with DCl (20% in $D_2O$). To the neutralized mixture acetic anhydride (3.8 g, 3.6 mL, 4 Eq, 38 mmol) was added and the reaction mixture was stirred at room temperature overnight. The solids were filtered off and extracted with THE to afford 220 mg of product with impurities. The aqueous filtrate was extracted with THE to afford 900 mg of product. The remaining aqueous phase was concentrated to dryness and the residue was extracted with THE to afford an additional 120 mg of product. All product batches were combined and precipitated from EtOAc affording 330 mg of product with some inorganic impurities. The mother liquor was treated with dichloromethane affording an additional 300 mg of product. Both precipitated product fractions were combined affording 630 mg of material that was flushed over a small plug of silica gel using MeOH in DCM to remove inorganic impurities. This furnished 430 mg (9.4 mmol, 29%) of rac-acetyl-leucine-2,3,3,4-$d_4$ (1-rac) with >98% purity (ELSD). The structure of (1-rac) was confirmed by $^1H$ NMR and LCMS.

Step 6: Acetyl-L-leucine-2,3,3,4-$d_4$ (1)

Chiral resolution of acetyl-leucine-2,3,3,4-$d_4$ (1-rac) was performed using chiral preparative HPLC. The concentrated fractions from this separation contained ammonium salt of acetyl-L-leucine-2,3,3,4-$d_4$. This salt was removed by lyophilization. From 1.0 g of 1-rac both, acetyl-L-leucine-2,3,3,4-$d_4$ (320 mg) and acetyl-D-leucine-2,3,3,4-$d_4$ (340 mg) were isolated. Acetyl-L-leucine-2,3,3,4-$d_4$ (1) had a purity of 99.6% (ELSD) and an optical purity of 97% ee.

Example 10

Synthesis of Acetyl-leucine-2,3,3-$d_3$ and Acetyl-L-leucine-2,3,3-$d_3$

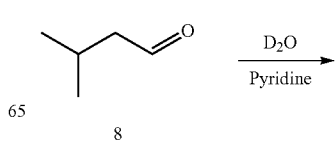

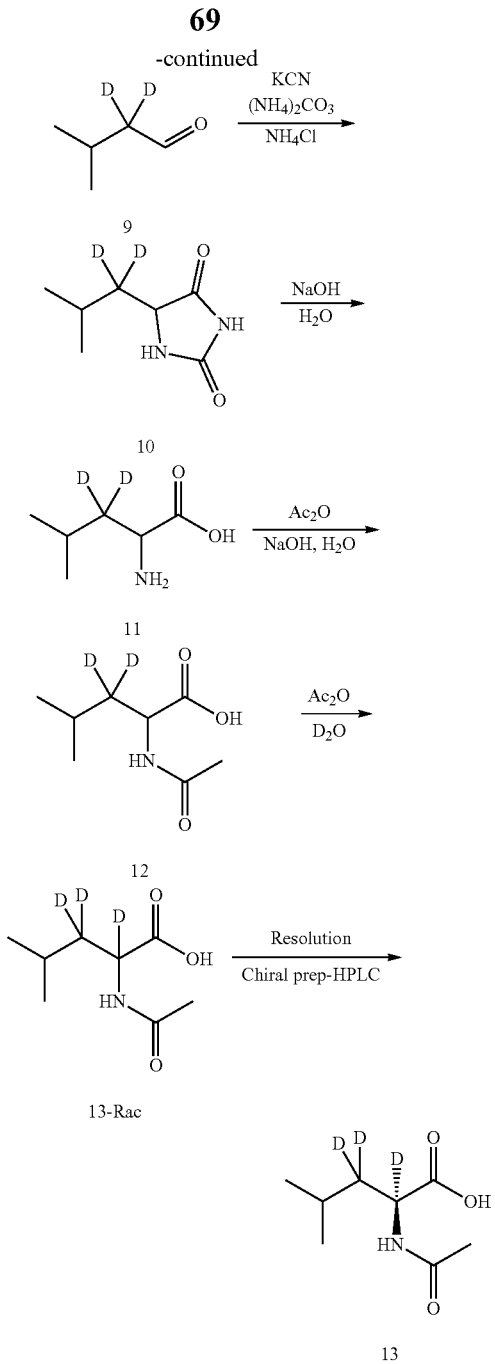

Acetyl-leucine-2,3,3-$d_3$ and acetyl-L-leucine-2,3,3-$d_3$ and can be prepared using the methodology described in EXAMPLE 9.

Example 11

Measuring Lysosomal Volumes with Flow Cytometry

The technique applied in the present study is described in te Vruchte et al., *J. Clin. Invest.* 3:1320-1328 (2014). Briefly, human fibroblasts from patients with Tay-Sachs Disease, AB Variant were purchased from the NINDS Human Genetic Repository at the Coriell Institute, 403 Haddon Avenue, Camden, N.J., 08103, USA. Fibroblasts or Chinese Hamster Ovary cells were grown in T75 culture flasks, treated for 7 days with compounds, trypsinized, centrifuged (180 g, 5 min), washed twice with 1×PBS, centrifuged again and were stained with 1 ml of 100 nM LysoTracker-green DND-26 (Invitrogen) in PBS (10 min, in dark). Following incubation, cells were centrifuged (800 g, 5 min), resuspended in 0.5 ml of FACS buffer (0.1% BSA, 0.02 M $NaN_3$ in 1×PBS) and kept on ice for a maximum of 1 h prior to flow cytometric analysis (BD Biosciences FACSCanto II or Accuri C6 Plus). The cytometer was calibrated using Cytometer Setup and Tracking beads (BD), and compensation was performed using cells stained with Lysotracker or Propidium Iodide using BD FACSDiva software (BD) or BD Accuri C6 Plus software (BD).

Figure 2:
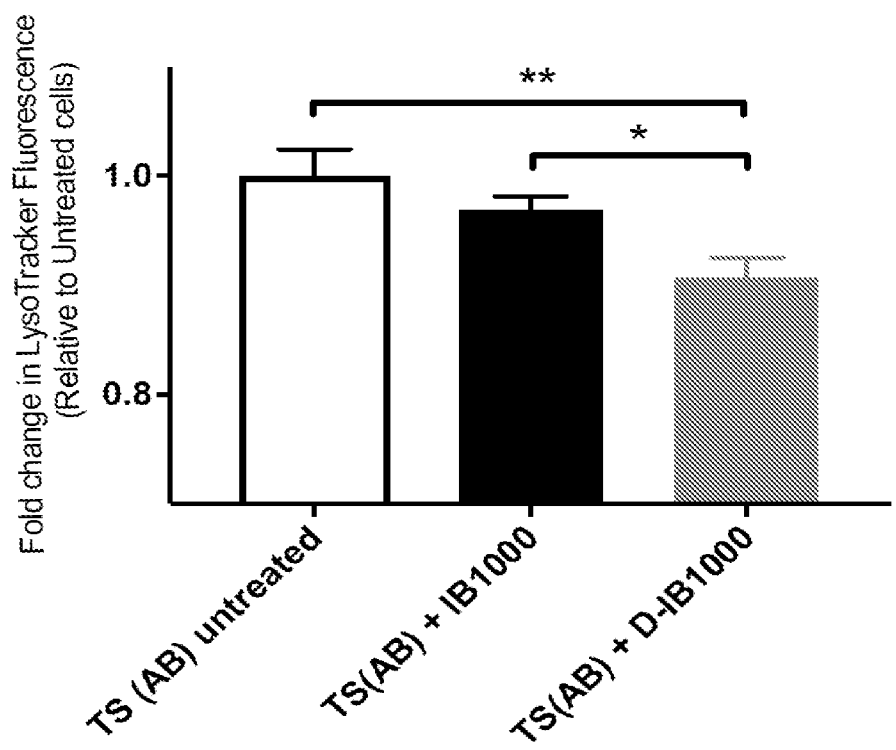
FIG. 2 is bar graph showing the effect of acetyl-leucine (referred to as IB1000) and acetyl-leucine-2,3,3,4-$d_4$ (referred to as DIB1000) in a Tay-Sachs AB human fibroblast cell assay. Tay-Sachs, AB Variant patient-derived fibroblast cells were treated with 1 mM acetyl-leucine or acetyl-leucine-2,3,3,4-$d_4$ to compare LysoTracker signals. Untreated; 1.00±0.02, n=3, Acetyl-leucine; 0.97±0.01, n=3, Acetyl-leucine-2,3,3,4-$d_4$; 0.91±0.02, n=3. One-way ANOVA was conducted for statistical analysis. */**$p<0.003/0.02$.
Figure 3:
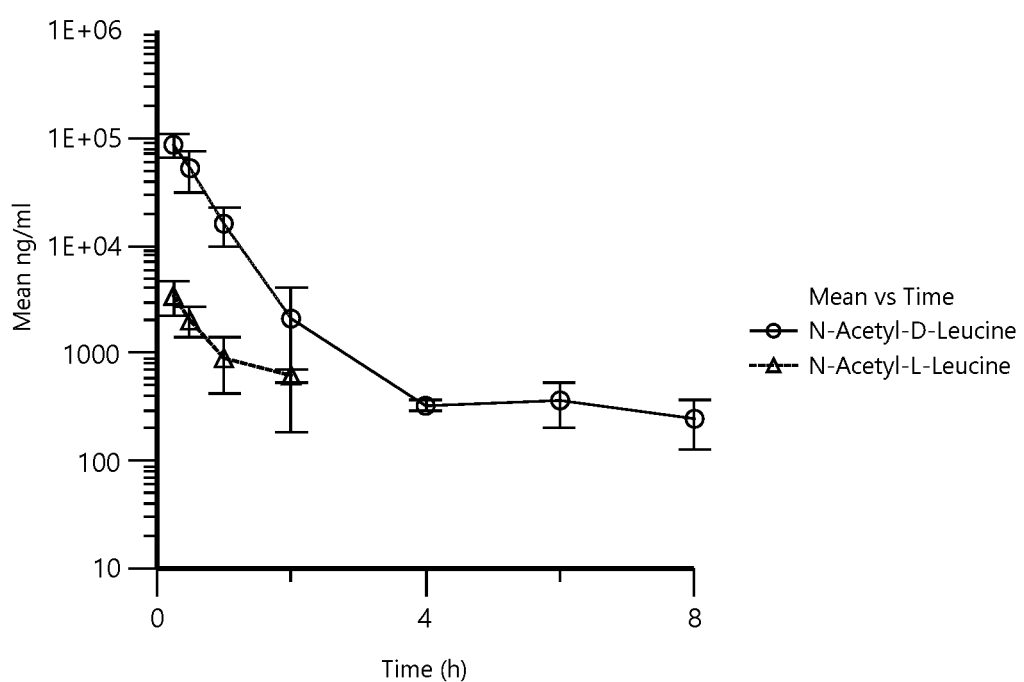
FIG. 3 is a line graph showing the plasma concentration vs. time profile for acetyl-D-leucine (referred to as N-acetyl-D-leucine) and acetyl-L-leucine (referred to as N-acetyl-L-leucine) after p.o. administration of acetyl-leucine (referred to as N-acetyl-DL-leucine) to male BALB/c mice a dose of 100 mg/kg in saline.
Figure 4:
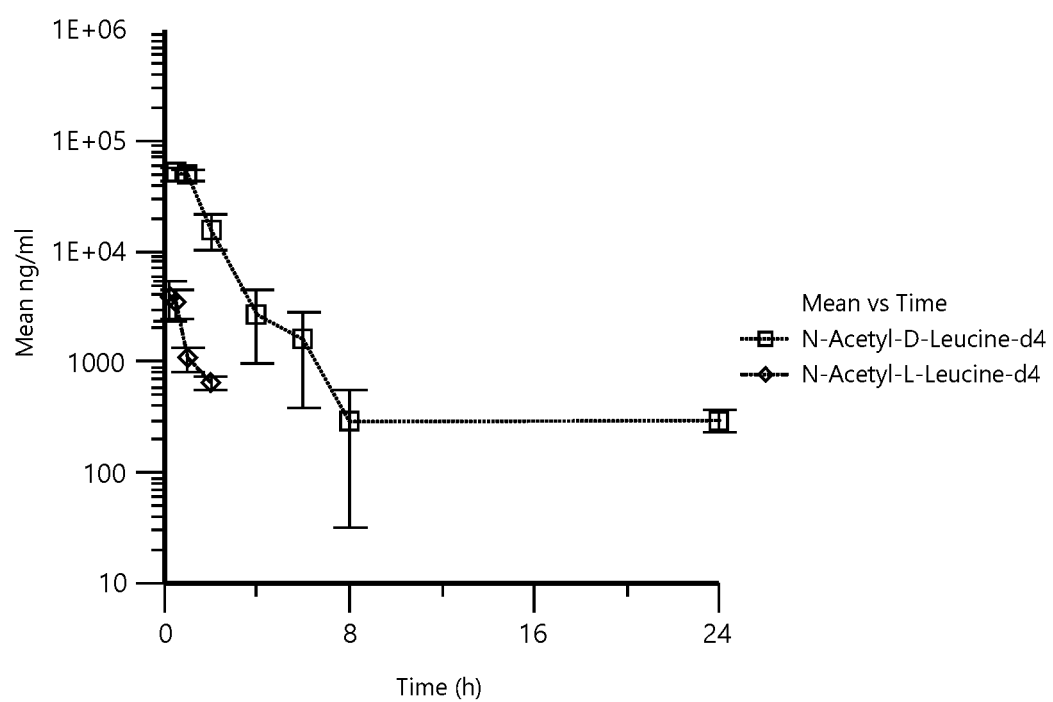
FIG. 4 is a line graph showing the plasma concentration vs. time profile for acetyl-D-leucine-2,3,3,4-$d_4$ (referred to as N-acetyl-D-leucine-$d_4$) and acetyl-L-leucine-2,3,3,4-$d_4$ (1) (referred to as N-acetyl-L-leucine-$d_4$) after p.o. administration of acetyl-leucine-2,3,3,4-$d_4$ (1-rac) (referred to as N-acetyl-DL-leucine-$d_4$) to male BALB/c mice a dose of 100 mg/kg in saline.
Figure 5:
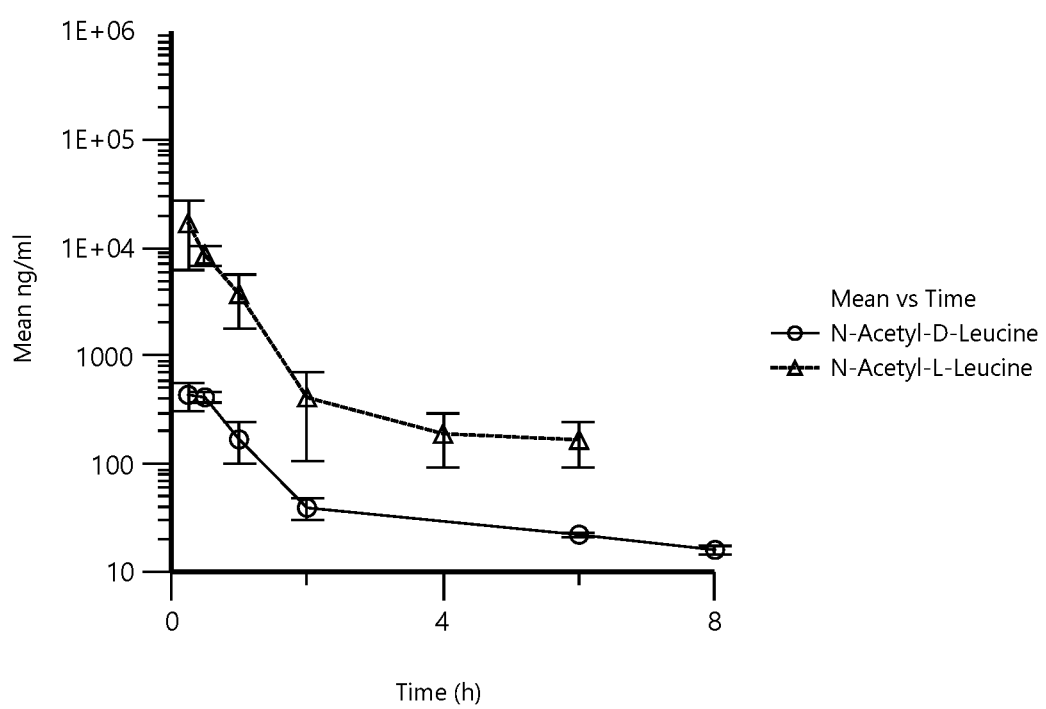
FIG. 5 is a line graph showing the plasma concentration vs. time profile for acetyl-D-leucine (referred to as N-acetyl-D-leucine) and acetyl-L-leucine (referred to as N-acetyl-L-leucine) after p.o. administration of acetyl-L-leucine to male BALB/c mice a dose of 100 mg/kg in saline.
Figure 6:
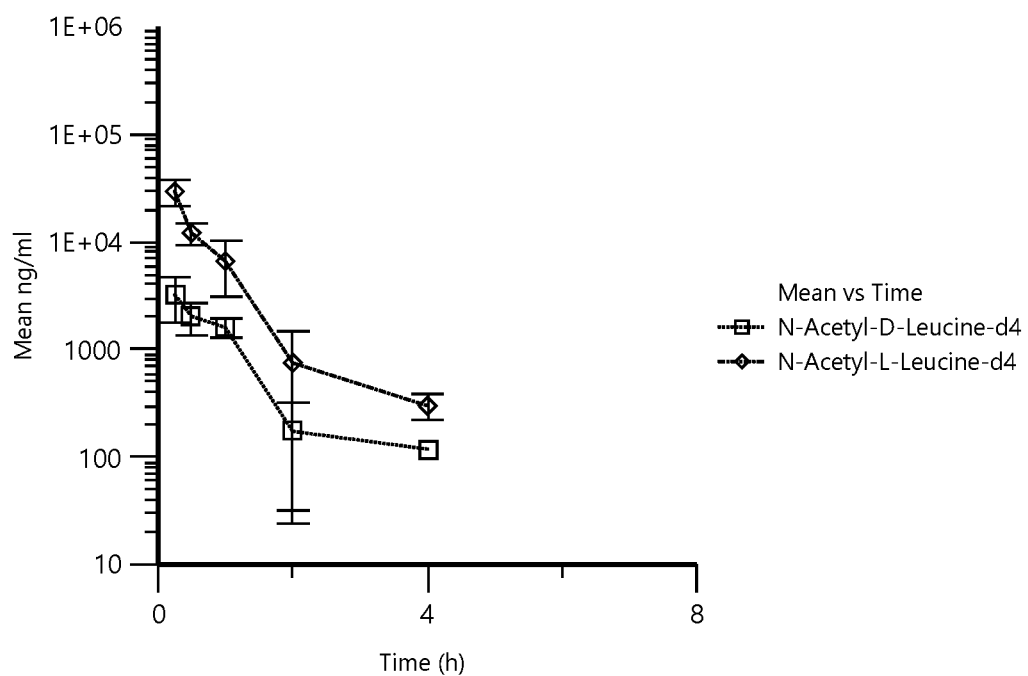
FIG. 6 is a line graph showing the plasma concentration vs. time profile for acetyl-D-leucine-2,3,3,4-$d_4$ (referred to as N-acetyl-D-leucine-$d_4$) and acetyl-L-leucine-2,3,3,4-$d_4$ (1) (referred to as N-acetyl-L-leucine-$d_4$) after p.o. administration of acetyl-L-leucine-2,3,3,4-$d_4$ (1) to male BALB/c mice a dose of 100 mg/kg in saline.

Acetyl-leucine-2,3,3,4-$d_4$ (referred to as rac-N-Acetyl-leucine-$d_4$) displayed significantly greater effect than that of acetyl-leucine (referred to as N-Acetyl-DL-leucine). For instance, 1 mM acetyl-leucine-2,3,3,4-$d_4$ displayed a significant reduction in LysoTracker fluorescence level compared to 1 mM acetyl-leucine. The effects were observed in both in a NPC CHO cell line and Tay-Sachs, AB Variant human fibroblast cell line. The results are shown in FIG. 1 and FIG. 2.

Example 12

Pharmacokinetic Studies

Acetyl-leucine, acetyl-L-leucine, acetyl-leucine-2,3,3,4-$d_4$ (1-rac), and acetyl-L-leucine-2,3,3,4-$d_4$ (1) were administered to male BALB/c mice via the oral (p.o) route. Plasma and tissue samples were collected at predetermined time points and analysed using HR/MS. Plasma concentration vs time curves are presented in FIGS. 3-6.

After p.o. administration of acetyl-leucine at a nominal dose of 100 mg/kg, $C_{max}$ of acetyl-D-leucine, 86,100 ng/ml, was achieved at 0.25 h post-dose with $AUC_{last}$ of 57,800 h*ng/ml; $C_{max}$ of acetyl-L-leucine, 3,410 ng/ml was achieved at 0.25 h post-dose with $AUC_{last}$ of 2,600 h*ng/ml. The ratios for L-form/D-form were thus 0.04 for both $C_{max}$ and $AUC_{last}$. See FIG. 3.

After p.o. administration of acetyl-leucine-2,3,3,4-$d_4$ (1-rac) at a nominal dose of 100 mg/kg, $C_{max}$ of acetyl-D-leucine-2,3,3,4-$d_4$, 50,600 ng/ml, was achieved at 0.50 h post-dose with $AUC_{last}$ of 99,600 h*ng/ml; $C_{max}$ of acetyl-L-leucine-2,3,3,4-$d_4$ (1), 3,880 ng/ml was achieved at 0.25 h post-dose with $AUC_{last}$ of 3,430 h*ng/ml. The ratios for L-form/D-form were thus 0.08 for $C_{max}$ and 0.03 for $AUC_{last}$. See FIG. 4.

After p.o. administration of acetyl-L-leucine at a nominal dose of 100 mg/kg, $C_{max}$ of acetyl-D-leucine, 436 ng/ml, was achieved at 0.25 h post-dose with $AUC_{last}$ of 573 h*ng/ml; $C_{max}$ of acetyl-L-leucine, 16,800 ng/ml was achieved at 0.25 h post-dose with $AUC_{last}$ of 11,400 h*ng/ml. The ratios for L-form/D-form were thus 38.5 for $C_{max}$ and 19.8 for $AUC_{last}$. See FIG. 5.

After p.o. administration of acetyl-L-leucine-2,3,3,4-$d_4$ (1) at a nominal dose of 100 mg/kg, $C_{max}$ of acetyl-D-leucine-2,3,3,4-$d_4$, 3,230 ng/ml, was achieved at 0.25 h post-dose with $AUC_{last}$ of 3,150 h*ng/ml; $C_{max}$ of acetyl-L-leucine-2,3,3,4-$d_4$ (1), 29,300 ng/ml was achieved at 0.25 h post-dose with $AUC_{last}$ of 18,200 h*ng/ml. The ratios for L-form/D-form were 9.08 for $C_{max}$ and 5.78 for $AUC_{last}$. See FIG. 6.

These data show that when either deuterated or non-deuterated acetyl-leucine was administered, the ratios for $C_{max}$ and $AUC_{last}$ for acetyl-D-leucine-2,3,3,4-$d_4$/acetyl-D- leucine were 0.59 and 1.72, respectively. The ratios for $C_{max}$ and $AUC_{last}$ for acetyl-L-leucine-2,3,3,4-$d_4$ (1)/acetyl-L-leucine were 1.14 and 1.32, respectively.

These data also show that when either deuterated or non-deuterated acetyl-L-leucine was administered, the ratios for $C_{max}$ and $AUC_{last}$ for acetyl-D-leucine-2,3,3,4-$d_4$/acetyl-D-leucine were 7.40 and 5.50, respectively. The ratios for $C_{max}$ and $AUC_{last}$ for acetyl-L-leucine-2,3,3,4-$d_4$ (1)/acetyl-L-leucine were 1.75 and 1.61, respectively.

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof. All patents, patent applications, and publications cited herein are fully incorporated by reference herein in their entirety.

What is claimed is:

1. A compound, or a pharmaceutically acceptable salt thereof, that is:

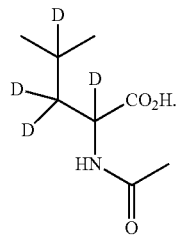

2. A compound, or a pharmaceutically acceptable salt thereof, that is:

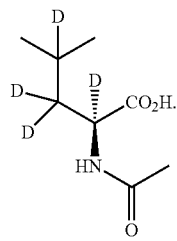

3. A pharmaceutical composition comprising the compound of claim 1 or 2, or a pharmaceutically acceptable salt thereof, and a pharmaceutically acceptable excipient.

4. A method of treating or delaying the progression of a lysosomal storage disorder, the method comprising administering to a subject in need thereof a therapeutically effective amount of the compound of claim 1 or 2, or a pharmaceutically acceptable salt thereof.

5. The method of claim 4, wherein the lysosomal storage disorder is Niemann-Pick Type C, Tay-Sachs disease, Sandhoff disease, GM1 gangliosidosis or Fabry disease.

6. The method of claim 5, wherein the lysosomal storage disorder is Niemann-Pick Type C.

7. The method of claim 5, wherein the lysosomal storage disorder is Tay-Sachs disease.

8. The method of claim 5, wherein the lysosomal storage disorder is Sandhoff disease.

9. The method of claim 5, wherein the lysosomal storage disorder is GM1 gangliosidosis.

10. The method of claim 5, wherein the lysosomal storage disorder is Fabry disease.

11. A method of providing neuroprotection in a subject having a lysosomal storage disorder, the method comprising administering to a subject in need thereof a therapeutically effective amount of the compound of claim 1 or 2, or a pharmaceutically acceptable salt thereof.

12. A method of treating or delaying the progression of a neurodegenerative disease, the method comprising administering to a subject in need thereof a therapeutically effective amount of the compound of claim 1 or 2, or a pharmaceutically acceptable salt thereof.

13. A method of treating or preventing a migraine, and the symptoms associated therewith; improving mobility; improving cognitive function; treating or preventing restless legs syndrome, and the symptoms associated therewith; or treating or preventing vertigo, and the symptoms associated therewith, the method comprising administering to a subject in need thereof a therapeutically effective amount of the compound of claim 1 or 2, or a pharmaceutically acceptable salt thereof.

14. The method of claim 13 for treating or preventing a migraine, and the symptoms associated therewith.

15. The method of claim 13 for improving mobility.

16. The method of claim 13 for improving cognitive function.

17. The method of claim 13 for treating or preventing restless legs syndrome, and the symptoms associated therewith.

18. The method of claim 13 for treating or preventing vertigo, and the symptoms associated therewith.

19. A kit comprising the compound of claim 1 or 2, and instructions for administering the compound to a subject to treat or delay progression of a lysosomal storage disorder, treat or delay the progression of a neurodegenerative disease, treat or prevent a migraine, and the symptoms associated therewith, treat or prevent restless legs syndrome, and the symptoms associated therewith, treat or prevent vertigo, and the symptoms associated therewith, or improve mobility and cognitive function.

20. A kit comprising the compound of claim 1 or 2, and instructions for administering the compound to provide neuroprotection in a subject having a lysosomal disorder.

* * * * *